United States Patent [19]

Segalowitz

[11] Patent Number: 5,511,553
[45] Date of Patent: Apr. 30, 1996

[54] DEVICE-SYSTEM AND METHOD FOR MONITORING MULTIPLE PHYSIOLOGICAL PARAMETERS (MMPP) CONTINUOUSLY AND SIMULTANEOUSLY

[76] Inventor: Jacob Segalowitz, 505 S. Beverly Dr., Ste. 1240, Beverly Hills, Calif. 90212

[21] Appl. No.: 330,526

[22] Filed: Oct. 28, 1994

Related U.S. Application Data

[63] Continuation-in-part of Ser. No. 273,535, May 3, 1994, which is a continuation of Ser. No. 911,561, Jul. 7, 1992, Pat. No. 5,307,878, which is a continuation-in-part of Ser. No. 818,398, Jan. 2, 1992, abandoned, which is a continuation of Ser. No. 473,887, Feb. 7, 1990, abandoned, which is a continuation-in-part of Ser. No. 310,660, Feb. 15, 1989, Pat. No. 4,981,141.

[51] Int. Cl.⁶ .................................................. A61B 5/00
[52] U.S. Cl. ........................................ 128/696; 128/903
[58] Field of Search .................................. 128/696, 903, 128/639, 640, 641, 644

[56] References Cited

U.S. PATENT DOCUMENTS 4,955,381  9/1990  May et al. .
5,080,099  1/1992  Way et al. .
5,224,485  7/1993  Powers et al. .
5,307,817  5/1994  Guggenbuhl et al. .

*Primary Examiner*—George Manuel

[57] ABSTRACT

A device, system and method for monitoring continuously and simultaneously multiple physiological parameters from a patient, comprising a precordial strip-patch having first and second surfaces and multi-layer flexible structure permitting telemetering data by radio frequency or single wire or fiberoptic to hardware recording and display monitor. A plurality of conductive contact elements (CCEs) and microsensors are mounted in spaced apart positions on said strip-patch device-system permitting simultaneously and continuously detection, microprocessing and transmission of microsensored and detected physiological data for monitoring standard 12-lead ECG, cardiac output, respiration rate, peripheral blood oximetry, temperature of a patient, and electrocardiographic fetal heart monitoring, via a single wavelength of radio frequency transmission or single-wire or single fiberoptic connection to recording hardware or display monitor.

39 Claims, 27 Drawing Sheets

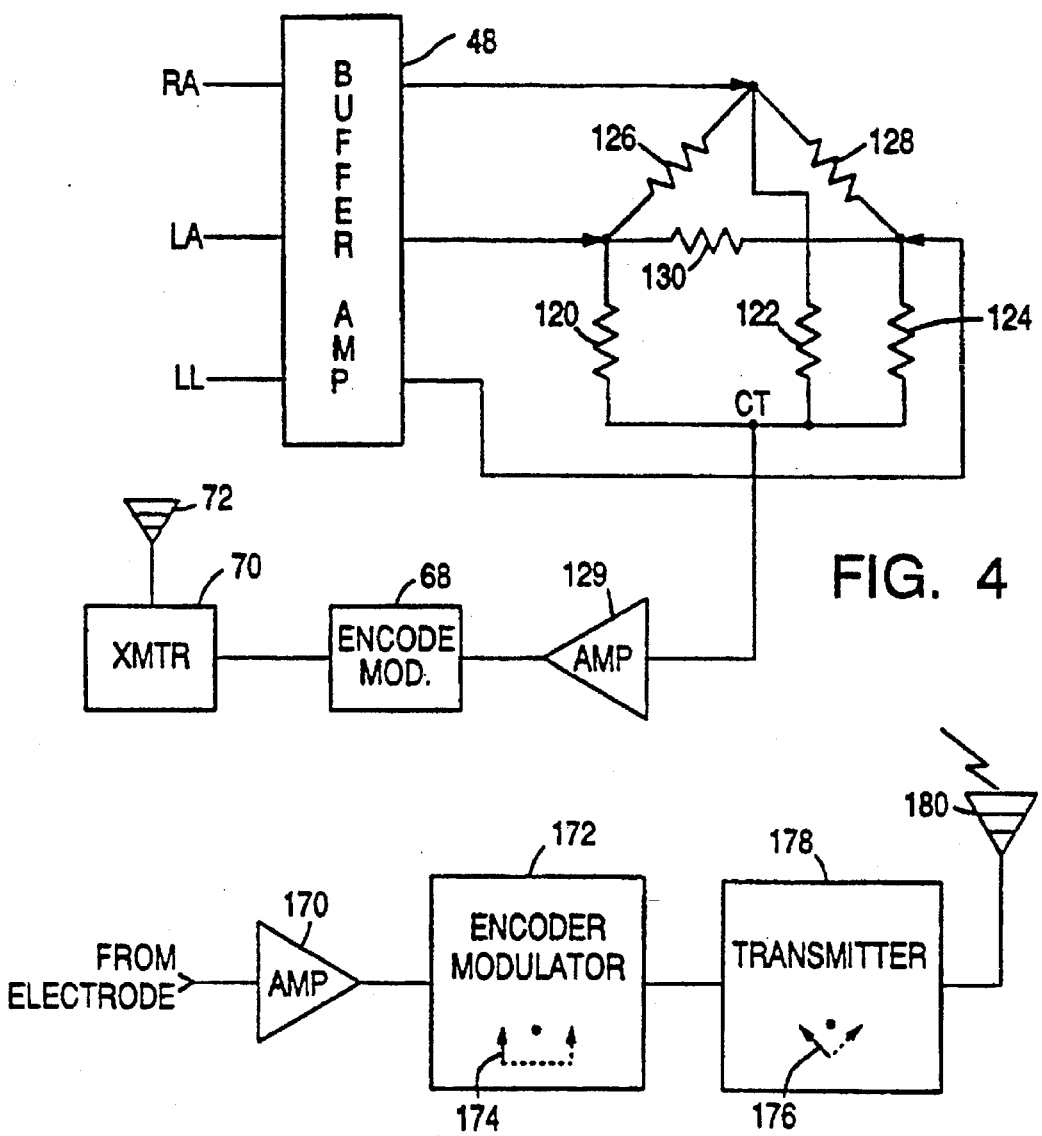
FIG. 4
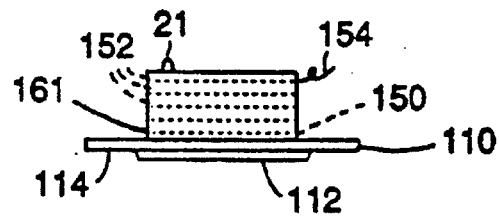
FIG. 7
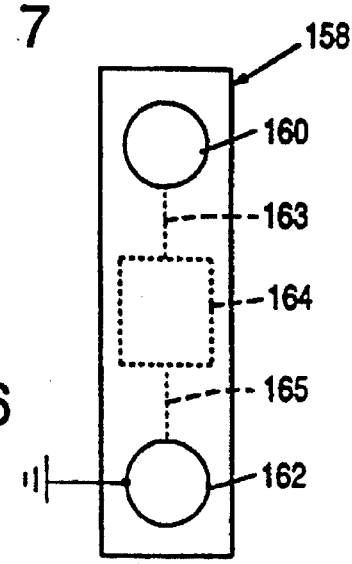
FIG. 5
FIG. 6

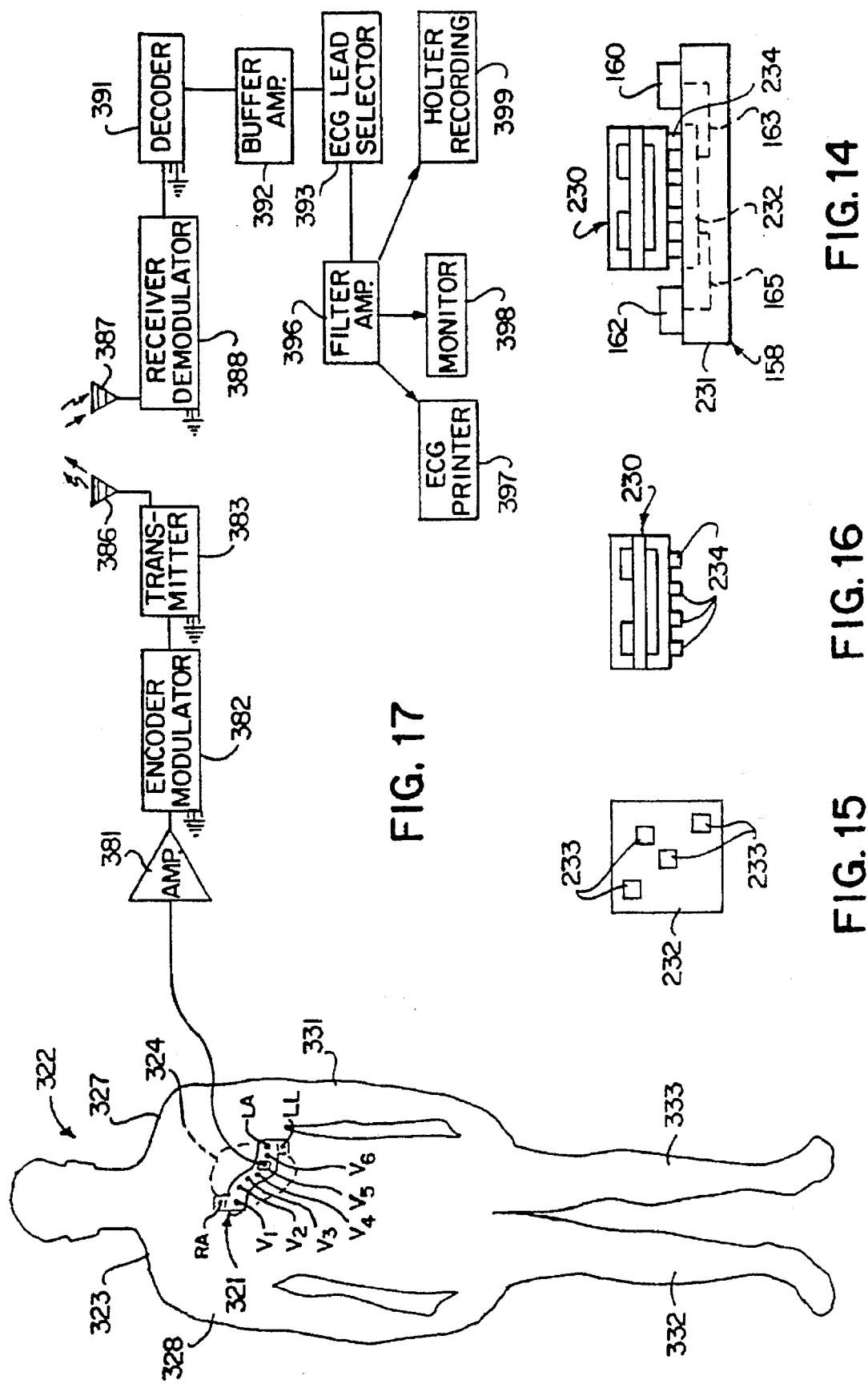

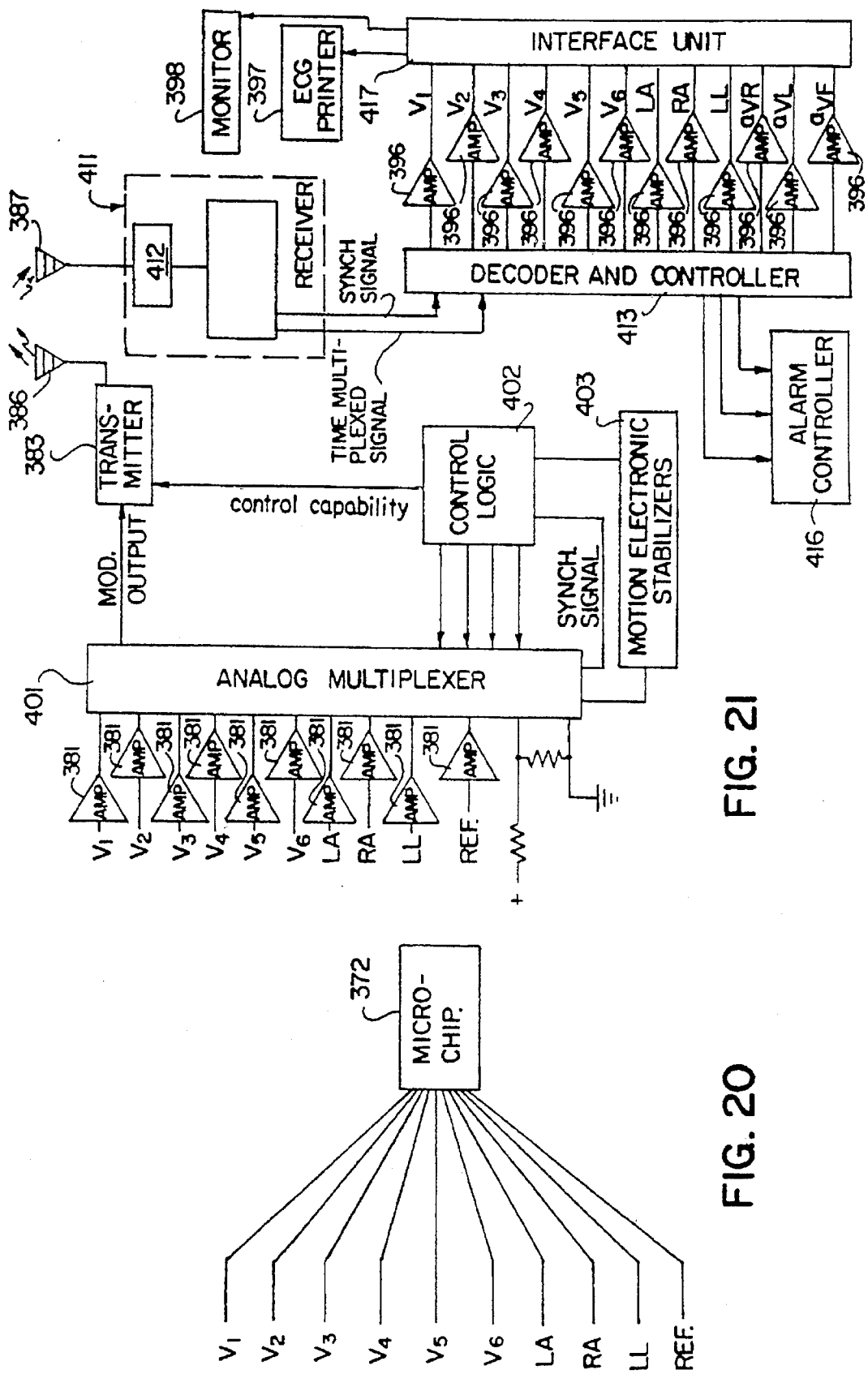

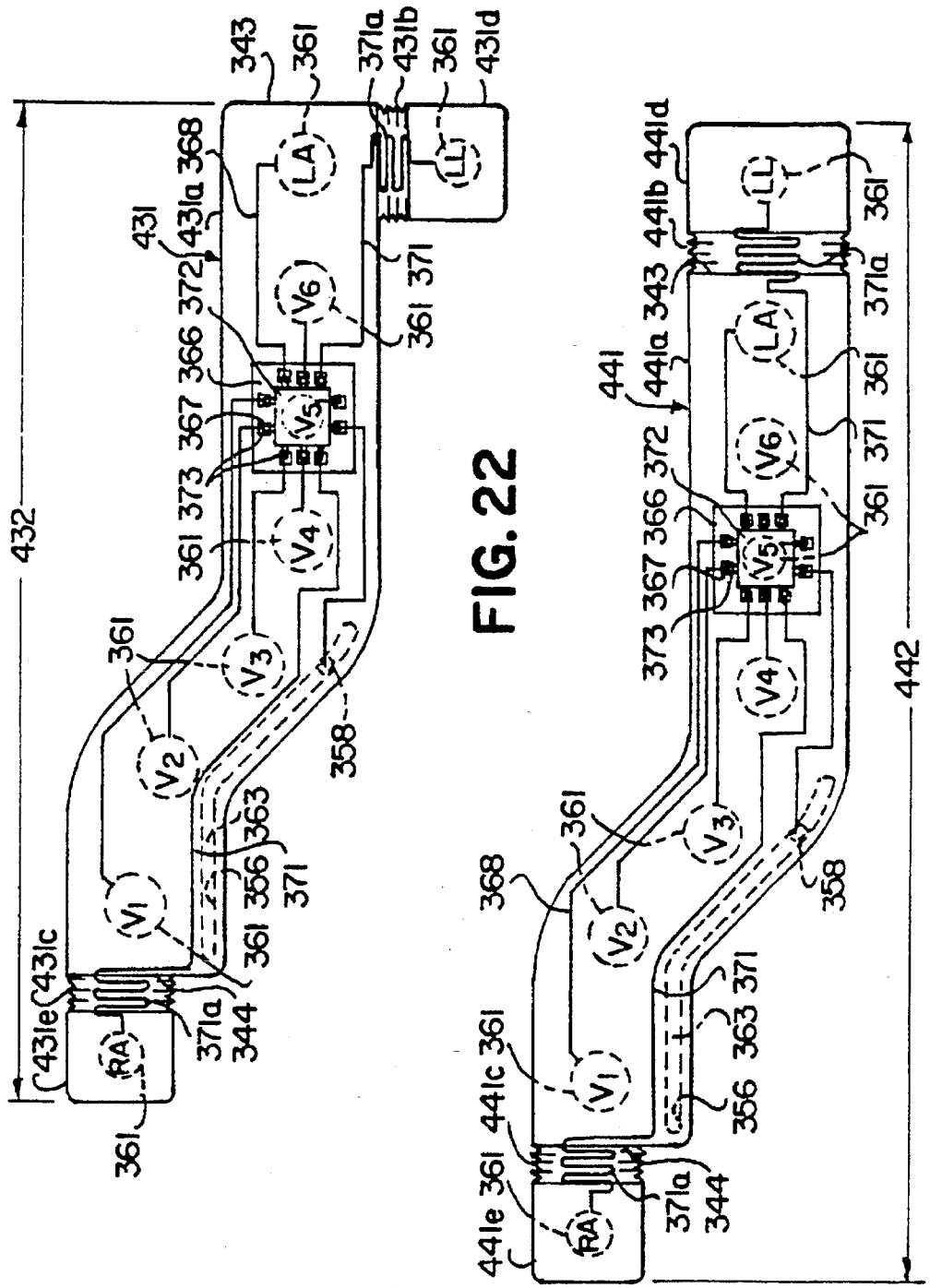

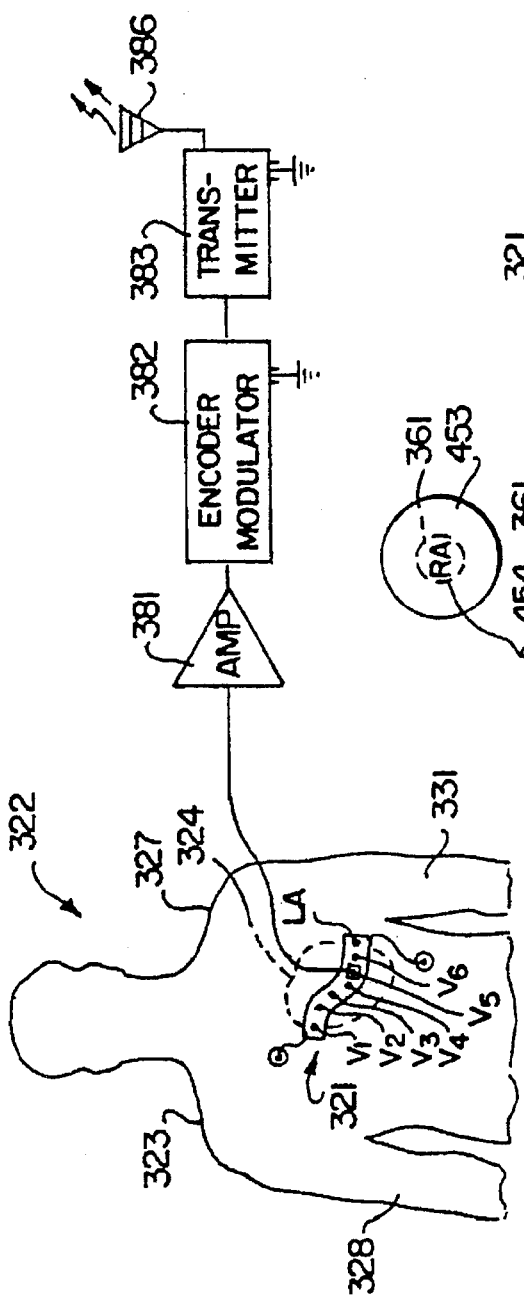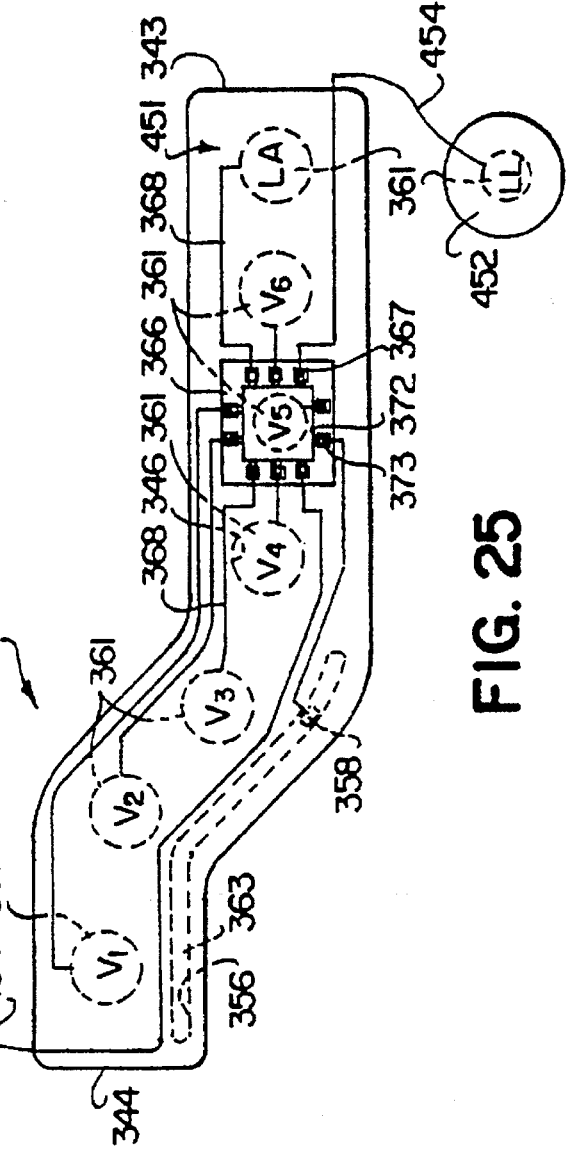
FIG. 24
FIG. 25

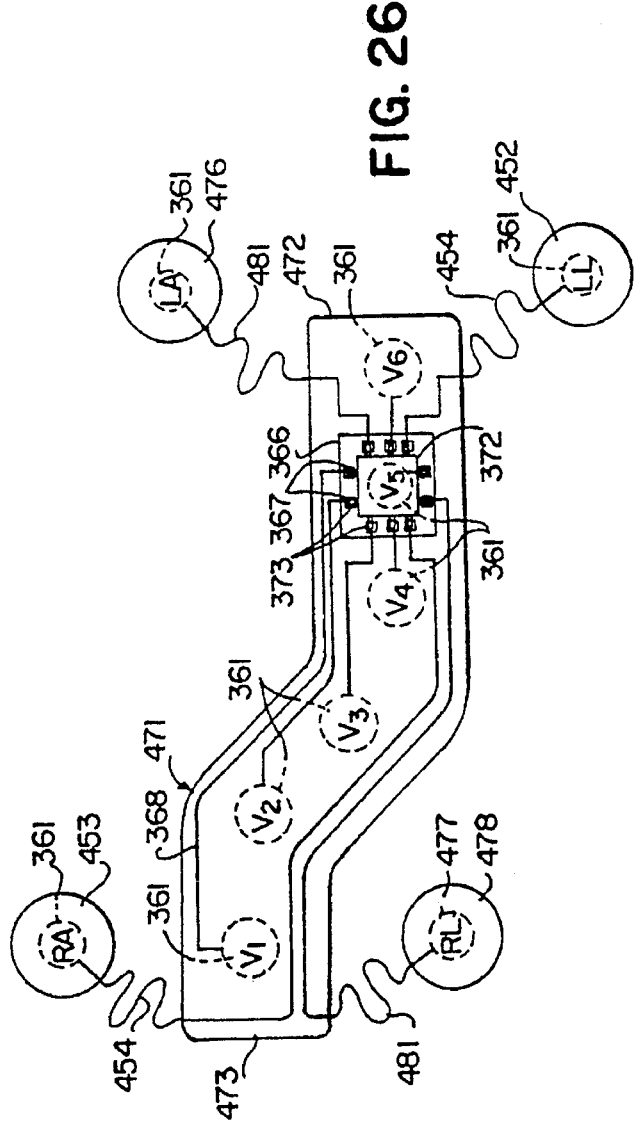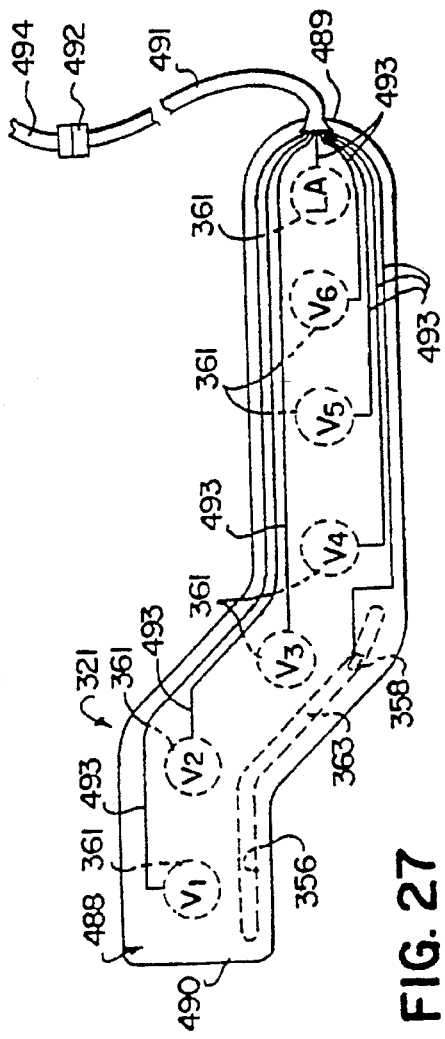

DEVICE-SYSTEM AND METHOD FOR MONITORING MULTIPLE PHYSIOLOGICAL PARAMETERS (MMPP) CONTINUOUSLY AND SIMULTANEOUSLY

BACKGROUND OF THE INVENTION

Cross-References to Related Patent Applications

This application is a continuation-in-part of U.S. Ser. No. 08/273,535, filed May 3, 1994, which is a continuation of U.S. Ser. No. 07/911,561 filed Jul. 7, 1992, U.S. Pat. No. 5,307,818 which is a continuation-in-part of U.S. Ser. No. 07/818,398, Jan. 2, 1992, abandoned, which is a continuation of U.S. Ser. No. 07/473,887, Feb. 7, 1990, abandoned, which is a continuation-in-part of U.S. Ser. No. 07/310,660, Feb. 15, 1989, U.S. Pat. No. 4,981,141.

1. Field of the Invention

This invention relates to a medical instrumentation device-system and method and for its use thereof and, more particularly, to electrophysiological parameters monitoring equipment, device-system and method relating thereto.

2. Prior Art

Monitoring modalities of physiological parameters and their currently available associated instrumentation are cumbersome, expensive, complex, and occasionally lack accuracy. The field of microsensor technology has gained increasing importance in recent years, in part due to advancement, reliability, capability and low-cost of today's analog and digital integrated circuits, microprocessors and semiconductors. The field of microsensors bears the potential to hold the keys to the applications of microelectronics of the future, having the potential to revolutionize the use of medical instrumentation with the aid of microelectronics. Microelectronics technology is well known for its ability to enable the production of small devices with extreme dimensional precision, accuracy and reproducibility. Although the high degree of sophistication is associated with manufacturing, microelectronic devices are affordable due to potential for batch fabrication of silicon, gallium-arsenide or similar structured wafers.

A major advantage of microsensors is the very nature of the semiconductor material sensitivity, such as silicon or gallium-arsenide. Since electronic devices can be fabricated on silicon or gallium-arsenide wafers, another unique advantage of microsensors is their ability to integrate multiple and appropriate levels of signal processing circuits for signal amplification, filtering, coding, multiplexing, etc. on the same chip with the added advantages of higher sensor signal-to-noise ratio, faster data processing, compensation for environmental factors and overall cost reduction. By integrating the sensing element, especially when an array of sensing elements can be employed with signal processing circuits on chip, it is possible to develop the future generation of "smart microsensors" and "smart instruments".

Another important advantage of microsensors is the micromachining in which the process of three-dimensional forming and shaping of silicon and other semiconductors, ceramic and polymeric materials, enables microsensor fabrication precisely, reproducibly and at a low cost. Further advantage of microsensors is in their compatibility to operate with other microelectronic technologies. Microsensors offer some of the most attractive advantages for future medical applications, whether these microsensors are for single-use or repeated use, long- or short-term implant, invasive or non-invasive: small size, high sensitivity, high stability, accuracy and reproducibility, reliability, rapid response, biocompatibility, and affordable cost.

One of the important medical application for which microsensors technology can be used for, is electrocardiography. Human physiology implies that every muscle can perform only one movement, the shortening of its fibers by contraction. This also applies to the heart muscle. Every action of a muscle has associated with it an electrical activity which changes in the course of the contraction. The electrical signal thus associated with the muscle action is transmitted through various tissues and ultimately reaches the surface skin of the body whereupon such electrical signals can be detected by electrodes or sensors applied to the skin. Thus, such signals that are being detected by the electrodes or sensors can be recorded with the aid of suitable electrocardiographic equipment or can be observed on or recorded with a monitor/recording unit. The record thus obtained is called an electrocardiogram (ECG) or a rhythm-monitoring strip.

As early as 1855 action currents from the heart's muscle were recorded as measurements of a beating heart of a frog. Modern electrocardiography started with Wilson, credited with the unipolar lead setting for recording of standard precordial leads $V_1$, $V_2$, $V_3$, $V_4$, $V_5$, $V_6$, aVR, aVL, aVF, and Einthoven, credited with the bipolar lead triangle setting for recordings of standard limb leads I, II and III. The combination of both Wilson's nine unipolar lead settings and Einthoven's three bipolar lead settings results in the recording of 12-lead ECG, which is considered to be the "gold standard" for ECG testing until presently. Wilson's and Einthoven's recording techniques have not been improved upon very much since they were first published many years ago. It should be noted here that the term "lead" as relates to ECG is being used in the medical sense and not in the electronic sense, i.e., "lead" is a spatial position from which the heart electrical activity is viewed upon, not a wire.

The entire standard twelve-lead ECG system is fed by nine unipolar leads and three bipolar leads. Unipolar leads are divided into three unipolar extremity or limb leads and six unipolar precordial or chest leads. In the unipolar lead system, the limb leads are: aVR—the unipolar right arm lead, (R designating the right arm); aVL—unipolar left arm lead, (L designating the left arm); and, aVF—unipolar left leg lead (F designating the left leg). In all of these unipolar limb leads, the "a" stands for "augmented". The unipolar chest leads on the precordium are designated by the letter "V" followed by a subscript numeral which represents the exact location of said lead on the chest. In standard electrocardiographic setting there are six precordial leads, $V_1$, $V_2$, $V_3$, $V_4$, $V_5$, and $V_6$. In the standard unipolar lead system, the potential differences are measured between each of the electrodes that are placed on the right arm, left arm, left leg and precordial points $V_1$–$V_6$ on the chest, and a common reference point consisting of an electrode placed on the right leg. Each of such electrodes in the conventional setting is independently considered as an "active" point compared to the common reference electrode (point) on the right leg, and is measured in relation to that common reference electrode. In standard bipolar leads I, II, and III, lead I is the potential difference between the arms, i.e., the left arm potential minus the right arm potential; Lead II is the potential difference between the left leg potential and the right arm potential; and Lead III is the potential difference between the left leg and the left arm. If the bipolar leads I, II, and III are diagrammed on the body they inscribe, essentially, an equilateral triangle ("Einthoven's Triangle"). The polarity of these widely-separated bipoles was arbitrarily determined many years ago in order to record upright electrical deflections in these three limbs leads in most normal objects.

The electrocardiograph generates the lead voltages from the potentials applied to it from the sensing electrodes. The "view" of the heart's electrical signals varies among leads. For standard 12-lead ECG recording, the standard electrocardiograph requires at least ten terminal wires to connect between the patient and the hardware: three wires which connect to each of the electrodes placed on the right arm (RA), left arm (LA) and left leg (LL), and six wires which connect to each of the six electrodes placed on the precordium at $V_1$–$V_6$. One additional wire connects the common reference electrode placed on the right leg. These ten terminal wires are attached to the body of the patient at one end and to the electrocardiograph at the other end to detect heart-signals and transform them, at the hardware end, into a twelve-lead electrocardiographic evaluation. In addition to the multiple wires connection, this involves attaching six electrodes to the patient's chest precordial area to obtain recordings of leads $V_1$–$V_6$, as well as attaching four electrodes to the arms and legs of the patient to obtain recordings of leads I, II, III, aVR, aVL and aVF. For heart rhythm (heart-rate) monitoring, only three electrodes and three terminal wires are applied to the chest. After the ten electrodes are attached to the patient, the ten specific wires must be connected between each specific electrocardiograph terminal wire and each specifically related electrode at the predetermined position of side and location on the patient's body.

In electrocardiographic terminology, the terms "dipole," "bipole" and "unipole" have different meanings and applications. The "single dipole" concept is used to represent the local spread of excitation over cardiac tissue as recorded by a single recording electrode. This local excitation is in the form of a local influx and/or outflux of electrically charged elements, referred to as ions, through the cell membrane. The term "equivalent dipole" has been a term used since the days of Einthoven to represent the theoretical "electrical center" of a volume conductor used to describe the progression, magnitude and location of the electrical activity of the human body. This "equivalent dipole" has both direction and magnitude at any instance in the cardiac cycle and is traditionally represented as a vector that points in the direction of the positive pole of a dipole having both positive and negative poles. The vector has a length proportional to the magnitude of the dipoles' potential difference, i.e., the potential difference between its positive and negative poles.

The term "bipolar" has several uses in clinical electrocardiography and electrophysiology. Bipolar endocardial and epicardial recordings refer to recordings made between a cathode and anode of a recording device which are relatively closely spaced, i.e., several millimeters to one centimeter. For example, bipolar cardiac recordings are taken by modern pacemakers having leads that are reasonably closely spaced. In surface electrocardiographic practice, bipolar lead systems, as discussed above, are defined as limb lead systems that measure the potential differences between the three limb electrodes on the right and left arms and the left leg. The term "unipolar" is used in the practice of surface electrocardiography as described above.

The electrocardiograph is widely used in all fields of medicine. The conventional and currently existing 12-lead electrocardiographic systems are limited in use due to cumbersome operation, time consuming and expensive cost. As a result of these major practical disadvantages, in most circumstances, routine monitoring of cardiac activity is aimed to detect arrhythmia only rather then to enable complete diagnosis by standard 12-lead electrocardiogram, therefore, resulting in limited capability to diagnose and evaluate critical information of the heart's function, dynamics of myocardial ischemia, myocardial infarction (heart attack), pathogenesis of arrhythmia, and more.

An early manifestation of myocardial ischemia is the development of ST-segment and T-wave changes, and clinical decisions for treatment are based on ST-segment shifts on the surface electrocardiogram. ST-segment depression is believed to represent sub-endocardial involvement, with less extensive myocardial injury. ST-segment elevation reflects transmural involvement, with a greater extent of myocardial injury. Currently existing electrocardiographic monitoring equipment in the coronary intensive care units (CICU), coronary intensive care mobile unit and intensive care units (ICU), provides single-lead arrhythmia monitoring of cardiac events which is unable to detect myocardial ischemia (the dynamics of decreased supply of blood to the heart muscle that may lead to heart attack) or myocardial infarction (heart attack), in real time occurrence.

Also, protocols in the operating room during surgery under general anesthesia, and in the cardiac catheterization laboratory during diagnostic heart catheterization and percutaneous transluminal coronary angioplasty (PTCA) (balloon angioplasty) procedures, employ the use of single-lead or three-lead arrhythmia monitoring which is unable to detect the dynamics or events of myocardial ischemia or myocardial infarction during surgery or during the actual performance of such invasive percutaneous coronary interventions.

Further, in the ambulatory setting, Holter monitoring, also provides only arrhythmia detection and time-limited recording, which is unable to identify or diagnose dynamics of coronary ischemia or evolvement of myocardial infarction (heart attack). Furthermore, transtelephonic electrocardiographic monitoring currently employs single-lead arrhythmia monitoring which is unable to identify or diagnose events of myocardial ischemia or myocardial infarction in patients who have undergone diagnostic heart catheterization, PTCA, coronary artery bypass graft (CABG) surgery, or in patients awaiting for cardiac surgery, being treated with anti-arrhythmic drugs, or experiencing angina pectoris episodes. Current transtelephonic ECG monitoring are also limited to record symptomatic events only, and completely missing silent events of myocardial ischemia dynamics and silent evolvement of myocardial infarction.

Existing protocols employ single-lead electrocardiographic monitoring also in other settings, as during coronary intensive care mobile unit care and during emergency room care, thereby, permitting arrhythmia monitoring only without the capability to diagnose or evaluate critical heart conditions such as myocardial ischemia or myocardial infarction.

As it can be seen, currently available electrocardiographic monitoring techniques are aimed mostly at the detection of cardiac arrhythmia rather than diagnosis of myocardial ischemia or myocardial infarction by "complete" electrophysiological evaluation of standard 12-lead ECG.

Routine ECG monitoring of rhythm detection is also limited in diagnosing myocardial ischemia or myocardial infarction after non-cardiac surgery. Patients undergoing non-cardiac surgery, often have postoperative cardiac events that are a major cause of morbidity and mortality after such surgery. It is necessary and would be clinically invaluable to determine the predictors of these outcomes, in order to focus efforts on prevention and better treatment. It would be helpful and critical to know, for patient benefit, which patients are at highest risk. Clinical experience and studies have demonstrated and suggest that postoperative myocardial ischemia during the first 48 hours after major non-cardiac surgery confers a nearly three-fold increase in the odds of having an adverse cardiac outcome and, more importantly, about nine-fold increase in the odds of having an ischemic event that may complicate to cardiac death, non-fatal myocardial infarction or unstable angina. In some clinical studies, postoperative myocardial ischemia was prevalent, occurring in more than 40 percent of the patients undergoing non-cardiac major surgery, and was silent in nearly all cases reported in those studies.

In addition to such clinical disadvantages resulting from the use of non-12 lead ECG monitoring, many and frequent difficulties are also associated with the practical operation of the conventional and currently existing electrocardiographic systems for 12-lead ECG, due to the following factors:

1. The need to connect multiple predetermined specific wires to multiple predetermined specific electrodes is time consuming; i.e., the need to connect four predefined terminal wires to four predefined electrodes that are positioned on a specific limb and side, as well as the need to connect six predefined precordial terminal wires to six specific precordial electrodes that are positioned on the patient's chest. In addition, connection errors are relatively frequent.

2. The multiple terminal wires often need to be untangled, resulting in the loss of precious time, or triggering false connection of wires to electrodes that may result in false ECG recording.

3. Existing standard 12-lead electrocardiographic systems are cumbersome and impractical for use in coronary intensive care mobile units when speed of operation is critical, causing to another direct disadvantage of having only limited diagnosis and evaluation capabilities of critical ECG information.

4. Wire defects and damage are difficult to detect.

5. During many surgical procedures, single-lead arrhythmia monitoring wires extend beneath the sterile surgical field. These wires often become disconnected from the electrodes place on the patient's skin and interrupt the surgical procedure when need to be reconnected. In addition, existing electrocardiographic systems do not permit myocardial ischemia or myocardial infarction detection during surgery.

6. Patients in intermediate coronary care sometimes disconnect the signal carrying wires from the electrocardiographic monitor while ambulating. By doing so, cardiac rhythm monitoring is interrupted.

7. Current electrocardiographic monitoring is proximity limited in distance by the wires extending between the patient and the electrocardiograph or monitor hardware.

8. Current protocols of percutaneous transluminal coronary angioplasty (PTCA), diagnostic heart catheterization and other invasive interventional procedures performed in the cardiac catheterization suite; monitoring in coronary intensive care units (CICU), intensive care unit (ICU) and coronary intensive care mobile units; and, thrombolytic therapy monitoring; each employs single-lead or three-lead electrocardiographic detection which provides only arrhythmia monitoring and is unable to diagnose or evaluate events of myocardial ischemia or myocardial infarction.

9. Patient compliance (comfort level) with currently available electrocardiographic equipment for 12-lead ECG recording, is minimal.

In addition to electrocardiography monitoring, currently available monitoring equipment of multiple physiological parameters is short of providing a single device or uniform equipment. Most of the monitoring equipment in use is relatively complicated to operate, each hardware addresses another test, equipment is expensive, and requires multiple and different instrumentations or displays in order to monitor multiple physiological parameters from a patient. Further, multi-parameter monitoring is intermittent and is unavailable in most circumstances, unless the patient is already in critical conditions and is under intensive care. During coronary intensive care, as well as in the operating-room during and after major non-cardiac surgery, before and after cardiac surgery, during coronary intensive care mobile unit care, emergency room and trauma care, the use of continuous multi-parameter physiological monitoring is essential and critical to the patient. Routine monitoring of cardiac output, respiration rate, peripheral blood oximetry and temperature levels, are everyday clinical practice in those circumstances. In various clinical settings, the existing protocols employ the monitoring of only a part of a wide range of this needed clinical information that could be evaluated if it would have been more readily available, simpler, easier and faster to obtain, and economically affordable.

The assessment of hemodynamics with the bedside measurements of cardiac function has become a standard in the critically ill patients. In hearts with reduced ventricular function there can be a combination of ECG and thoracic impedance tracing to allow the prediction of the heart's ventricular function, which would enable comprehensive and critical hemodynamic profiling during intensive care. Impedance cardiography of the thorax can be used to calculate cardiac output. Impedance cardiography can provide valid estimation of stroke volume (SV) (blood volume ejected by the left ventricle of the heart during one systole) and ejection fraction (EF) (systolic volume/end-diastolic volume); therefore, end-diastolic volume (EDV) can be calculated from EDV=(SV/EF)−SV. Currently, there are six established methods for measuring cardiac output. Three of these methods are indicator dilution (direct Fick, thermodilution, dey dilution), and three methods visualize the heart chambers and calculate stroke volume (contrast cine-angiography, echocardiography, gated blood-pool radionuclide angiography). Additional bedside technology and method employ invasive catheterization of pulmonary artery flow-directed balloon-tipped catheter (Swan-Ganz catheter); along with an arterial line, it provides a comprehensive hemodynamic profile. However, invasive monitoring is relatively expensive, logistically limited, time consuming, and potentially risky and hazardous approach that provides only intermittent data and is justified in relatively a small percentage of intensive care patients. There is a need for method to assess continuously the adequacy of cardiac output and, ultimately, peripheral oxygen perfusion.

Further, hemodynamics assessment of pacemaker patents is necessary for gauging responses to changes in programming of pacemakers or conditions affecting circulation. Impedance cardiography can be used for non-invasive determination of cardiac output at short intervals. Small variations in atrioventricular timing may result in significantly altered hemodynamics. A simple, non-invasive method, capable to measure cardiac output, would aid in programming pacemakers in patients with for optimal hemodynamic benefit. Impedance cardiography is a non-invasive method of cardiac output determination that would allow repetitive measurements at short intervals with low variability, that can be directly and continuously linked to the operation, triggering and control of and by pacemakers.

The continuous and simultaneous monitoring and availability of ECG and cardiac output and respiration rate and peripheral blood oximetry and temperature, of a patient, with a single device-system as disclosed herein, by wireless or with only a single wire or fiberoptic connection to monitoring or recording hardware, will significantly expand and facilitate the use of multi-parameter monitoring, enable continuous monitoring, improve patients' comfort and compliance, overcome distance limitation of monitoring, facilitate use of equipment by the medical personnel, reduce the learning-curve associated with equipment's operation, avoid false-negative or false-positive of testing, expand the u@ and make available more clinical information by a more complete but simple and economical monitoring system, avoid the need to rely on multiple manufacturers and vendors, avoid repetitive testing, save precious time clinically, facilitate test results sharing among medical experts, save cost of personnel time, and potentially reduce the overall costs of patient care. Furthermore, the simultaneous and continuous monitoring of multiple physiological parameters by such herein mentioned single device-system that will be compatible to operate with already existing recording or display hardware equipment, will allow an immediate or gradual and economical upgrade of equipment into such herein disclosed "next generation" of patient monitoring.

Further, the strip-patch device system of the present invention will permit continuous electrocardiographic monitoring of a fetus and his mother during the period of pregnancy; it would enable an effective, simple, portable, economical and easy-to-use wireless device, that would allow continuous invaluable fetal heart monitoring during high-risk pregnancies, which account to be about 25% of all pregnancies worldwide. Such mother-fetus monitoring (MOFET Monitoring) by the WEMS strip-patch device-system of the present invention, can detect, simultaneously and separately for the fetus and the mother, both the maternal and fetal heart function, wirelessly and continuously, and transmit or link or interface it to a potable beeper-size device that may contain; microprocessor for real-time rapid elaboration of the detected heart signals; integrated software within the microprocessor calibrated to evaluate a preset and contained threshold level capable to trigger an sound and visible alarms to alert the mother about the need to seek medical help; cellular telephone incorporating preprogrammed one or two telephone numbers for automatic or by-demand communication capabilities to medical emergency services or to a doctor's office; and, microprocessing of digital-to-analog sound telemetering means to allow the use of conventional wired telephone communication.

Further, in addition to the WEMS' multi-parameter monitoring capabilities, the strip-patch device-system of the present invention, would enable for ambulatory or hospital-based patients to connect and interface by wireless means, or by single-wire or by single fiberoptic link, or by "electronic stamp interface" per-visit to the doctor's office or daily-link during hospitalization, to automated medical management systems. Such practical error-free link among patients and a large medical facility or doctor's office, would allow management automation of clinical data in real time, trace patients' always current records upon demand, avoid repetitive testing of patients, facilitate and accelerate comparative clinical evaluation of patient's testing (which could be automated by software), facilitate sharing of clinical information among medical professionals, avoid errors that are often associated with log of clinical data by manual cumbersome methods, potentially improve treatment of patients, and reduce the overall cost of patient's care.

Furthermore, the WEMS' strip-patch device and system would integrate within also artificial intelligence in its incorporated set of chips. Such logic and memory capabilities would allow "on-patient" portable and real-time continuous medical assessment and evaluation capabilities of multi-parameter and variable clinical conditions simultaneously, continuous evaluation of drug management, and alert the patient by audio and visual means of the need to seek medical help, if necessary.

Therefore, it is an object of the present invention to overcome the problems previously experienced in connection with the application of electrocardiographs in the taking of 12-lead electrocardiograms and in connection with the rhythm monitoring of patients.

Another object of the present invention is to provide an electrocardiographic and monitoring system in which the physical wires between the patient and the electrocardiograph or monitor are completely eliminated.

Another object of the present invention is to provide an electrocardiographic and monitoring system in which a reduced standard number electrodes provide standard 12-lead electrocardiogram.

Another object of the present invention is to provide a strip-patch device-system assembly containing a plurality of conductive elements and microsensors for placement on the chest area of a patient.

Another object of the present invention is to provide a strip-patch device-system assembly self-containing a reference conductive element permitting elimination of the right leg reference electrode.

Another object of the present invention is to provide a strip-patch device-system assembly having, in addition to $V_1$–$V_6$ conductive elements, also RA and LL or RL conductive elements positionable on the patient in a position remotely from the $V_1$ through $V_6$ and LA conductive elements.

Another object of the present invention is to provide a self-containing strip-patch device-system assembly for detecting and transmitting heart signals.

Another object of the present invention is to provide a strip-patch device-system assembly containing plurality of conductive contact elements and microsensors for detecting changes in the thoracic impedance for calculation and evaluation of cardiac output in a patient.

Another object of the present invention is to provide a strip-patch device-system assembly containing conductive contact elements and microsensors for detecting and monitoring the respiration rate of a patient.

Another object of the present invention is to provide a strip-patch device-system assembly containing conductive contact elements and microsensors to enable the measurement of temperature of a patient.

Another objective of the present invention is to provide a strip-patch device-system assembly containing conductive contact elements and microsensors for measurement of peripheral blood oximetry (oxygen concentration) in a patient.

Another object of the present invention is to provide a strip-patch device-system assembly containing conductive contact elements, microsensors, microprocessors, and semiconductors, to enable simultaneously and continuously monitoring of standard 12-lead electrocardiogram and cardiac output and respiration rate and blood oxygen concentration and temperature, of a patient.

Another object of the present invention is to provide a strip-patch device-system assembly and method self-contained one or more microchips having microsensors and microprocessors and transmitting means to enable elaboration, processing and transmission of each of the multiple electrophysiological signals and data detected by the plurality of conductive contact elements and microsensors.

Another object of the present invention is to provide a strip-patch device and system and method to enable simultaneously and continuously wireless monitoring of standard 12-lead ECG, cardiac output, respiration rate, blood oximetry and temperature, of a patient.

Another object of the present invention is to provide a strip-patch device assembly and system and method to enable, simultaneously and continuously, wireless electrocardiographic monitoring of and fetus during pregnancy period (MOFET Monitoring).

Another objective of the present invention is to provide a strip-patch device assembly and system and method which integrates microsensors, data processing, communication, control and user interface, which employs within microsensors that enable detection and monitoring, simultaneously and continuously, of standard 12-lead ECG, cardiac output, respiration rate, peripheral blood oximetry and temperature, of a patient.

Another objective of the present invention is to provide a strip-patch device assembly and system and method which integrates microsensors, data processing, control, user interface to be used via cellular or wired telephone communication for continuously and simultaneously monitoring of standard 12-lead ECG, cardiac output, respiration rate, blood oxygen and temperature, of a patient, as well as fetal heart monitoring.

Another objective of the present invention is to provide a strip-patch device assembly and system and method which integrates within and self contains communication means of cellular or wired telephone communications to allow automatic or manual communication capabilities between said strip-patch assembly and a doctor's office, hospital or monitoring facility.

SUMMARY OF THE INVENTION

In accordance with the preferred embodiments of the present invention there is disclosed a two-section medical device-system and method for multi-parameter physiological monitoring. One section includes a strip-patch assembly containing conductive contact elements (CCEs), microsensors and microchips that are affixed to the patient for detection and analysis of specific electrical signals, and the second section is the receiving and interfacing end to the recording or display hardware. No wires extend between the two sections for wireless operation, or a single fiberoptic or single-wire connection can be applied. The second section end interfaces with the electrocardiograph or monitoring equipment. Each wireless strip-patch operates independently of all of other similar strip-patch devices in the same environment and is self-contained microchips and self-powered by its own integrated power source (i.e., battery) within the structure of the strip-patch device. The strip-patch device individually radiates its signal/s via a single wavelength to a corresponding individual receiver in the receiving section interfaced to the display or recording monitoring hardware. To ensure that the receivers in the receiving-interface section operate on the proper radio frequency transmission wavelength from the strip-patch, each strip-patch transmits its digital signal with an encoded pattern that can be decoded only by its individually corresponding receiver-interface unit.

The present invention also presents several different configurations, or groupings, of the ten CCEs needed for a "complete" standard 12-lead electrocardiogram (ECG) monitoring. By grouping the CCEs, while maintaining their individual proper function, the number of appliances that have to be affixed to the patient is reduced, thus minimizing time-of-operation of monitoring equipment, reducing the amount of time necessary to apply the strip-patch, and further minimizing the chance of error from the connection of conventional terminal wires to the wrong electrode locations on the patient.

The electrocardiac activity information detected and transmitted by the wireless device-system of the present invention conforms to all professional standards and levels of accuracy for the signal's vector progression, duration, intensity, and form characteristics, specifically with respect to the following parameters: rhythm; rate; P wave; P-R interval; QRS interval; QRS complex; ST segment; T wave; U wave; Q-T duration.

The strip-patch device-system operates within the nominal range of approximately 50 meters (150 feet) between the strip-patch device-system and the receiving-interface section. This configuration is suitable for operation with either a single-channel or a multi-channel electrocardiograph, monitor, or Holter. Each of those ECG units may be fixed or portable, battery or AC powered. The receiving-demodulating-decoding section of the device-system of the present invention can be connected to existing stand-alone electrocardiographs or monitors or, by reason of its miniature size, can be integrated into new generations of such hardware machines. Interference between multiple systems operating in the same facility is prevented by choosing different center frequencies for each of the transmitters and their corresponding receivers within the corresponding system and all other systems, and using a different digitally encoded frequency for transmission by each strip-patch device-system. On the strip-patch device, the CCEs are spaced-apart from each other. Of these, one (for ECG) or more (for other monitoring) CCE is being used as common reference or common zero potential by all other CCEs. While reference has been made herein to a radio frequency (RF) system of coupling between the strip-patch on the patient's body and the receiving-interface section, it should be understood that with only minor changes in the circuitry and the proper operating environment, ultrasonic, semiconductors, fiberoptic or single wire techniques, as well as other technologies, may be used to enable the transmission or connection between the patient and the monitoring display or recording hardware.

In other embodiments of the present invention the electrode on the right leg, which serves as the common reference electrode in conventional unipolar ECG system, has been eliminated to further reduce the number of electrode assemblies that must be placed on the patient in order to enable standard 12-lead ECG tracing. Instead, a common reference CCE has been incorporated within the structure of the single strip-patch device assembly. The reduction of the number of electrode assemblies can be achieved and made by using the strip-patch, on which multiple and all of the CCEs are mounted and integrated within its structure.

For the purpose to enable detection and diagnosis of standard 12-lead ECG, the precordial strip-patch device-system of the present invention is for use on a patient in an assembly that includes an elongated strip-patch with first and second surfaces. Six conductive contact elements (CCEs) identified as $V_1$ through $V_6$ are mounted in spaced apart positions along the length of said strip-patch device. In other embodiments, CCEs identified as LA, LL and RA can be mounted on the said strip-patch device. A reference CCE is carried by said strip-patch device for serving as a common reference for other CCEs. The CCEs are exposed on the first surface of said strip-patch device and are adapted to contact the patient's skin for detecting heart signals and other physiological signals from the patient when the precordial strip-patch assembly is placed on the chest's precordium area of the patient. Junction mean is carried in a single region by said strip-patch device and is electronically connected to other CCEs. One or more microchips are connecting among the CCEs for elaborating the detected signals, microprocessing the data, and transmitting on a single radio frequency wavelength an encoded signal which carries the heart signals detected by the CCEs, to the receiving-decoding-interface section that is connected to the recording/monitoring hardware.

The present invention further presents different configurations or groupings of CCEs or microsensors, which enable the detection, calculation and wireless transmission or otherwise telemetering of sensed or elaborated data in regard to cardiac output, respiration rate, peripheral blood oximetry and temperature, of a patient, as well as fetal heart monitoring. While an important reference has been made herein relating to detection, data processing, logic analysis and memory residence by microprocessors and semiconductors, encoding-decoding, wireless or single-wired or fiberoptic or otherwise transmission, telemetering and elaboration of 12-lead electrocardiography, it should be understood that each of the herein mentioned physiological parameters, such as cardiac output, respiration rate, peripheral blood oximetry, temperature and fetal heart monitoring, can be integrated into any and all portions of herein mentioned electronic and semiconductors operation, simultaneously, independently or in any combination thereof. It should be understood that with only minor changes in the circuitry and the proper operating conductive contact elements, microsensors, or power source, monitoring capabilities can vary, enhanced or used in alternate or simultaneous fashion or groupings.

In one embodiment of the present invention, while maintaining electrical connection among all and any CEEs and the chip set structure and operation, said strip-patch contains, in addition to the CEEs that are suitable for standard 12-lead ECG, other additional CEEs to enable measurement of thoracic impedance and calculations of derivatives thereof which result in obtaining continuously cardiac output values.

In other possible configuration for the purpose of measuring cardiac output, some of the CCEs that already exist and serve for standard 12-lead ECG detection, can also be used for; the detection and measurements of the thoracic impedance and calculation of relating derivatives thereof; for fetal heart monitoring; for respiration rate measurements; and, for temperature measurement; Any combination thereof, in order to reduce the number of additionally needed CCEs or microsensors, is feasible.

In other embodiment of the present invention said strip-patch mentioned herein incorporates, in addition to the ECG's CCEs, additional CCEs spaced apart and mounted on within the structure of the strip-patch and electrically connected to the chip structure and operation mentioned herein.

In other embodiment of the present invention said mentioned herein strip-patch incorporates additional CCEs spaced apart and mounted on the strip-patch and electrically connected to the chip structure and operation, which enable the measurement and transmission of respiration rate.

In other embodiment of the present inventions said herein mentioned strip-patch contains also microsensor module and CCEs that enables measurement of peripheral blood oximetry (oxygen concentration) by means of hemoglobin (Hg) spectrum analysis of oxygenated hemoglobin versus non-oxygenated hemoglobin at the capillary bed.

In other embodiment of the present invention an additional CCE and microsensor is mounted on the herein mentioned strip-patch and enable the measurement of the temperature of a patient, while electrically connected to the herein mentioned chip structure and operation.

In other embodiment of the present invention an additional microprocessor is mounted on the herein mentioned strip-patch, having the appropriate software and scientific data to enable elaboration and evaluation by data by artificial intelligence decision making capabilities "on-patient".

In other embodiment of the present invention additional one or more microchips are mounted on or linked to the herein mentioned monitoring strip-patch, which allow automated or by-demand cellular or wired telephone communication capabilities.

In other embodiment of the present invention appropriate and variable positioning of CCEs allow the continuous detection and diagnosis of an electrocardiogram of a pregnant woman simultaneously with detection capabilities of her fetus heart rate, and transmission means thereof to a beeper-size alert device or to recording or display monitoring hardware.

It should be understood that each of the CCEs groupings or settings can detect one or more physiological parameters, sharing all and any of the microchip set capabilities for data processing, logic analysis and memory resident processing, calculations, control, triggering, encoding, transmission or other software or electronic elaborations.

The present invention further present a single device system and method which incorporates cellular or wired communication means and such interfacing capabilities to allow better and faster access of a patient to medical help.

The present invention represents a single device-system in which one or more variable combinations mentioned herein for simultaneously and continuously monitoring of multiple physiological parameters, are feasible and possible, and could possibly become a milestone in patient monitoring and care.

BRIEF DESCRIPTION OF THE DRAWINGS

This invention and its advances over prior art can best be understood by reading the Specification which follows in conjunction with the drawing enclosed herein, of which:

FIG. 1A is a graphical representation of the distribution of additional electrodes in the system of FIG. 1.

FIG. 4 is a schematic diagram of an alternative circuit for developing a right leg signal.

FIG. 5 is an elevational view of the concentric electrode of FIG. 2.

FIG. 6 is an elevational view of an alternative form of a dipole electrode structure.

FIG. 7 is a block diagram of an electrode transmitter means with provision to switch the enabler code and the transmitter frequency.

FIG. 14 is a side elevational view of another embodiment of a dipole electrode structure, similar to the dipole electrode structure shown in FIG. 6 of the present invention.

FIG. 15 is a top plan view of a portion of the dipole electrode structure shown in FIG. 14.

FIG. 16 is a side elevational view of a portion of the dipole electrode structure shown in FIG. 14.

FIG. 17 is a view of an embodiment of a precordial strip assembly for electrocardiographic monitoring placed on the precordium area of a patient, together with a block diagram of a wireless electrocardiographic monitoring system (WEMS).

FIG. 20 is a diagram of a portion of the wireless electrocardiograph monitoring system shown in FIG. 17.

FIG. 21 is a more detailed diagram of a wireless electrocardiograph monitoring system (WEMS).

FIG. 22 is a top plan view of another embodiment of a precordial strip assembly, similar to the embodiment shown in FIG. 18, incorporating the present invention.

FIG. 23 is a top plan view of another embodiment of a precordial strip assembly, similar to the embodiment shown in FIG. 18, incorporating the present invention.

FIG. 24 is a view of another embodiment of a precordial strip assembly for electrocardiographic monitoring placed on the precordium area of a patient, together with a block diagram of a portion of a wireless electrocardiographic monitoring system (WEMS).

FIG. 25 is a top plan view of another embodiment of a precordial strip incorporating the present invention.

FIG. 26 is a top plan view of another embodiment of a precordial strip, incorporating the present invention.

FIG. 27 is a top plan view of yet another embodiment of a precordial strip, incorporating the present invention.

DETAILED DESCRIPTION OF THE PREFERRED EMBODIMENTS

In electrophysiology, the terms "unipolar" and "bipolar" are used in the traditional electrocardiographic sense, that is denoting measurements between electrode pairs relating to the appropriate limbs and having the conventional polarity, thereby yielding conventional electrocardiographic waveforms during cardiac excitation. The term "bipolar" recording, however, is used in this application in a novel way, and refers to the new method and electrode concept in which the single strip-patch device-system configuration, incorporates both a positive and a negative terminal (pole) within its structure, thereby obviating the need for an independent right leg grounding terminal as the reference point (reference electrode) as used in conventional 12-lead ECG systems. This strip-patch's device-system configuration enables recording of standard twelve-lead electrocardiograms. Therefore, the "bipolar electrode" concept is completely different from the traditional "bipolar recording" obtained from the limb leads of standard electrocardiography machines currently available for clinical use.

Figure 1:
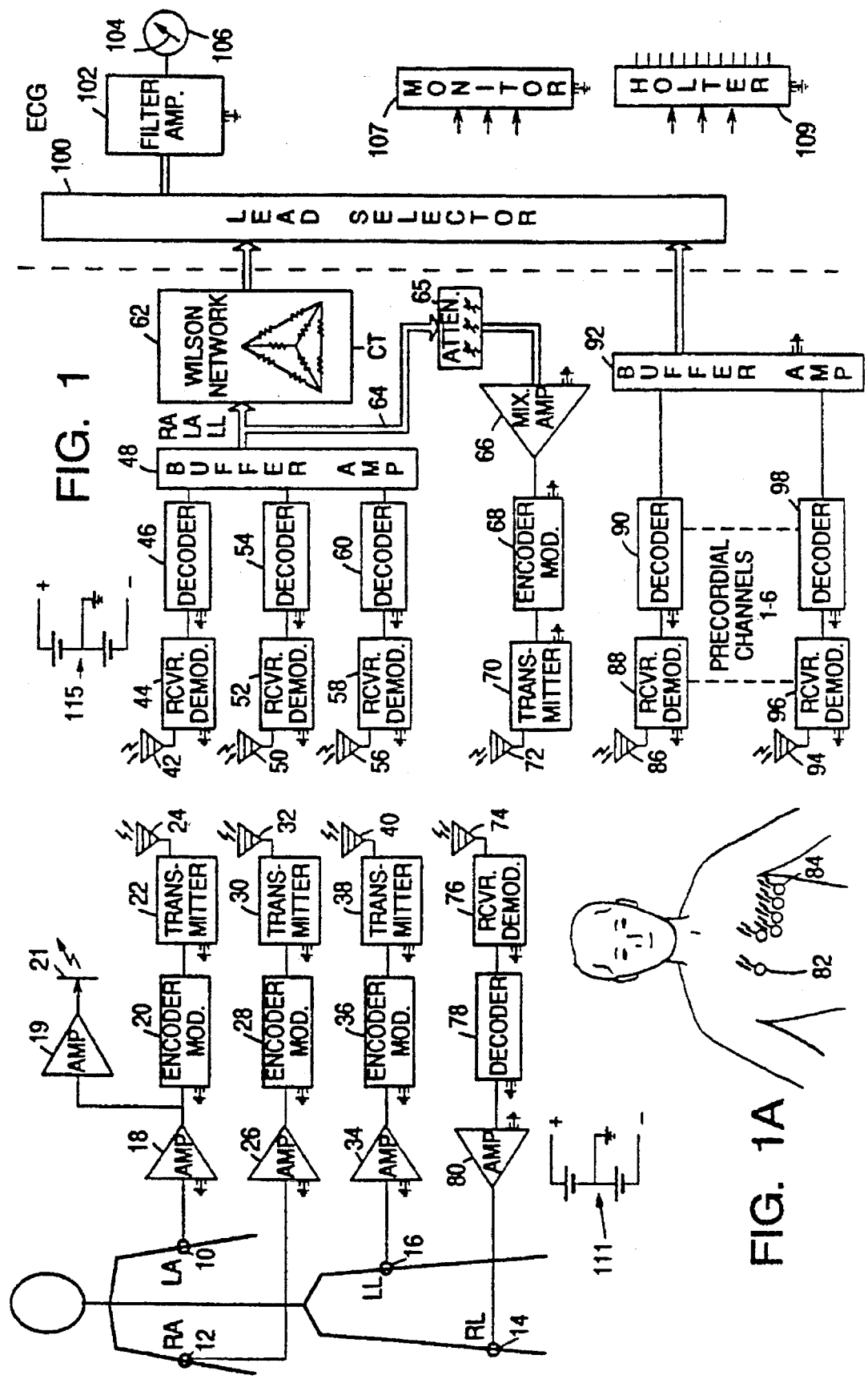
FIG. 1 is a block diagram of a wireless electrocardiograph system according to one embodiment of the present invention.

FIG. 1 shows a first embodiment of the present invention. In FIG. 1, the human body is represented by a stick Fig. to show the location of the limb electrodes of the system. Electrode 10 is connected to the left arm, electrode 12 is connected to the right arm, electrode 14 is connected to the right leg, and electrode 16 is connected to the left leg. Each of these electrodes requires two contactive surfaces which come into contact with the patient. They may be of either the concentric type shown in FIG. 2 or of the spaced-apart type of FIG. 6. In the FIG. 2 type, the outer conductive strip is used to establish a localized zero or reference potential, and the center connector is the source of signal for transmission or the point of application of the signal in the receiving mode. The outer ring may be referred to as an indifferent electrode of a localized nature. In the FIG. 6 type, one contact is the signal contact, and the other contact is the reference or indifferent electrode.

The output signal from electrode 10 is fed to amplifier 18 which feeds encoder-modulator 20. The signal thus derived is used to modulate transmitter 22 which is connected to antennae 24 from which the modulated RF signal is radiated. Amplifier 18 may comprise a microchip-type RC 4560 which has a dual-stage operational amplifier. Encoder-modulator 20 may comprise a CM 8555 IPA, or the equivalent, in combination with a 4OH393 chip. If digital encoding is utilized, a single transmitting frequency may be used for all transmitters. However, if analog modulation by the signal from electrode 10 is utilized, encoder-modulator 20 may act merely as a modulator, and each of the transmitters may be set at a different center frequency. Transmitter 22, and corresponding transmitters in other channels, may comprise a 930F5 microchip which includes a Colpitis oscillator. The audio frequency range which must be reproduced by the system is 0.05 hz to 125 Hz. The FM swing of the carrier frequency is typically no higher than 40 percent of the carrier frequency.

As shown, the output signal of amplifier 18 may also be fed through an additional amplifier 19 to an LED 21 which will give a light pulse each time a heart-signal is received at electrode 10. The heart-signal indicator may be provided at each electrode if desired.

The heart-signal from electrode 12 is fed to an amplifier 26 which, again, is a high gain, low noise amplifier, and the output signal of amplifier 26 is fed to encoder-modulator 28 and then to transmitter 30. The output signal of transmitter 38 is fed to antenna 32 for radiation.

The heart-signal from left leg electrode 16 is fed to amplifier 34, and the output signal of amplifier 34 is fed to encoder-modulator 36 for modulating FM transmitter 38. The output signal of transmitter 38 is fed to antennae 40 for radiation.

The signal radiated by antenna 24 is intercepted by antenna 42 and fed to receiver-demodulator 44, the output signal of which is fed to decoder 46 and then to buffer amplifier 48.

The signal from antenna 32 is intercepted by antenna 50 and fed to receiver-demodulator 52, the output signal of which is fed to decoder 54 and then to buffer amplifier 48.

Similarly, the signal from antenna 40 is received by antenna 56, and that signal is demodulated in receiver-demodulator 58 which feeds its output signal to decoder 60 for application to buffer amplifier bank 48. It should be understood that in buffer amplifier bank 48 there is a series of amplifiers, one for each transmitting limb signal channel. The signals from buffer amplifier 48 are fed to what is known as a "Wilson" network. This is essentially a bridge, the make up of which can be seen in FIG. 3. The left arm, right arm, and left leg signals are coupled to the "Wilson" network to produce what is known as an indifferent or reference potential which appears at the central terminal (CT). In this embodiment the signal at CT is not used, but it is used in the embodiment of FIG. 4. Instead, here, the right arm, left arm, and left leg signals are fed to a balancing attenuator 65 (three independently variable impedance paths) and then to a mixer amplifier 66 where the mixed signal is amplified by an internal low noise, high gain amplifier. The output signal of mixer amplifier 66 is applied to encoder-modulator 68 to generate the signal to modulate transmitter 70 which is coupled to antenna 72 for radiation by antenna 72. The radiated reference signal is picked up by receiving antenna 74, such antenna being coupled to receiver-demodulator 76 which develops a signal in the audible or sub-audible frequency range. Such signal, if it is encoded, may then be decoded by decoder 78, and the resulting signal may be applied to amplifier 80 which is coupled to the active contact of electrode 14 carried by the right leg. This establishes the so-called zero potential on the indifferent or reference electrode 14. Such a zero signal can be used for operation of system involving the use of unipolar limb leads. The signals from the same electrodes are used to produce the bipolar limb leads previously described.

Figure 12A:
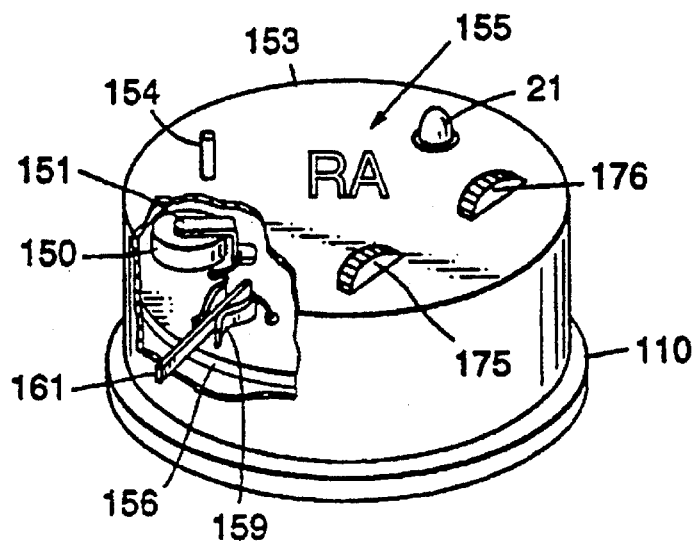
FIG. 12A is a partial cut-away perspective view of a transmitter/electrode assembly of the present invention.
Figure 12B:
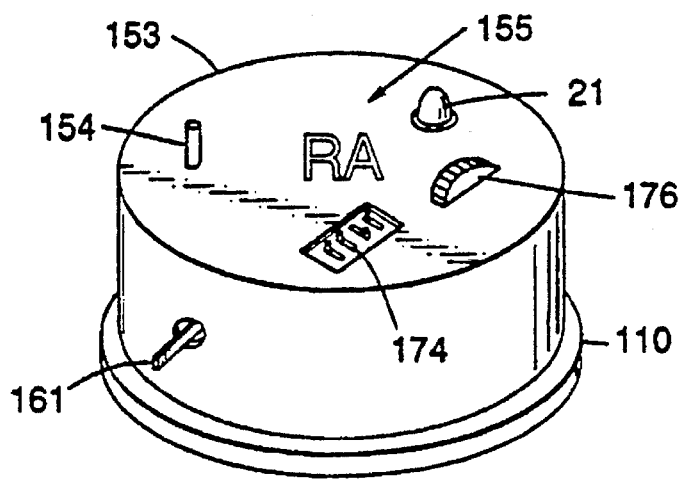
FIG. 12B is a perspective view of a transmitter/electrode assembly of the present invention.

The transmitters in the system, if purely analog techniques are involved, may be set at center frequencies of, for example, 72.080 MHz and at multiples of 160 KHz around that center frequency. Since the transmitters operate simultaneously with 160 KHz separation between their center frequencies there is no problem with intermodulation at the respective receivers, each of which has a corresponding detector center frequency so that the proper received signal is acted upon. Operation at much higher frequencies, for example, in the 400 MHz band, results in a much shorter antenna requirement but increases power requirements, thus putting a heavier load on the very small battery which can be mounted with the microchips in connection with the electrodes utilized in the system, as shown in FIGS. 5, 12A, and 12B. This analysis applies equally to electrodes used to detect signals for unipolar or bipolar leads. With a digitally encoded system, the center frequency may also be changed between systems to reduce the possibility of interference between systems operating in close proximity to each other.

As for the heart-signals at the precordial electrodes, such as electrode 82 and electrode 84, the transmitters are as shown in connection with the limb signal transmitters just described. Again, the frequencies are set differently, each from the other, but at higher frequencies; this is not a problem. Also, because the field strength of the signals from the various electrodes associated with transmitters is low, there is considerable freedom in choosing a frequency which is free of local interference. There are generally six precordial electrodes, and, therefore, in this system there are six precordial channels (for simplicity, only the first and sixth are shown in FIG. 1; however, each channel not shown is similar to those shown), each having the transmitting and receiving structures of corresponding elements in the limb signal channels. For example, the signal from the first precordial electrode 82 and its associated transmitter is received by antenna 86 and is fed to receiver-demodulator 88 where a signal in the audible or subaudible frequency range is obtained and fed to decoder 90 for any decoding that is necessary to reproduce the heart-signal. The heart-signal thus derived is applied to the buffer amplifier bank 92. Similarly, the heart-signal detected at the sixth precordial electrode 84 is transmitted by the associated transmitter and is received by antenna 94, following which it is detected and demodulated by receiver-demodulator 96, and, if necessary, it is then decoded by decoder 98 and fed to buffer amplifier 92. Buffer amplifier 92 is a bank of amplifiers, one for each of the six precordial signal channels. The limb signals and the precordial signals are fed, without loss of integrity, to lead selector 100 which is of the conventional type found in commercially available electrocardiographs and which permit selection of each of the channels individually. The output signals of lead selector 100 are fed to filter-amplifier 102, following which the signals are fed to the electrocardiographic analog or digital cardiographic display. The analog recording pens are represented by needle 104. The galvanometric mechanism is represented by element 106. Alternately, selected ones of the signals shown entering lead selector 100 may be fed directly to a monitor 107 or to a Holter system 109 for developing a twelve-lead electrocardiogram from the signals sensed by the electrodes placed only on the chest area.

Figure 2:
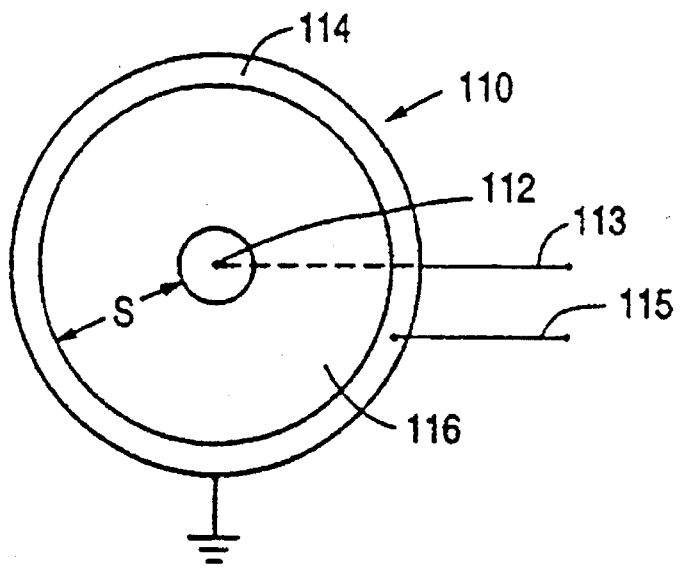
FIG. 2 is a schematic diagram of a concentric dipole electrode for use in the present invention.

Turning to FIG. 2, there is shown one dipole electrode patch configuration for use with the present invention.

Electrode patch 110 includes signal contact element 112 that is electrically conductive in nature and has a conductor 113 associated therewith for coupling, for example, to the microchip amplifier, the encoder-modulator, the transmitter element of FIG. 1, or to external equipment. Contact 112 may be made of aluminum, for example. Contact 114 is the indifferent or reference contact with the spacing "S" between contact 114 and contact 112 being typically 2–4 cm. Of course, concentric ring contact 114 is electrically conductive in nature. In some cases it may not be a closed circle but may merely be an arc of a circle. Contacts 112 and 114 are carried on an electrically non-conductive plastic film body 116, for example. If contacts 114 and 112 are too widely separated, the accuracy of the graphic reproduction of the heart-signal will be diminished.

Figure 3:
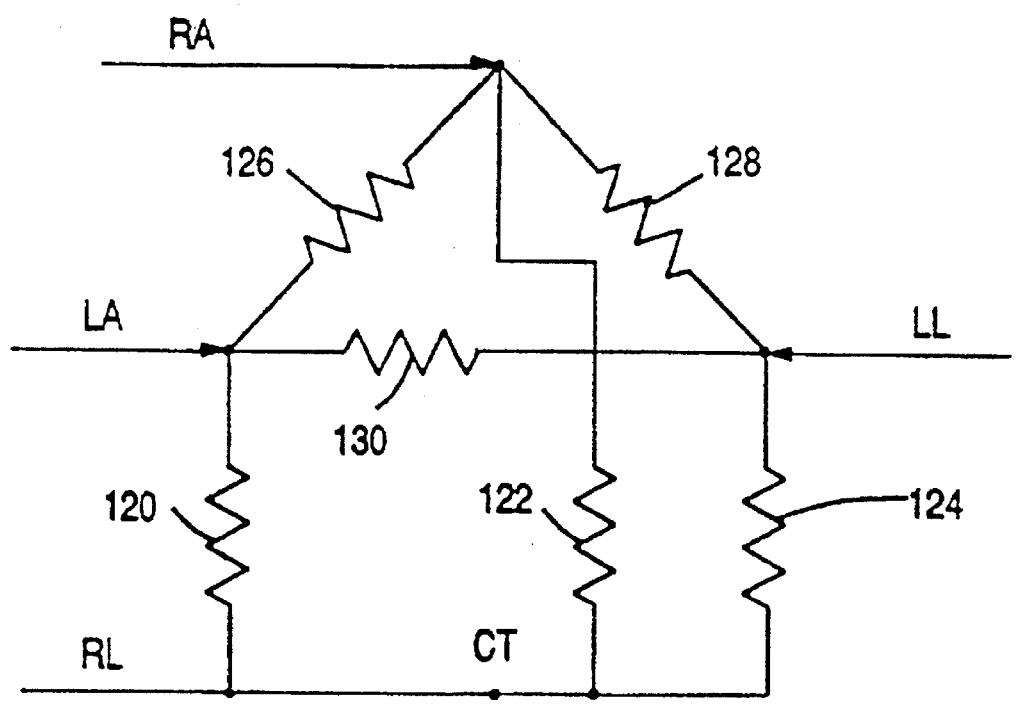
FIG. 3 is schematic diagram of a "Wilson" network or bridge for developing an indifferent signal.

In FIG. 3, the so-called "Wilson" network is shown. The purpose of this network is to establish a zero area of the field from the heart dipole which is creating the field being studied. As can be seen from FIG. 3, the right arm, left arm, and left leg potentials are combined through three equal resistors 120, 122, and 124 to establish a zero or reference point which is generally referred to as the central terminal. The size of each of resistors 120, 122, and 124 is in excess of 5,000 ohms with the general range being 5,000–15,000 ohms. The CT potential is not actually zero. Theoretically, the potential of the CT is the mid-dipole potential of the heart-signal generator if the field is homogenous and if the dipole generating the signal lies exactly in the center of an equilateral triangle, the angles of which are formed by the three electrode points LA, RA and LL. Resistors 126, 128 and 130 have the same resistance and form an electrical equilateral triangle simulating the Einthoven triangle of the electrocardiographic art.

According to the embodiment of FIG. 4, the CT potential, after amplification by amplifier 129, is transmitted by transmitter 70 through antenna 72 to receiver-demodulator 76 and its associated components for application to the right leg electrode 14, shown in FIG. 1.

Unipolar leads are presently the only ones used in the precordial positions, such as in FIG. 1A. It was formerly believed that a limb could serve as the indifferent or reference connection because it was relatively so distant from the precordial electrode. It soon became apparent, however, that this was not the case, that the arm or leg was not truly indifferent, and that it altered the results in varying degrees depending upon which limb was connected to the negative terminal of the electrocardiograph. Thus, there was a need to establish a central terminal, as described hereinbefore.

Associated with each of the limb and precordial electrodes is a power supply III (conventionally a battery) which provides to the microchips operating a voltage of necessary polarity and magnitude. At the base station side, integrated circuit (IC) operating voltage of the necessary polarity and magnitude is provided by power supply 115 which may be battery or AC based.

From FIGS. 5, 12A, and 12B, it is apparent that each electrode patch 110 carries its own power supply 150 as well as the necessary Microchips 152, which are powered by power supply 150, and an antenna 154. An LED 21 may also be provided which lights with each heart beat. Tab 161 is an insulating member which, when pulled, connects power supply 150 to the microchips and activates the associated electrode assembly. This is true for the receiving electrode 14 on the right leg as well as for the various transmitting electrodes.

FIGS. 12A and 12B are perspective views of a typical electrode assembly of the present invention. They each show an electrode assembly housing 153 mounted on an electrode 110. On top of housing 153 there is shown an electrode position indicator 155; in these views the letters "PA" designate that this electrode assembly is for use of the right arm of the patient. Other means for identifying the electrode assemblies can be used, such as color coding. No matter what form of coding is used, each of those codes needs to be designed to minimize the possibility of error caused by installation of the electrodes in the wrong location on the patient.

Also shown in these Figs. is a frequency change switch 176 which could be a detented wheel type switch so that each frequency position is well defined and the operator will easily know which setting the frequency is in. Similarly, there is an encoding selector switch in either a detented wheel switch configuration shown as switch 175, or a DIP switch 174.

FIG. 12A is also partially cut away to show the printed circuit board 156 that is internal to the assembly with a battery 150 mounted to board 156 and making contact thereto via battery clip 151. Serially connected to battery clip 151 is a pair of electrically conductive spring fingers 159 which are mounted adjacent each other. Between fingers 159 is tab 161 which prevents contact of fingers 159 with each other. The combination of tab 161 and fingers 159 therefore act as an on/off switch which prevents battery 150 from discharging prior to use and allows the operator to very positively activate the electrode assembly by completely removing tab 161. If such an assembly is to be reused, tab 161 should be reinserted between fingers 159 to deactivate the circuitry.

FIG. 6 shows an alternative form of a dipole electrode structure 158 which is particularly useful for precordial application. The necessary separation of signal electrode 160 and zero reference electrode 162 is achieved in the limited space available on the chest. This strip electrode structure carries a microchip amplifier, an encoder-modulator, and a transmitter module 164 (with battery) and connectors 163, 165 for signal input.

Each dipole electrode structure 158 may have a multiple-position switch which changes the frequency or digital encoding of the signal from the electrode so that it matches the parameter for the site at which it is to be used on the patient in order to limit the number of electrodes with different operating parameters which must be kept in inventory and employed in setting up the system for a given patient.

The electrodes may be color coded or labeled to indicate where they should be placed on the body. They may also include frequency or code switches to permit one electrode type to be usable in various body locations.

Figure 11:
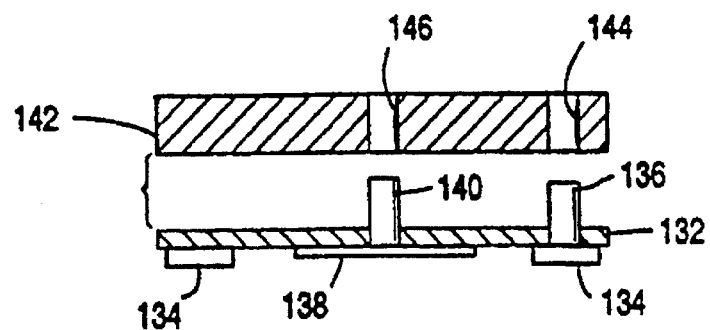
FIG. 11 is a cross-sectional side view of a snap mounting configuration for removably mounting a transmitter assembly to a disposable electrode.

FIG. 11 illustrates another form of electrode/electronics assembly that may be of interest in some applications. This assembly consists of two portions, an electrode assembly 132 that may be disposable, and an electronics assembly 142 that may be reusable. Electrode assembly 132 includes reference contact 134 and its associated connection position post that extends through the insulative body of the electrode to the side opposite the contact, and signal contact 138 and its connection post 140 that also extends through the body of the electrode. Electronics assembly 142 is sized and configured to mount onto electrode assembly 132 and to mate with connection posts 136 and 140 which are disposed to be received by contacts 144 and 146, respectively.

Each of the contacts 144 and 146 are spring loaded to make electrical contact with and to physically capture connection posts 136 and 140.

FIG. 7 illustrates in block form this capability. In FIG. 7, heart-signals from any of the ten electrodes are coupled to amplifier 170, as shown in FIG. 1. The output of amplifier 170 is fed to encoder-modulator 172 which includes a quad NAND gate section as is found, for example, in a type TSC-323 integrated circuit. DIP switch 174 permits selection of a three-digit code if digital encoding is used. On the other hand, if analog encoding is to be used, a frequency-change switch 176 is provided on transmitter 178. The oscillators described in connection with FIG. 1 (which are used here) are tunable by changing the applied voltage. Such voltage change is accomplished by using switch 176 to vary the voltage applied to the control line of a voltage controlled oscillator (VCO) that is a portion of the transmitter. Thus, by either method, the number of different types of electrodes that must be inventoried can be reduced. The base station decoders or receiver-demodulator may be fixed, and the electrode encoding means may be adjusted to correspond to the code or frequency of a target signal channel at the base station. A similarly equipped receiver-demodulator would also have to be provided to make similar adjustments either to the decoder or to the center frequency of the receiver.

The appropriately encoded signal, or the signal at the desired frequency, is fed to antenna 180.

This system is adapted to work with Holter systems in which twelve-lead electrocardiograms are derived from three-electrode information. This fact is illustrated by element 109 in FIG. 1.

The unipolar leads with respect to the right arm, left arm and left leg of the patient are traditionally measured with respect to the right leg as the reference point. With a system wherein each signal is individually transmitted to a base station, it is undesirable to run a wire from the right arm, left arm and left leg electrodes to the electrode attached to the right leg of the patient as a reference point. In the embodiment disclosed in FIG. 1, the reference point of the right left is created from the signals at the other extremities of the patient in the base station and then transmitted to the right leg electrode, as discussed above. This is the ten-electrode assembly approach. The right leg has historically been used as the reference point substantially because the earlier instrumentation lacked the sensitivity and the noise rejection capabilities of today's electronic devices.

After additional experimentation it has been determined that a reference point that is closer to the signal electrode than the right leg can be used, and that each of the three signals necessary to determine the bipolar leads I, II, and III, as well as the unipolar leads aVR, aVL and aVF and $V_1$ through $V_6$, can be measured with respect to different reference points without reconstructing a common reference point signal. Today's electronics requires that each of these reference points be a least 2–4 cm. From the corresponding signal contact. Electrodes such as those shown in FIGS. 2 and 6 could be used for this purpose, for viewing the shape of the electrocardiograph signals and their amplitude. The controlling factor is therefore the ability of the electronics to extract the needed signals from the background noise. This is practiced in the nine-electrode assembly approach.

Figure 8:
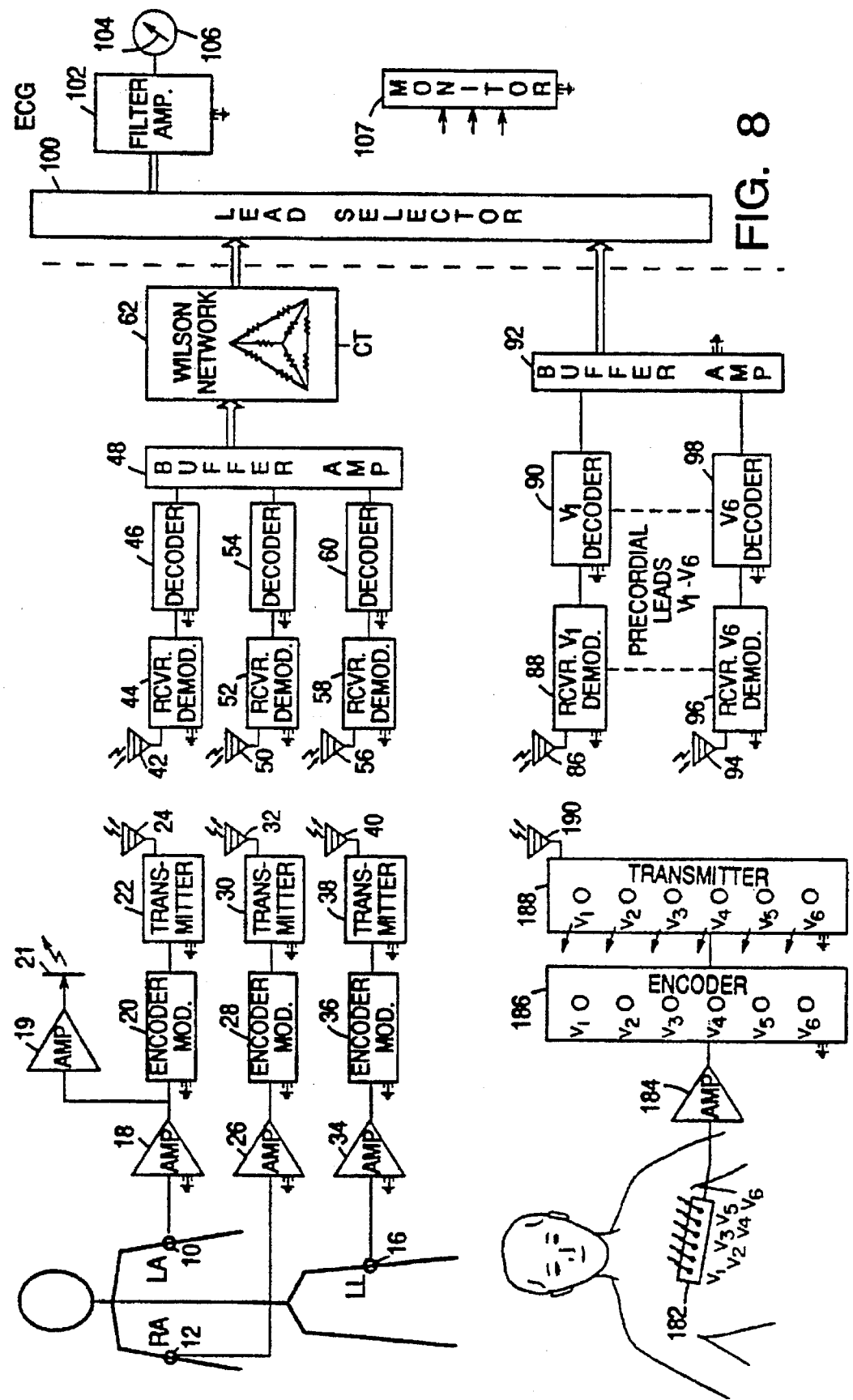
FIG. 8 is a block diagram of a wireless electrocardiograph system according to a second embodiment of the present invention.

Therefore, a second embodiment of the present invention is a system as shown in FIG. 8 which does not have the receiving and transmitting paths associated with the reference electrode positioned on the right leg of the patient, as shown in FIG. 1.

Figure 10A:
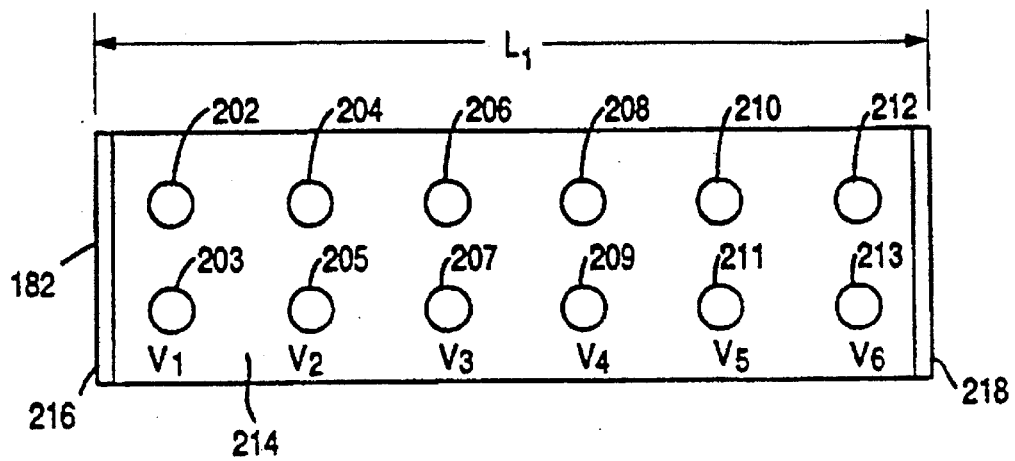
FIG. 10A is a plan view of the electrical contact side of an electrode strip of one configuration for the six precordial electrodes for easy mounting on the chest of the patient.

In a continuing effort to make the wireless ECG system of the present invention even more foolproof, a precordial dipole electrode strip 182 has been designed. (See FIGS. 8 and 10A.) Strip 182 includes a pair of contacts 202–213 (signal contact are even numbered, and reference contacts are odd numbered) for each precordial signal measurement. Each of the contacts 202–213 (signal contacts are even numbered, and reference contacts are odd numbered) for each precordial signal measurement. Each of the contacts 202–213 is mounted or aligned on one side of strip 182 in a line or row in a spaced-apart relationship to the other contact mounted or aligned on the other side of strip 182 in another line or row and each of the contacts 202–213 has a connecting post, or the like, that extends through strip 182 to the opposite side. Precordial transmitter assemblies are mounted to the other side of strip 182 and electrically connected to the appropriate connecting post. The precordial electrodes are to be located on the body of the patient, evenly spaced, with the first being approximately 1 cm. to the left of the patient's sternum, and the sixth approaching the patient's side. To accomplish this, various lengths of precordial electrode strips 182 could be manufactured. Alternatively, the base material of strip 182 could be elastic, similar to an elastic bandage. To hold strip 182 to the chest of the patient, adhesive areas 216 and 218 can be provided at either end of strip 182. Alternately, the entire contact side 214 of strip 182 can be coated with an adhesive other than on the faces of the twelve contacts. This is the four-electrode assembly approach.

Figure 9:
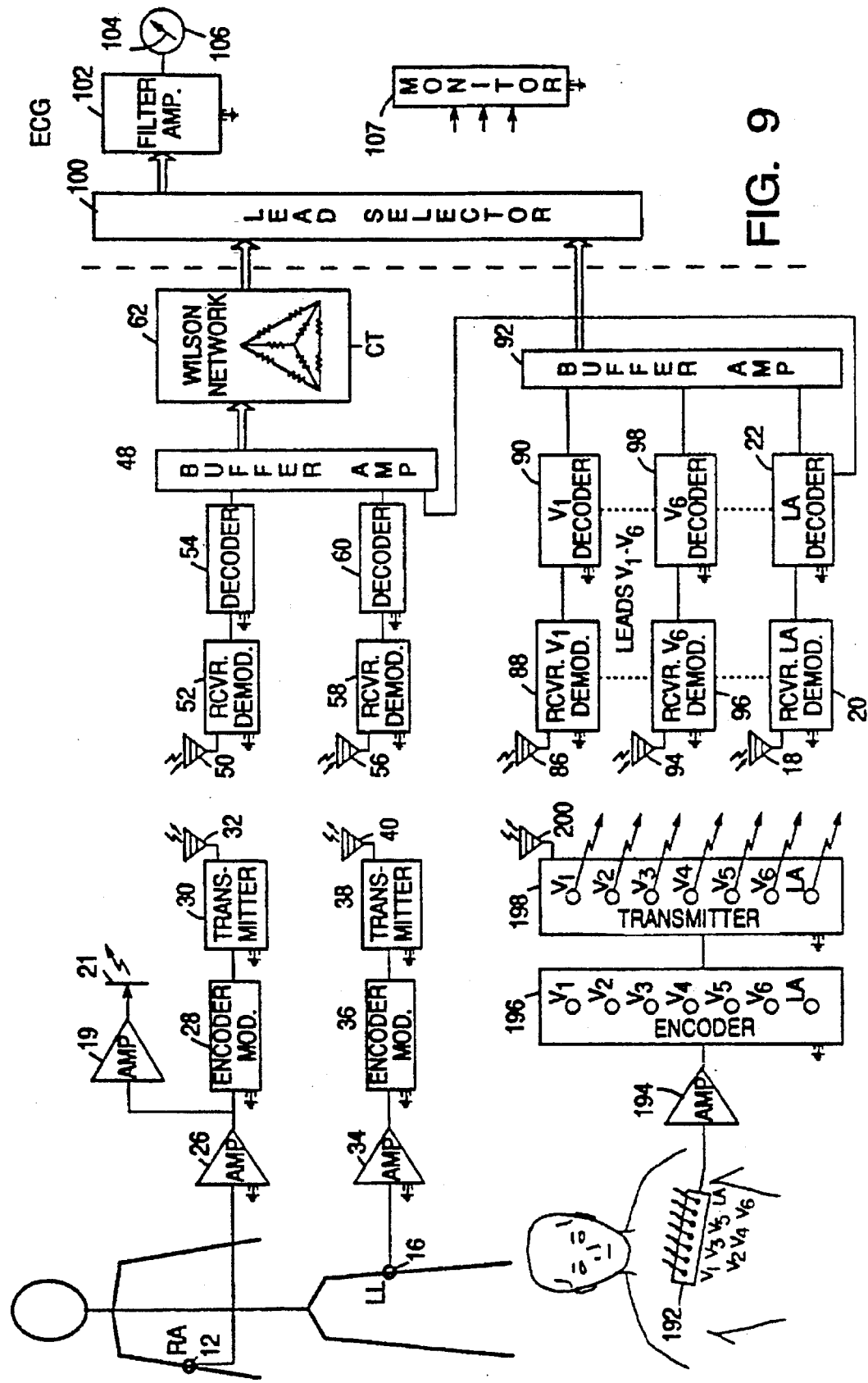
FIG. 9 is a block diagram of a wireless electrocardiograph system according to a third embodiment of the present invention.
Figure 10B:
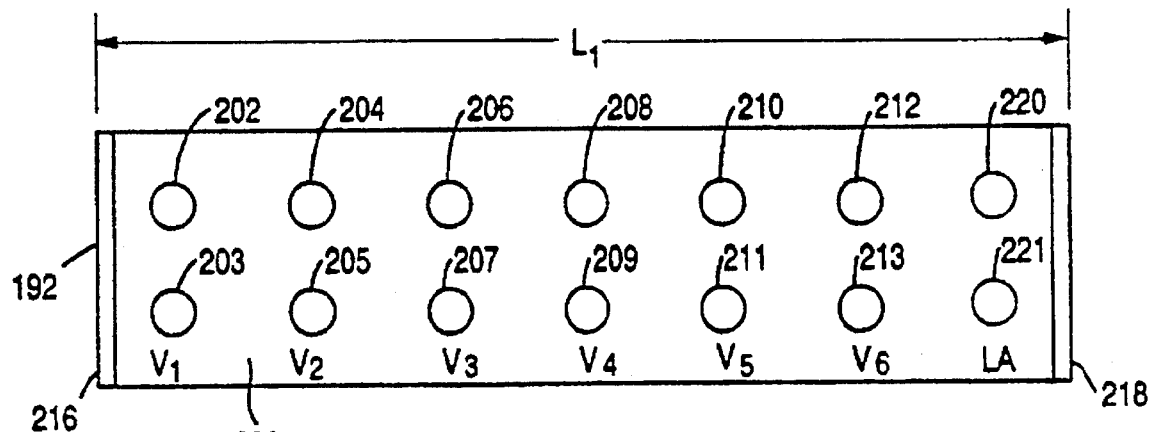
FIG. 10B is a plan view of the electrical contact side of an electrode strip of a second configuration for the six precordial electrodes and the left side electrode for easy mounting on the chest of the patient.

Additional experimentation has shown that the left arm dipole electrode can be moved to the left side of the patient with no loss in accuracy of the resulting ECG data. As a result of this experimentation another embodiment of the present invention is the lengthening of the precordial dipole electrode chest strip of FIG. 10A to include a pair of contacts 220 and 221 to monitor the left arm signal at the left side of the patient. The extended strip 192 is shown in FIG. 10B, and the corresponding electronics is shown in FIG. 9. This is the three-electrode assembly approach.

In either of the embodiments of FIGS. 8 and 9 the transmitting assemblies attached to strip 182 or strip 192 may be individual units that are attached to the appropriate connection posts of the various electrodes, or they may be individual transmitters which are all contained within a common housing. The transmitting assemblies in FIGS. 8 and 9 include encoders and transmitters 186 and 188 or 196 and 198, respectively.

Reference to only a wireless ECG has been made up to this point in this Specification. However, the wireless transmission of signals from a patient, regardless of the function being monitored, can be transmitted and received remotely in the same way. Thus, a truly wireless monitoring system that includes pulse, temperature, etc. can be easily accomplished with the transmitting and receiving devices of the present invention.

Figure 13:
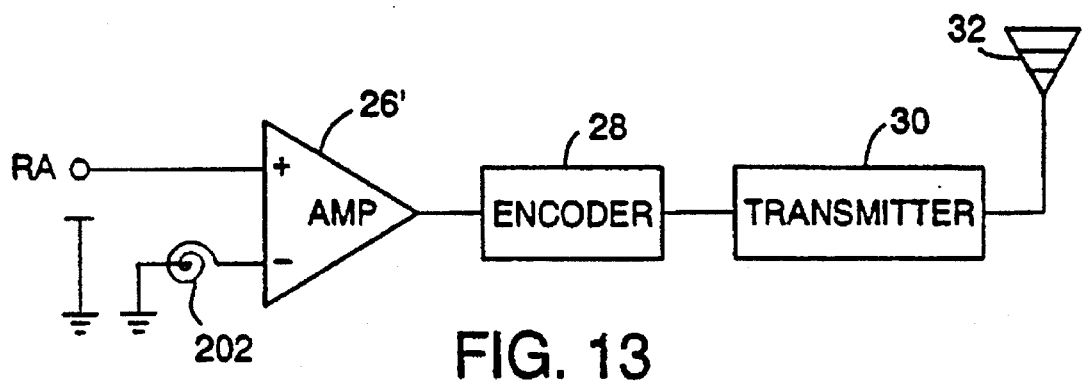
FIG. 13 is a block diagram of circuitry used in the apparatus.

To further improve the possibility of the dipole electrode assemblies to separate the desired signal from the background noise, amplifiers such as 26 and 34 can be differential input amplifiers as shown in FIG. 13. Differential input amplifier 26' includes two signal input terminals—an inverting terminal and a non-inverting terminal. The signal from the right arm dipole electrode is connected to the non-inverting terminal, and a noise pick-up coil 202 is connected to the inverting terminal. The purpose of noise pick-up coil 202 is to detect the background noise and to apply that to amplifier 26'. The theory is to subtract or reduce the background noise from the signal that is included with the signal from the right arm dipole electrode. This is accomplished by the difference in sign of the two input terminals of amplifier 26' since the output signal from amplifier 26' is the arithmetic difference between the two input signals that have been amplified by a selected factor. Thus, including this type of amplifier in each of the transmitter assemblies will largely reduce the signal noise and permit the use of less sensitive components or will allow the use of dipole electrode patches that have a smaller spacing between their signal and reference contacts.

FIG. 14 is another embodiment of dipole electrode structure 158 illustrated in FIG. 6 which includes a detachable microchip 230 to permit reuse thereof. Structure 158 includes a non-conductive layer of plastic material 231 with signal electrode 160, reference electrode 162 and a chip receptacle 232 mounted thereon. Structure 158 further includes connectors 163 and 165 which electrically connect and couple electrodes 160 and 162 to chip receptacle 232. Chip receptacle 232 is provided with a plurality of sockets 233, four of which are represented in FIG. 15.

Microchip 230 has electronic components substantially similar to those contained in microchip 164, including an amplifier, an encoder-modulator and a transmitter, and can be snapped on and off of structure 158. To facilitate its attachment and removal from structure 158, microchip 230 has a plurality of prongs or pins 234, four of which are represented in FIG. 16. Prongs 234 cooperatively mate with sockets 233, as shown in FIG. 14, when microchip 230 is attached to chip receptacle 232.

Figure 15A:
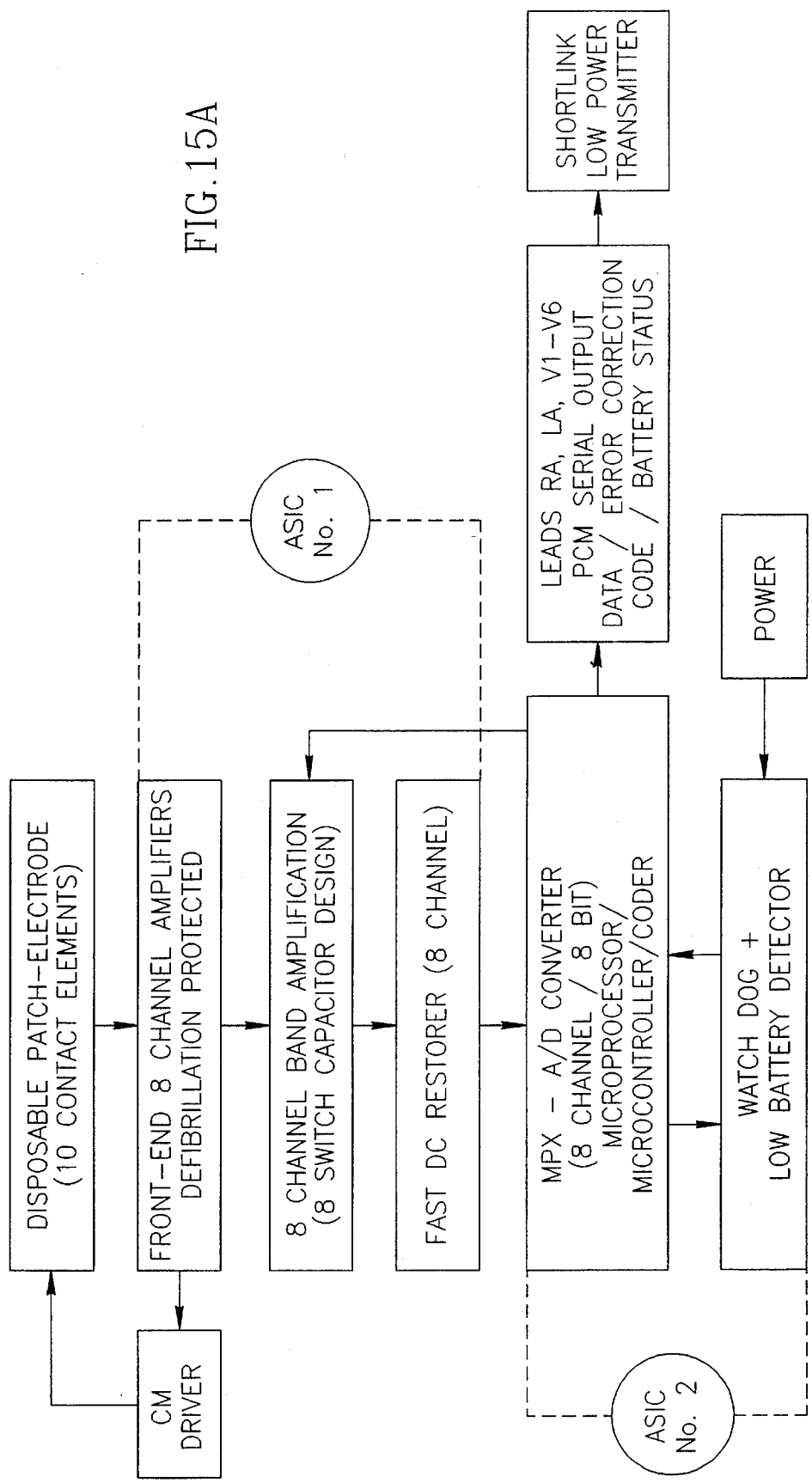
FIG. 15A is a detailed block diagram of the Section A in Wireless Electrocardiographic Monitoring System (WEMS).
Figure 16A:
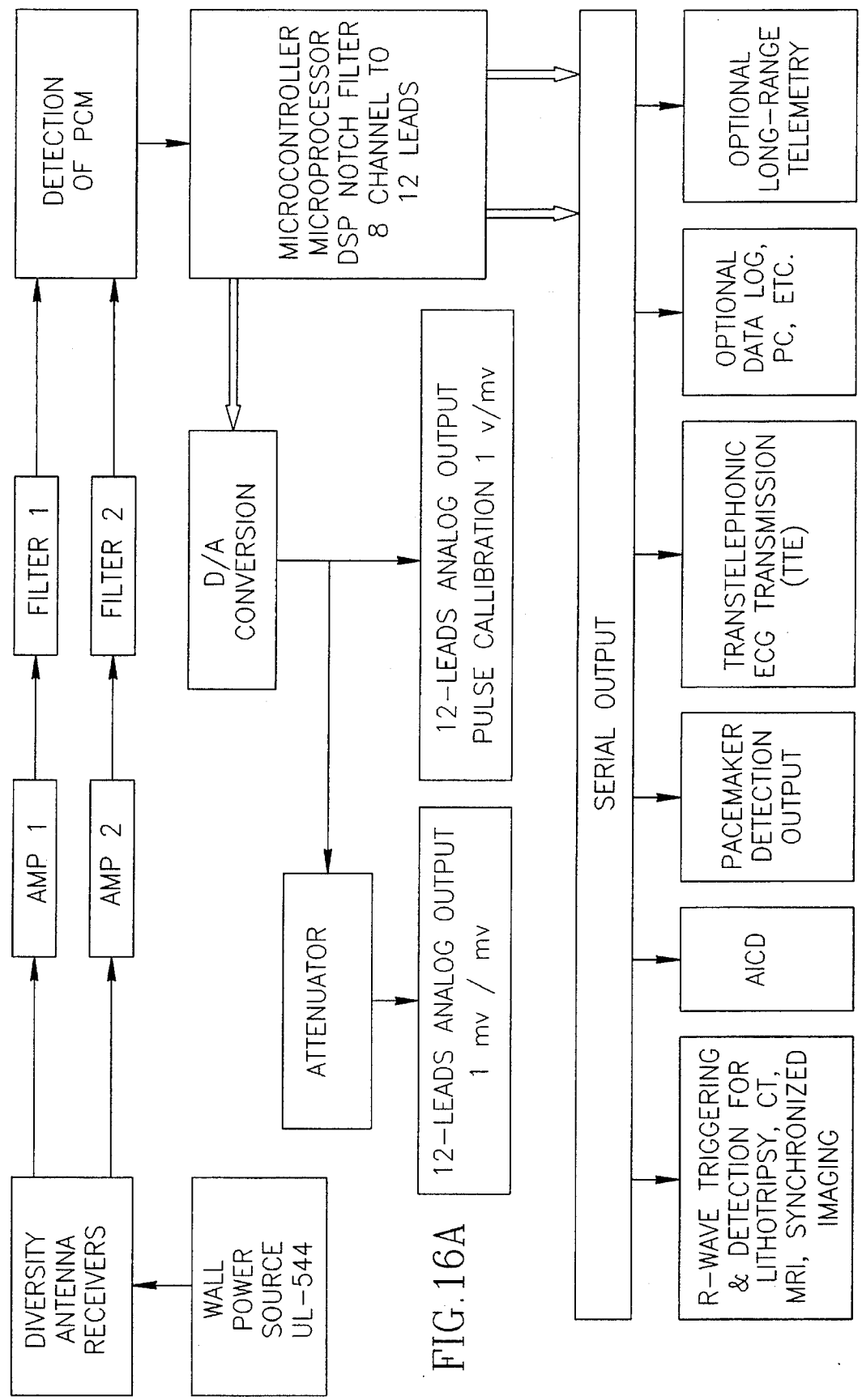
FIG. 16A is a detailed block diagram of Section B in the wireless electrocardiographic monitoring system (WEMS).

As illustrated in FIG. 15A and 16A, a Wireless Electrocardiographic Monitoring System (WEMS) enables wireless continuous detection and diagnosis of standard 12-lead ECG between the patient and the recording/display ECG monitoring hardware, with a single electrode-system. The WEMS consists of two sections: Section A, that can possibly be a single-use (disposable) part, is the patient's end strip-patch device-system, and Section B (reusable) is the receiving-decoding section end of said device-system which interfaces to existing recording or display ECG monitoring hardware.

FIG. 15A details the operation of Section A—the patient's strip-patch electrode-system: said strip-patch electrode-system (SPES) is placed on the patient's chest to detect the electrical signals of the heart, elaborates the signals into standard 12-lead ECG according to normal electrophysiological parameters, digitally encodes the information and digitally transmits it on a single transmission wavelength channel by Pulsed Coded Modulation (PCM) to Section B (the receiving-decoding and interface-to hardware). The transmission of all of the 12 leads of the electrocardiogram occurs sequentially, continuously and simultaneously, thus, the ECG's 12 leads are presented at the same time in Section B, therefore, it appears as 12-lead ECG at the same time on the ECG recorder-chart/display-screen, and not single-lead after single-lead (unless the printing hardware is limited to print one lead at a time). Section A is self-powered and self-contains two ASIC components. It consists of an elongated strip-patch having, for standard 12-lead ECG detection, 10 Conductive Contact Elements (CCEs) that are in direct contact with the patient's skin when placed on the precordial (center-left of the patient's chest) area. For simultaneous monitoring cardiac output, respiration rate, peripheral blood oximetry and temperature and fetal heart monitoring, more CCEs, microsensors and ASICs would be integrated within/on said strip-patch device system.

For standard 12-lead ECG, the strip-patch's ten CCEs connect to 8 front-end amplifiers (RA, LA, $V_1$, $V_2$, $V_3$, $V_4$, $V_5$, $V_6$) and to additional two electrical references (LL, RL) as reference circuit interfaces to Common Mode (CM) driver. The 8 channel band amplification is of 8 switch capacitor design. Since the WEMS device-system of the present invention targets diagnostic ECG, the device-system contains also white (wide) band filters on the other hand, in Section B—in the receiving-interface section, for final stage filtering performance which allows selection between diagnostic ECG bandwidth (0.05–100 Hz) or ECG monitoring bandwidth (0.5–40 Hz). It connects to fast DC restorer (8 channel) that keeps a baseline restoration and stabilizes the ECG baseline. The ECG amplifiers and the reference circuit constitute one chip. It is defibrillator protected to prevent damage to the strip-patch's electronics if an electrical shock is given to the patient during cardiopulmonary resuscitation (CPR). The first chip is fully custom analog-to-digital. It also contains a portion of a "watch-dog" element that automatically resets the software and keeps it from entering into a "loop" or hang-up as a result of using an electrical instrument that may be in contact with the patient's skin (i.e., electrical coagulation during surgery). The "watch dog" is divided into two sections between the two chips in order to prevent placing it entirely in the microcontroller of which it actually supervises. The second chip contains a multiplexer analog-to-digital (8 channels/8 bit or 12 bits or 16 bits or 18 bits) converter that has serial output of leads RA, LA, $V_1$–$V_6$ with data/error correction code, low battery status flag and integrity check codes. The second chip (probably of Motorola) connects to a microprocessor/microcontroller having CPU, RAM and encoder and carries proprietary ROM under silicon mask which prevents non-authorized access and, enables control of Electrically Erasable Programmable Read Only Memory (EEPROM) log into the memory of a specific patient code. This feature is a Non-Volatile Memory Option (NVMO) that does not require power source to retain the memory. The second chip connects to a transmitter that contains a frequency selection element for multi patients' use (frequency channels are authorized by the FCC and each system operates on its own exclusive single frequency channel). The transmission is short-link low-power Pulsed Coded Modulation (PCM). The power source to operate the entire patient's strip-patch device-electrode-system is housed within the transmitter element. Zinc-air battery can be used. Zinc-air batteries have high energy contents. It has the highest capacity versus weight, i.e., 500 mA/hour is a battery that weights approximately 1 gram (1/30 ounce) and a 500 mA per-hour battery will last continuously for over three days. The zinc-air is more environmental friendly then lithium, and is considered to be safe during flights vs. lithium that could explode during flight and may require authorization to be carried on board of an airplane. Another advantage of zinc-air powered system will be the way batteries are replenished; no longer will these batteries have to go through the lengthy process of recharging or replacement; instead, the zinc-air battery cells (the anode part of the battery; air is the cathode) can be pulled out and regenerated with electricity that turns the zinc oxide left in the cell back into zinc. This process is not dangerous and does not produce corrosive by-products; zinc oxide actually is used in cream for babies" skin. However, because of the relatively high drainage required by said strip-patch device-system, the zinc-air power source would need a set of three cells. A potential power source shut-off trigger, if necessary to be applied in some system variations, would allow the reuse of the system more then once (i.e. in doctor's office for more then a single STAT ECG recording), is feasible by closing off the air supply. The power source can also be a silver-zinc battery, or also use two lithium batteries (lithium battery is thinner than silver-zinc) at the same time; one lithium battery for the transmitter and the second lithium battery for the ASIC and the microprocessor. This would enable to prolong the time of operation of the strip-patch device-system since power drainage would not be from a single power source (a single battery cell). Another power source that can be used is thin lithium polymers which offer a flexible matter structure that can be easily incorporated within the device-system specifications, thereby including important design advantages for said device-system: flexibility, that improve adherence to the patient's skin, and wide surface area having a large storage capacity for power source. The above mentioned electronics results in two ASICs: ASIC number 1, of mixed analog/digital, contains the front-end amplifiers, CM driver, 8 channel band amplification with 8 switch capacitor design, and fast DC restorer; and ASIC number 2, containing a multiplexer, analog-to-digital (A/D) of 8 channels at 8 (or 12 or 16, or 18 bits) bits per-channel converter, microprocessor and/or microcontroller, coder, and "watch dog." the transmission between 19.2 kilobaud per-second up to about twice as much, is considered real-time in radio frequency transmission. In every sampling of data of 8 bits per-second the transmission contains 11 bits (8 bits for data, 1 bit to start, 1 bit to stop, and 1 bit for parity). For ECG purposes, the system can perform 250 samples per-channel per-second, therefore: 250 samples×8 channels×11 bits result in 22,000 bits per second, and with data compression, 19,200 bits per second are sufficient for transmission of 8 channels in 8 bits per second. It is possible to use 18 bits per-second, a fact that will reduce the cost of the analog portion (by having less filters), but the digital portion will need adaptive delta modulation of several ten-of-thousands bauds and signal compression. The ECG signal compression ratio can be of 10 to 1 (10:1) subject to the capabilities of the microcontroller (duration of the power source, drainage of power by speed, and relativity to the clock frequency). However, the transmission by 18 bits per-second is superior to 8 or 12 bits per-second since the ECG transmission includes all of the associated artifacts and its elaboration is performed at the receiver's end. In the case that 12 bits per second is used, the system can use 16 bits per-second (trade-off for 18 bits per-second) resulting in about 53 kilobaud, which is without compression since it is the standard baud rate in a synchronous serial communication. In cellular telephone communication the transmission is slower, of about 6,000 baud per-second, but the cellular telephone transmission of the detected and processed data can be delayed and does not need to be in real-time. At 100 megahertz transmission, the wave length is about 3 meters (9 feet) long, and the antenna for this wavelength transmission can be in the length of about 3 centimeters (1.25 of an inch). In a cellular telephone that operates at 900 megahertz transmission frequency or higher, the antenna will be very small and actually invisible. An advantage of the transmission in higher frequency is that it offers significantly reduced environmental interferences, however, it consumes more energy for transmission. The system can also use a single fiberoptic link that can connect between the strip-patch and the hardware-monitor or display, and in this case, there is no limitation in the speed of the data transmission.

FIG. 16 details the operation of Section B—the receiving and interface-to-hardware section: the wireless receiving-interface section operates with wall power source (comply with U.S. Safety Code UL-544) and not with battery source; thus, patient's safety factors do not apply anymore to this section since it is without contact to the patient. The receiving-interface section contains two antennas which connect to diversity antenna receivers. The transmitter, along with the encoded single wavelength having 12-lead ECG data, also transmits a calibration signal to the receiving-interface section. The two diversity antennas receivers connect to two amplifiers (one for each antenna) that connect to two filters which connect to a digital detector to enable identification and detection of the PCM transmission. The detector contains a microcontroller having error correction capabilities with DSP (Digital Signal Processing) for (1) notch filtering (selectable 50–60 Hz in the software) (2) error correction (3) reconstruction and computation of 12-lead ECG from 8 channels. The microcontroller connects to digital-to-analog converter which enables 12-lead analog output of 1 volt/mv with pulse calibration. The digital-to-analog (D/A) converter connects to an attenuator since upon recording with the attenuation the signal has to be divided by 1000 (signal/1000) and receive a signal identical to a one that is obtainable from direct physical contact to the human body, without gain (gain=1). On the other hand, the microcontroller has serial output and connects to optional long-range telemetry transmitter, optional data logger or PC, transtelephonic ECG transmitter (wired or cellular), automated implementable cardioverter defibrillator (AICD), pacemakers detection output, as well as R-wave triggering and detection for lithotripsy procedures, magnetic resonance imaging (MRI), computerized tomography (CT) and during synchronized imaging testing, automated management systems and integration of artificial intelligence.

Another embodiment of the present invention which enables transmission of 12-lead electrocardiogram on a digitally encoded radio frequency signal by means of a single frequency wavelength incorporating multiple detected signals, is illustrated in the drawings starting with FIG. 17. Precordial strip-patch assembly 321 of the present invention is for use on a patient 322 having a body 323 with a heart 324 and a precordium or precordium area 326 overlying heart 324. Body 323 is covered by an outer layer of skin 327. Patient 322 also has right and left arms 328 and 331 and right and left legs 332 and 333. Strip assembly 321 includes an elongate strip-patch or strip means 336 generally horizontal ("S" shaped in conformation.

Figure 18:
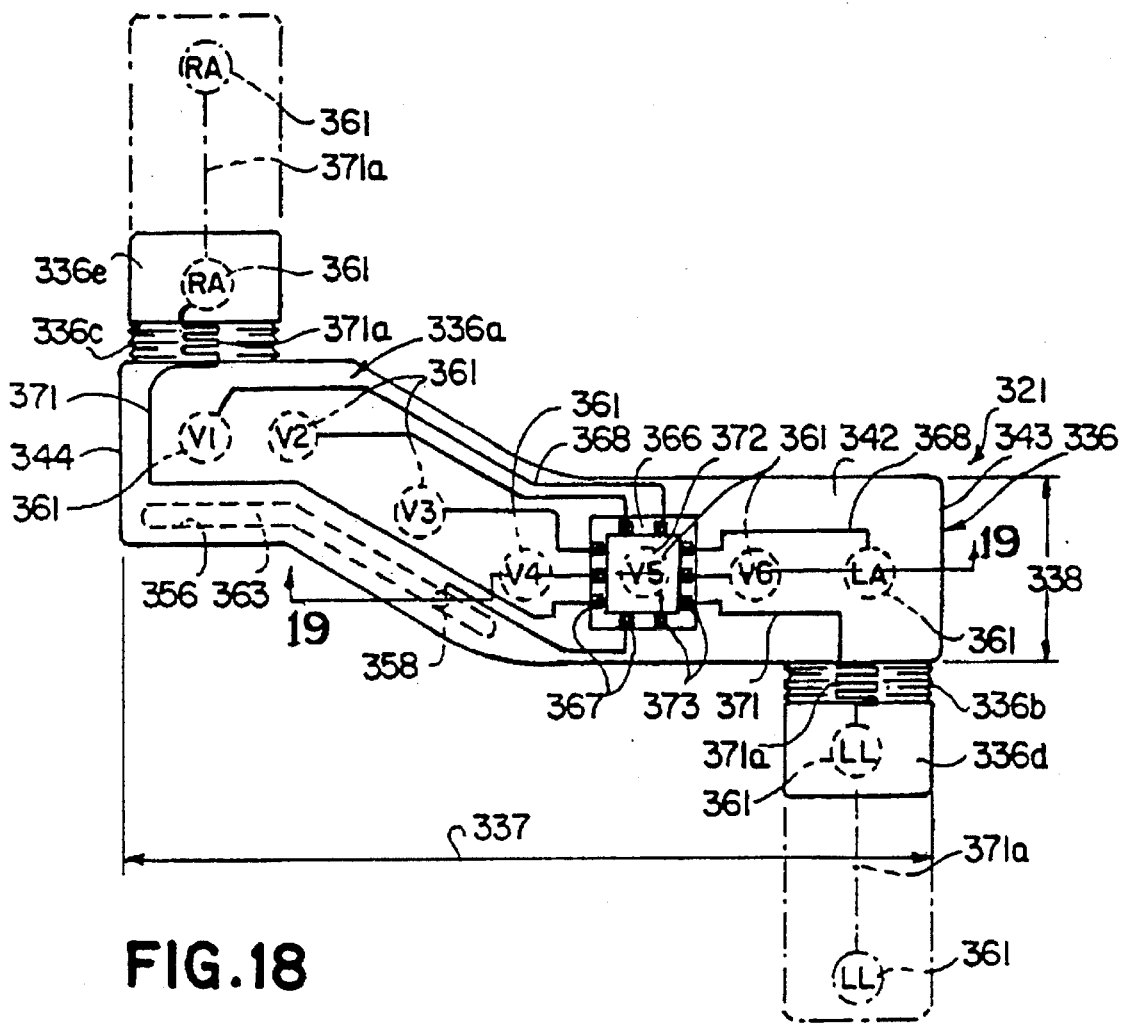
FIG. 18 is a top plan view of the precordial strip assembly shown in FIG. 17.
Figure 19:
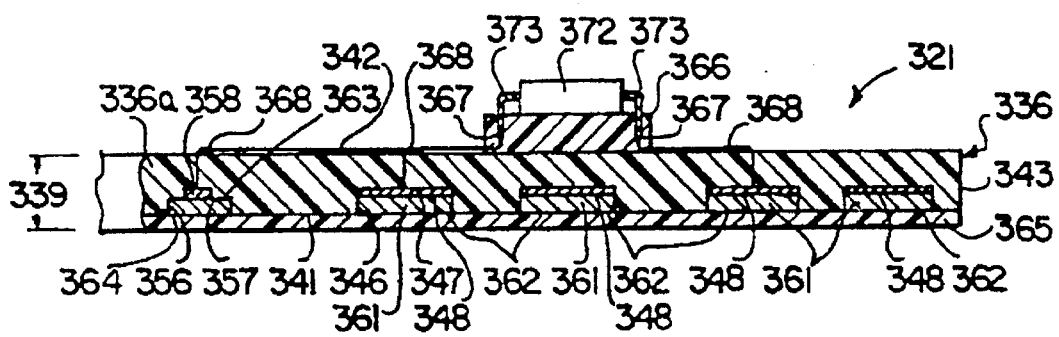
FIG. 19 is a cross-sectional view of the precordial strip assembly shown in FIG. 18 taken along the line 19 in FIG. 18.

Strip-patch 336 has a length and a width identified by dimensions 337 and 338 in FIG. 18 and a height identified by dimension 339 in FIG. 19. Length 337 can range from about seven centimeters to about thirty centimeters, and width 338 can range from about two to five centimeters, and height 339 can range from about three millimeters to fifteen millimeters. Strip-patch 336 can be made in various sizes to fit the desired range of pediatric, male or female patients. It also can be color coded or number-classified to facilitate identification and application-specific use.

Strip-patch 336 is comprised of a central elongate portion 336a which is generally linear and has first or left and second or right ends 343 and 344. Strip-patch 336 has first and second elastic portions 336b and 336c which commence near first and second ends 343 and 344, respectively, and first and second extendable or stretchable portions 336d and 336e adjacent elastic portions 336b and 336c. Elastic portions 336b and 336c protrude from central portion 336a at approximately right angles, and extendable portions 336d and 336e are substantially collinear with elastic portions 336b and 336c, respectively. Strip-patch 336 further has first and second surfaces 341 and 342.

Strip-patch 336 can be made from a suitable non-conductive, insulating and flexible plastic derived sheet formed from a layer of material such as polyurethane or polyvinyl chloride (PVC), or any combination thereof. Polyurethane offers flexibility with relative higher stiffness. Its hardness scale (e.g., numerically measured 21, 41, 81 or 90) can be adjusted by blending materials of various hardness to obtain the desired flexibility and stiffness. Thus, if desired, the hardness of strip-patch 336 can be varied from one option to another and from one portion to another to provide elastic portions 336b and 336c to be stretchable to permit pulling of extendable portions 336d and 336e from positions near central portion 336a to positions remote from central potion 336a. Polyvinyl chloride, on the other hand, offers higher flexibility by using variations in the thickness of the material and changing the number of the layers. Thus, single or multiple layers can be provided with the same thickness or variable tapered thicknesses.

Strip-patch 336 is provided with a plurality of spaced apart cylindrical or square receptacle bores 346 commencing in first surface 341 and terminating at inner surface 347 of strip-patch 336, one of which is identified in each of FIGS. 18 and 19. A thin cylindrical conductive pad 348 is disposed in each receptacle bore 346 and mounted to inner surface 347. Central portion 336a of strip-patch 336 is also provided with an elongate recess 356 terminating at inner surface 357 of strip-patch 336. A conductive pad 358 is embedded in a portion of inner surface 357 as shown in FIG. 19.

A plurality of conductive contact elements (CCEs) or conductive elements 361 are mounted in spaced apart positions along the length of strip-patch 336 for detecting heart signals from patient 322. Conductive elements 361 are generally cylindrical in conformation and have a contact surface 362 and dimensions which permit their disposition in receptacle bores 346 such that contact surface 362 is exposed on and generally in the plane formed by first surface 341 of strip-patch 336. CCE 361 is fastened to conductive pads 348 with a suitable conductive adhesive.

CCE 361 include six precordial contact elements identified as $V_1$ through $V_6$ mounted sequentially across first surface 341 of central portion 336a with the $V_1$ conductive element adjacent to second end 344 of central portion 336a. CCE 361 also include a seventh conductive element 361 identified as LA mounted on first surface 341 of central portion 336a adjacent to first or left end 343 and the $V_6$ conductive contact element (at the very left side of central portion 336a of strip 336, at mid-axillary line position, as viewed on patient 322). Two additional CCEs 361 identified as LL and RA are mounted in first and second extendable portions 336d and 336e, respectively. Conductive element LL on extendable portion 336d is separated or set apart from adjacent conductive element LA on central portion 336a by first elastic portion 336b, while conductive element RA on second extendable portion 336e is separated or set apart from adjacent conductive element $V_1$ on central portion 336a by second elastic portion 336c.

First and second elastic portions 336b and 336c serve as stretchable means. First elastic portion 336b permits spacing of LL CCE 336a between a first position in close proximity with $V_1$ through $V_6$ conductive elements 361 and adjacent LA CCE 361 and a second position or "floating" position remote therefrom as illustrated in FIG. 18. Second elastic portion 336c permits spacing of RA CCE 361 between a first position in close proximity with $V_1$ through $V_6$ conductive elements 361 and adjacent conductive element $V_1$ and a second position or "floating" position remote therefrom also illustrated in FIG. 18. First and second elastic portions 336b and 336c stretch and extend approximately five to fifteen centimeters to permit spacing of LL and RA CCE 361 in a second remote position. Elastic portions 336b and 336c of strip 336 contain suitable elastic qualities, such as those discussed above, to urge LL and RA conductive elements 361 towards their first position.

An elongate (or of any other shape) reference contact element is reference element 363 having a contact surface 364 and made of a suitable material such as copper or carbon or silver-silver chloride or other silver derivative or any combination thereof, is carried by central portion 336a of strip 336 and serves as a common reference for conductive elements 361. Reference element 363 is mounted in elongate recess 356 such that contact surface 364 is exposed on and generally in the plane formed by first surface 341 of central portion 336a. Reference element 363 is fastened to inner surface 357 in a suitable manner and to conductive pad 358 with a suitable conductive adhesive. It should be appreciated by those skilled in the art that reference element 363 is within the scope of the present invention if it is a single long element, is partially extended and/or consists of several electrically connected segments, regardless of whether the segments are adjoining. In addition, reference element 363 may have a circular, ring shaped or other conformation and/or be located elsewhere on strip 336.

Most desirably, first surface 341 of at least central portion 336a and first and second extendable portions 336d and 336e of strip 336 is adhesive to permit retention of CCE 361 and 363 and strip 336 in proper position when strip assembly 321 is placed on precordium area 326. Adhesive first surface 341 carries a protective covering 365, as illustrated in FIG. 19 with respect to central portion 336a, which is removed therefrom to expose first surface 341 for placement on precordium area 326. Protective covering 365 may be of a one piece or segmented design; a one piece design would permit removal of the protective covering in a single removal action. It should be appreciated by those skilled in the art that first surface 341 may have adhesive characteristics only in the vicinity of contact elements 361 and 363, or contact elements 361 and 363 may be retained in position on the patient by other means, and be within the scope of the present invention.

Chip receptacle 366 serves as junction means carried in a single region by central portion 336a of strip 336, as illustrated in FIGS. 18 and 19, and has a sufficient number of pin sockets 367 for receiving the heart signals detected by contact elements 361 and 363. Chip receptacle 366 is mounted on second surface 342 of central portion 336a by suitable adhesive means.

Conductive pad 358 and each cylindrical conductive pad 348 on central portion 336a is connected by a thin conductive wire 368 to a pin socket 367, with wires 368 and conductive pad 358 or cylindrical conductive pads 348 serving as means for electrically coupling and connecting reference element 363 and $V_1$ through $V_6$ and LA conductive elements 361, respectively, to chip receptacle 366. (Several representative pin sockets 367 and wires 368 are identified in FIGS. 18 and 19.) Wires 371 and cylindrical conductive pads 348 on extendable portions 336d and 336e serve as the means for electrically coupling and reconnecting LL and RA conductive elements 361 to chip receptacle 366, and have extendable or stretchable portions 371a which are urged towards the first position when extendable portions 336d and 336e are in the first position and capable of extension to a second position when extendable portions 336d and 336e are in a second remote position. By electrically coupling and connecting conductive pads 348 and 358 to chip receptacle 366, wires 368 and 371 serve to electrically couple and connect conductive elements 361 to reference element 363.

A microchip 372 is mounted on second surface 342 of central portion 336a of strip-patch 336 in contact with the junction means for transmitting a radio frequency signal which carries the heart signals detected by contact elements 361 and 363. More specifically, microchip 372 receives the heart signals detected by precordial $V_1$ through $V_6$ conductive elements 361, LA, RA and LL conductive elements 361, and reference element 363 (See FIG. 20). Microchip 372 is received by chip receptacle 366 for retention on strip-patch 336 and has a plurality of pins 373 which cooperatively mate with pin sockets 367 (See FIG. 19). Microchip 372 may be detachably mounted to chip receptacle 366. For example, microchip 372 can be plugged into and ejected out of chip receptacle 366 mounted on strip-patch 336 of strip assembly 321.

Microchip 372 includes means for transmitting a single encoded radio frequency signal which carries the twelve-lead electrocardiographic multiple heart signals detected by contact elements 361 and 363, and comprises one or more microchip amplifiers and filters, a multiplexer, a microchip encoder-modulator, a microchip transmitter, a wireless-signal radiator and a battery means. Microchip 372 can transmit a time multiplexed and modulated multichannel twelve-lead electrocardiogram by a digitally encoded radio frequency signal via a single frequency wavelength channel.

Some of the components of the wireless electrocardiograph monitoring system contained in microchip 372 are illustrated in FIG. 17. Microchip 372 includes amplifiers 381 (shown for simplicity as a single amplifier), encoder-modulator 382 (which includes an analog-to-digital converter and a multiplexer), transmitter 383 and wireless-signal radiator or sending antenna 386. The digitally encoded radio frequency signal containing the time multiplexed and modulated multi-channel twelve-lead electrocardiogram is received by receiving antenna 387, after which it passes through receiver-demodulator 388, decoder 391, buffer amplifier 392, electrocardiograph lead selector 393 and filter amplifiers 396 (shown for simplicity as a single amplifier). From filter amplifiers 396, the twelve signals detected by the twelve-lead electrocardiogram can be sent to an electrocardiographic printer 397, a monitor 398 and/or a Holter recording 399.

A more detailed diagram of a wireless electrocardiograph monitoring system (WEMS) is illustrated in FIGS. 20 and 21. Microchip 372 has a separate amplifier for amplifying to a more workable level the relatively weak heart signals detected by $V_1$ through $V_6$, LA, RA and LL conductive elements 361 and reference element 363. Each amplifier 381 can include a filter for removing or suppressing undesirable portions of the detected signal; this filter may be similar to that contained in differential input amplifier 26'. Each microchip amplifier with filter has a signal input terminal coupled to each pin 373 carrying a heart signal from a conductive element 361 or reference element 363, and an output terminal for sending the amplified and filtered heart signals.

The output of each amplifier 381 is connected to an input to analog multiplexer 401, a time-division multiplexed system, which combines the heart signals for transmission through a common channel. Multiplexer 401 includes an analog-to-digital converter for converting the analog heart signals detected by contact elements 361 and 363 to digital signals, and an encoder-modulator which changes the combined heart signals into an information signal suitable for propagation over radio frequency. The encoder-modulator may include adjustment means for varying the digital encoding of the encoder-modulator.

Multiplexer 401 is connected to control logic 402 which monitors microchip 372 and the heart signals received thereby. A synchronized signal travels between multiplexer 401 and control logic 402 to permit monitoring of strip assembly 321. For instance, if patient 322 is out of range from the receiving unit or the battery powering microchip 372 is low, a sound or visual LED warning may be triggered. Multiplexer 401 can also be connected to motion electronic stabilizers 403 (which in turn would be connected to control logic 402) for avoiding artifacts which can result in misleading readouts. (Artifacts create additional background noise which is picked up by contact elements 361 and 363 and reduces the accuracy of the electrocardiographic reading). Multiplexer 401 has an output for transmission of a modulated output signal, and control logic 402 has an output for transmission of certain control capability information.

The outputs of multiplexer 401 and control logic 402 are connected to inputs to transmitter 383 which generates a high frequency electric current or carrier wave whose characteristics of amplitude, frequency or phase modulation are altered, or modulated, by the output signal from the encoder-modulator within multiplexer 401. Transmitter 383 may include an adjustment means for varying the frequency of operation thereof. The output of transmitter 383 is coupled to the input for the wireless-signal radiator 386 which radiates the signal over a single radio frequency.

Microchip 372 includes battery means, such as a 3 volt lithium coin cell, which serves as an exclusive power supply for strip assembly 321 and microchip 372 and has at least one voltage terminal for supplying power to microchip 372 and a ground terminal carried on first surface 341, possibly by reference element 363. Microchip 372 includes a means of reapplying operating potentials from the battery means to amplifiers 381, multiplexer 401, control logic 402, motion electronic stabilizers 403 and transmitter 383.

The radio frequency signal is received by antenna 387, which receives signals in quadrature configuration. the radio frequency signal is sent to receiver 11 which has a front end 412 and produces a synchronized output signal and a time multiplexed output signal. The outputs of receiver 411 are connected to the inputs of decoder and controller 413. Decoder and controller 413 is connected to alarm controller 416. The twelve electrocardiogram leads, detected and generated on patient 322 in accordance with both the unipolar and bipolar lead systems, are removed from the time multiplexed signal by decoder and controller 416 and separately fed through filter amplifiers 396 to interface unit 417. The twelve-lead electrocardiogram can be sent by interface unit 417 to an electrocardiographic printer 397 and/or a display monitor 398.

It should also be appreciated by those skilled in the art that strip assembly 321 may have means for transmitting a time multiplexed and modulated multichannel twelve-lead electrocardiogram by a digitally encoded radio frequency signal via a single frequency wavelength which includes or consists of components other than those described above and/or accomplishes the transmitting of heart signals by means other than as discussed herein and still be within the scope of the present invention.

Strip-patch assembly 321 is sized and configured such that $V_1$ through $V_6$ and the other conductive elements 361 are properly positioned on patient 322 to permit standard twelve-lead (I, II, III, aVR, aVL, aVF, $V_1$, $V_2$, $V_3$, $V_4$, $V_5$ and $V_6$) electrocardiographic monitoring. Contact elements 361 and 363 on strip-patch 336 are adapted to contact skin 327 for detecting the required heart signals from patient 322 when strip-patch assembly 321 is placed on precordium area 326 of patient 322. Placement of strip-patch assembly 321 on patient 322 is relatively simple and quick. After selecting the proper size strip assembly to fit the size of the patient's thorax, protective covering 365 is removed from fist surface 341 of central potion 336a of strip 336 to expose contact elements 361 and 363 thereon, and central portion 336a is then placed on precordium area 326. (If protective covering 365 is of a one piece design, it is removed from all of first surface 341 at this time.) Adhesive first surface 341 of central portion 336a retains in it position on precordium area 326. LA conductive element 361 carried on central portion 336a of strip-patch 336 adjacent $V_6$ conductive element 361 and first end 343 is positioned on strip-patch 336 so as to be near left arm 331 and substitutes for the separate electrode formerly positioned on the left arm of patient 322.

LL and RA conductive elements 361 are positioned on patient 322 by simply pulling extendable but electrically connected portions 336d and 336e from their first position near $V_1$ through $V_6$ and LA conductive elements 361 to their second position remote from $V_1$ through $V_6$ and LA contact elements and near left leg 333 and right arm 328, respectively, of patient 322. More specifically, LL conductive element 361 is placed in a remote position on the lower left thorax or upper left abdomen of patient 322, and RA conductive element 361 is placed in a remote position on the upper right thorax of patient 322. In their remote positions, LL and RA conductive elements 361 constitute "floating" conductive elements positionable remotely in respect to the elongated central portion 336a containing the linear and sequential CCEs of $V_1$–$V_6$.

The pulling capability of extendable portions 336d and 336e away from central portion 336a to position or place LL conductive element 361 on the lower left thorax or upper left abdomen and RA conductive element 361 on the upper right thorax area, is permitted by first and second elastic portions 336b and 336c of strip-patch 336 and extendable portions 371a of wires 371. When LL and RA conductive elements 361 are in their extendable remote positions, first and second extendable portions 336d and 336e are each distanced between five and fifteen centimeters from central portion 336a. There is no need for millimetric accuracy in positioning of LL and RA conductive elements 361 carried by extendable portions 336d and 336e.

If protective covering 365 is segmented and not yet been removed, the balance of the protective covering is removed from extendable portions 336d and 336e of strip 336, to expose LL and RA conductive elements 361 and adhesive first surface 341, before placing first and second extendable portions 336d and 336e on patient 322. LL and RA "floating" conductive elements 361 carried by extendable portions 336d and 336e substitute for the separate electrodes formerly positioned on the left leg and right arm of the patient.

It should be appreciated that elastic portions 336b and 336c may be designed to permit extendable portions 336d and 336e to separate and break off from central portion 336a during placement of LL and RA conductive elements 361 on patient 322 and be within the scope of the present invention. The separation of extendable portions 336d and 336e from central portion 336a by causing elastic portions 336b and 336c to break apart can be accomplished by adjusting the elasticity and flexibility of the polyurethane, polyvinyl chloride or other plastic material from which the elastic portions are made. For example, if elastic portions 336b and 336c are made of polyurethane, it is possible to set its hardness scale to be low enough to permit complete separation.

Elastic portions 336b and 336c designed to completely separate from central portion 336a do not cause wires 371 to break or damage. Accordingly, LL and RA conductive elements 361 remain electrically connected and coupled to microchip 372 by respective wired 371. Stretchable portions 371a of wires 371 permit such electrical coupling when LL and RA conductive elements are in their remote "floating" positions.

The inclusion in strip-patch assembly 321 of common reference element 363 eliminates the need to place a separate reference electrode on the right leg of patient 322. In addition, reference element 363 is a common reference for all conductive elements 361. As a result, there is no need to electronically or otherwise calculate the reference point during unipolar monitoring. A conductive gel may be applied between each contact element 361 and 363 to enhance the detection of heart signals thereby. Strip-patch assembly 321 may be provided with a microchip 372 which is removable or permanently fixed. A removable microchip 372 can be reused in multiple monitoring, reducing the cost of an electrocardiographic testing performance.

Upon commencement of monitoring, the twelve lead electrocardiographic monitoring system carried by strip assembly 321 detects heart signals at each of the ten CCEs 361 and 363, to permit complete unipolar and bipolar "leads" views of heart 324 electrical activity. The reference signal is generated by reference element 363 incorporated within strip-patch device assembly 321. Once detected, the signals are carried through wires (or via printed circuit means) 368 and 371 to chip receptacle 366, where they are picked up by pins 373 on microchip 372 which cooperatively mate with pin sockets 367 in the chip receptacle. Microchip 372 combines the heart signals detected by contact elements 361 and 363 into a twelve-lead electrocardiogram configuration. Microchip 372 contains the necessary electronic components for transmitting the multiplexed encoded and modulated twelve-lead electrocardiogram heart signals over a single frequency radio frequency signal. No wires connecting patient 322 to the receiver and decoder portion of the wireless system are needed to permit completion of the electrocardiographic monitoring.

Thus, microchip 372 transmits the 12-lead electrocardiogram single encoded signal using the information derived from the electrocardiographic standard twelve-lead "views". The electrocardiogram "lead" is a "view point" from which the electrical activity of the heart is examined. Each "view" is the result of the potential difference between two CCEs spaced apart and separated points, such as one conductive element 361 and another conductive element from the 361 group. RA, LA and LL conductive elements 361 are compared each to the other in order to determine bipolar leads I, II and II of the Einthoven triangle bipolar lead system. LL, LL, RA and $V_1$ through $V_6$ conductive elements 361 are compared to common reference element 363 in order to determine the "views" of unipolar leads, aVR, aVL, aVF and $V_1$ through $V_6$ in the unipolar lead system.

Therefore, in accordance with this invention, microchip 372 provides the end result and data processing of these views of coupled CCEs measurements, of which every two contact elements provide a "lead view", while coupling of variable contact elements create, according to electrophysiological principals, the complete "picture" of twelve-lead electrocardiogram. The inclusion by this invention of microchip 372 in strip assembly 321 creates an "active" and "smart" wireless electrode device-system which permits a "novel" method of electrocardiographic analysis. Under this method, a complete twelve-lead electrocardiogram is created on the patient end and not at the hardware end. This twelve-lead electrocardiogram is created not merely by electrocardiographic hardware, as is done by current and existing electrocardiograph systems. Thus, the invention provides a new "smart" method of electrocardiographic data analysis and processing.

During monitoring, patient 322 can ambulate within the approximate 50 meter transmission range of microchip 372 without interrupting the detection and transmission of twelve-lead electrocardiographic heart signals for analysis. Motion electronic stabilizers may be incorporated or connected to or within microchip 372 in order to optimize "clean" from noise recording of heart signals. These stabilizers may consist of a combination of various filters and similar digital signal stabilizers to eliminate unwanted surrounding noise and patient movement artifacts. This can be achieved by means of digital substraction of noise detected from the detection of electrical signals and noise together, resulting in a "clean" signal from surrounding noise having left only the detected electrical signals. Furthermore, the unitary structure of strip-patch assembly 321 eliminates the likelihood of interchanging signals and the inaccuracies in the heart signals from faulty wires and wire connections or disconnections.

In another embodiment, precordial strip-patch assembly 321 includes an elongate strip or strip means 431 generally in the shape of a horizontal inverted "L," and having a length identified by dimension 432 in FIG. 22 and a width and height substantially equal to width 338 and height 339 in FIGS. 18 and 19, respectively. Length 432 can range from about seven to about twenty centimeters. Strip-patch 431 can be made from the same material as strip-patch 336, and has a central portion 431a, first and second elastic portions 431b and 431c and first and second extendable or stretchable portions 431d and 431e substantially identical to central portion 336a, first and second elastic portions 336b and 336c and first and second extendable portions 336d and 336e of strip-patch 336. Central portion 431a has first or left and second or right ends 343 and 344.

Like central potion 336a, central portion 431a has $V_1$ through $V_6$ and LA conductive contact elements 361 and a reference contact element 363 mounted thereon, and is also provided with a chip receptacle 366 and a microchip 372 thereon. Wires 368 assist in electrically connecting and coupling $V_1$ through $V_6$ and LA conductive elements 361 and reference element 363 to chip receptacle 366. First and second extendable portions 431d and 431e have LL and RA conductive contact elements 361 mounted thereon in the same manner as those elements are mounted on extendable portions 336d and 336e, respectively. Wires 371, with extendable or stretchable portions 371a, assist in electrically connecting and coupling LL and RA conductive elements 361 to chip receptacle 366. First elastic and extendable portions 431b and 431d are configured with respect to central portion 431a in the same manner as first elastic and extendable portions 336b and 336d are configured with respect to central portion 336a. Second elastic and extendable portions 431c and 431e protrude in a substantially collinear manner from second end 344 of central portion 431a.

In another related embodiment, precordial strip assembly 321 includes an elongate strip-patch or strip-patch means 441 generally linear and horizontal in conformation, and having a length identified by dimension 442 in FIG. 23 and a width and height substantially equal to width 338 and height 339 in FIGS. 18 and 19, respectively. Length 442 can range from five to about twenty centimeters. Strip-patch 441 can be made from the same material as strip 336, and has a central portion 441a, first and second elastic portions 441b and 441c and first and second extendable or stretchable portions 441d and 441e substantially identical to central portion 336a, first and second elastic portions 336b and 336c and first and second extendable portions 336d and 336e of strip 336. Central portion 441a has first or left and second or right ends 343 and 344.

Like central portion 336a, central portion 441a has $V_1$ through $V_6$ and LA conductive contact elements 361 and a reference contact element 363 mounted thereon, and is also provided with a chip receptacle 366 and a microchip 372 thereon. Wires 368 assist in electrically connecting and coupling $V_1$ through $V_6$ and LA conductive elements 361 and reference element 363 to chip receptacle 366. First and second extendable portions 441d and 441e have LL and RA conductive contact elements 361 mounted thereon in the same manner as those elements are mounted on extendable portions 336d and 336e, respectively. Wires 371, with extendable or stretchable portions 371a, assist in electrically connecting and coupling LL and RA conductive elements 361 to chip receptacle 366.

First elastic and extendable portions 441b and 441d protrude in a substantially collinear manner from first end 343 of central portion 441a. Second elastic and extendable portions 441c and 441e protrude in a substantially collinear manner from second end 344 of central portion 441a.

The operation of strip assembly 321 which includes either strip-patch 431 or strip-patch 441 is similar to the operation discussed above with respect to the strip assembly having strip-patch 336. After selecting the proper size strip assembly 321 and placing central portion 431a or 441a on the precordium area 326 of patient 322, LL and RA conductive elements 361 on strip-patch 431 or 441 are positioned on patient 322 near left leg 333 and right arm 328, respectively, of patient 322. More specifically, LL conductive element 361 is placed on the lower left thorax and upper left abdomen of patient 322, and RA conductive element 361 is placed on the upper right thorax of patient 322.

With respect to strip-patch 431, LL conductive element 361 is so positioned by pulling extendable portion 431d downwardly from its first position near $V_1$ through $V_6$ and LA conductive elements 361 to its second position remote the $V_1$ through $V_6$ and LA conductive elements. With respect to both strip-patches 431 and 441, RA conductive element 361 is so positioned by pulling extendable portion 431e or 441e sidewardly or rightwardly from its first position near $V_1$ through $V_6$ and LA conductive elements 361 to its second position remote to the $V_1$ through $V_6$ and LA conductive elements. In their remote positions, LL and RA conductive elements 361 constitute "floating" conductive elements.

In each instance, the pulling of extendable portions 431d and 431e or 441d and 441e away from central portion 431a or 441a, respectively, is permitted by first and second elastic portions 431b and 431c or 441b and 441c and extendable portions 371a of wires 371. When LL and RA conductive elements 361 are in their remote positions, the extendable portions are each distanced between five and fifteen centimeters from the central portion.

In another embodiment, precordial strip assembly 321 includes an elongate strip or strip means 451 substantially similar to central portion 336a of strip-patch 336. Like strip-patch 336, strip-patch 451 has $V_1$ through $V_6$ and LA CCE 361 and a reference contact element 363 mounted thereon, and is also provided with a chip receptacle 366 and a microchip 372 thereon (See FIGS. 24 and 25). Microchip 372 includes amplifiers 381 (shown for simplicity as a single amplifier), encoder-modulator 382 (which includes an analog-to-digital converter and a multiplexer), transmitter 383 and wireless-signal radiator or sending antenna 386. Wires 368 assist in electrically connecting and coupling $V_1$ through $V_6$ and LA conductive elements 361 and reference element 363 to chip receptacle 366.

In this embodiment, LL and RA conductive elements 361 are mounted on first and second patches 452 and 453 in the same manner that conductive elements 361 are mounted on strip-patches 336 and 451. Strip-patches 452 and 453 are made of a suitable non-conductive and insulating layer of plastic material which is also flexible. The plastic material may include suitable materials such as polyurethane and/or polyvinyl chloride, or a combination thereof, and may be formed through the processes discussed above to vary in flexibility. Strip-patches 452 and 453 have an adhesive on one surface thereof similar to the adhesive contained on first surface 341 of strip-patch 336. Wires 454, which are thin, conductive and flexible, serve as means for electrically coupling and connecting RA and LL conductive elements 361 to chip receptacle 366. Wire 454 relating to LL patch 452 joins strip 451 near left end 343, while 454 relating to patch 453 joins strip 451 near right end 344. Wires 454 extend from three to about ten centimeters from strip-patch 451.

RA and LL conductive elements 361 are adapted to contact skin 327 near right arm 328 and left leg 333, respectively, for detecting heart signals from patient 322. More specifically, RA conductive element 361 is positioned on the upper right thorax of the patient, and LL conductive element 361 is positioned on the lower thorax and left upper abdomen of the patient.

The operation of strip-patch assembly 321 which includes strip-patch 451 is similar to the operation discussed above with respect to the strip assembly having strip 336. Strip-patches 452 and 453 are placed on patient 322 in close proximity to strip-patch 451, and wires 454 can serve to define the maximum distance between the patches and strip-patch 451.

In another embodiment, precordial strip-patch assembly 321 includes an elongate strip-patch or strip-patch means 471 which is slightly shorter in length but otherwise substantially similar to central portion 336a of strip-patch 336. Strip-patch 471 has $V_1$ through $V_6$ conductive contact elements 361 mounted thereon, like strip-patch 336, but does not have a LA conductive element or a reference contact element mounted thereon (See FIG. 26). Strip-patch element 471 has first or left and second or right ends 472 and 473, and is also provided with a chip receptacle 366 and a microchip 372 thereon. Wires 368 assist in electrically connecting and coupling $V_1$ through $V_6$ conductive elements 361 to chip receptacle 366.

LL and RA conductive elements 361 are mounted on first and second patches 452 and 453, in the same manner as on strip assembly 321 which includes strip-patch 451 illustrated in FIG. 25, and are electrically coupled and connected to chip receptacle 366 by wires 454. In this embodiment, LA conductive element 361 is similarly mounted on a patch 476 and a tenth contact element, reference contact element 477 which is substantially identical in construction to conductive contact elements 361, is also similarly mounted on a strip-patch 478. Strip-patch 478, with conductive element 361 thereon, is sometimes referred to as the RL contact element.

Strip-patches 476 and 478 are made of a suitable non-conductive and insulating layer of plastic material which is also flexible. The plastic material may include suitable materials such as polyurethane and/or polyvinyl chloride, or a combination thereof, and may be formed through the processes discussed above to allow change or variability in the flexibility of the material. Strip-patches 476 and 478 have an adhesive on one surface thereof similar to the adhesive contained on first surface 341 of strip 336. Wires 481, which are thin, conductive and flexible, serve as means for electrically coupling and connecting LA conductive element 361 and RL reference element 477 to chip receptacle 366. Wire 481 relating to LA strip-patch 476 joins strip-patch 471 near the left end 472, while wire 481 relating to strip-patch 478 joins strip-patch 471 near the right end 473. Wires 481 extend from three to fifteen centimeters from strip-patch 471.

LA conductive element 361 and RL reference element 477 are adapted to contact skin 327 near left arm 331 and right leg 332, respectively, for detecting heart signals from patient 322. More specifically, LA conductive element 361 is positioned on the upper left thorax of the patient, and RL reference element 477 is positioned on the lower thorax and right upper abdomen of the patient.

The operation of strip-patch assembly 321 which includes strip-patch 471 is similar to the operation discussed above with respect to the strip assembly having strip-patch 336. Patches 452, 453, 476 and 478 are placed on patient 322 in close proximity to strip 471, and wires 454 and 481 can serve to define the maximum distance between the patches and strip 471.

In another embodiment of strip assembly 321, a strip-patch 488, substantially similar to central portion 336a but without chip receptacle 366 and microchip 372, includes cable means for carrying the heart signals detected by contact elements 361 and 363 to the monitor and related analysis equipment. Strip 488 has first or left and second or right ends 489 and 490. In this embodiment, illustrated in FIG. 27, the junction means is comprised of a cable jacket 491 being carried in a single region near first end 489 of strip 488 and having a plug 492 on the end thereof. Strip 488 has wires 493 which, together with cylindrical conductive pads 348 and conductive pad 358, serve as means for electrically coupling and connecting conductive elements 361 and reference element 363, respectively, to cable jacket 491. Cable 494 serves as a cable means and connects to plug 492. Strip assembly 321 of this embodiment could include elastic and extendable portions similar to elastic portions 336b and 336c and extendable portions 336d and 336e or patches similar to patches 452, 453 and 476 for carrying LL, RA and/or LA conductive elements 361 or similar to patch 478 for carrying reference element 477 and be within the scope of the present invention.

Figure 28:
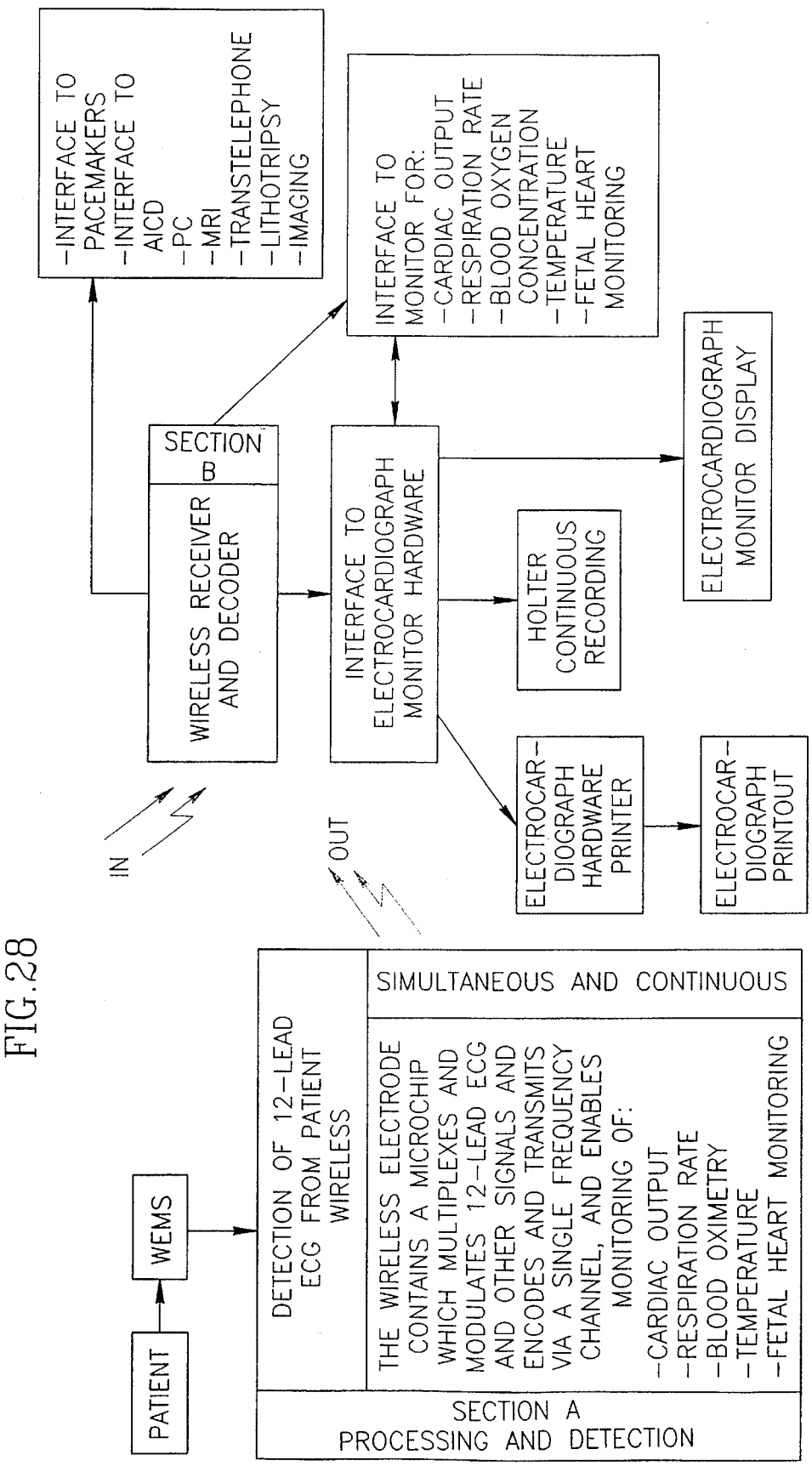
FIG. 28 is a block diagram of a wireless electrocardiographic monitoring system (WEMS) which incorporates the present invention.

Precordial strip-patch assembly 321 utilizes the method and device-system of electrocardiographic monitoring in which the detection and processing of a 12-lead electrocardiogram is performed and accomplished on the body of patient 322 (See FIG. 28). As more fully discussed above, conductive contact elements 361 detect heart signals which correspond to traditional precordial detection points $V_1$ through $V_6$ and limb detection points LA, LL and RA and together with common reference contact elements 363 or 477. The heart signals are analyzed and coupled, by microchip 372, to create the aVR, aVL and aVF limb leads and precordial leads $V_1$ through $V_6$ of the unipolar lead system and leads I, II and III of the bipolar lead system. Microchip 372 can also serve as means for transmitting the electrocardiogram over a radio frequency signal. More specifically, microchip 372 serves to digitize and combine the multichannel twelve-lead electrocardiogram into a time multiplexed signal and send the combined signal over a single transmission frequency channel.

One of the innovative approaches suggested herein by the wireless electrocardiographic/electrophysiological monitoring system (WEMS) of the present invention is to eliminate the physical wires between the patient and the electrocardiograph or display monitor and to provide a standard twelve-lead electrocardiogram with only one electrode strip-patch device-system. This approach has the potential to greatly enhance the practicality of use and simplify the use of electrocardiographic equipment and significantly improve clinical care of patients affected by heart disease. In addition, the WEMS, a wireless electrocardiographic monitoring system according to the present invention, would expand the use of standard 12-lead electrocardiography. This may significantly improve control modalities for the diagnosis and therapy of critically ill cardiac patients that require and benefit from maximal electrophysiological detection and evaluation not available with currently existing methods and clinical management protocols which employ only single-lead or three-lead arrhythmia monitoring aimed at arrhythmia monitoring only.

A standard 12-lead WEMS, wireless electrocardiographic monitoring system, would allow early detection of unrecognized myocardial ischemia dynamics or myocardial infarction while a patient is in a coronary intensive care or in the general intensive care unit and, accordingly, expand diagnostic accuracy and specifically determine the urgency and/or the need for other therapeutic or diagnostic measurements such as medication (including anticoagulants and thrombolytic drugs), angiography, percutaneous transluminal coronary angioplasty or coronary artery bypass graft surgery.

A standard 12-lead WEMS, wireless electrocardiographic monitoring system, would also enable accurate detection of myocardial ischemia dynamics and myocardial infarction during percutaneous transluminal coronary angioplasty. An accurate detection would maximize diagnosis efficacy and improve therapy effectiveness, and possibly result, if necessary, in modification of the percutaneous transluminal coronary angioplasty procedure itself. The system would precisely determine the severity and location of the ischemic event and be critical for deciding whether to repeat the angioplasty procedure in the coronary artery and/or to modify treatment protocol with adjunctive medications (e.g., vasodilators, anticoagulants or thrombolytic drugs) and/or coronary artery bypass graft surgery. It should also be noted that there is preliminary evidence to suggest that early detection of myocardial ischemia may be an important predictor in the development of restenosis following percutaneous transluminal coronary angioplasty of the coronary arteries.

In addition, standard 12-lead electrocardiographic recordings taken during percutaneous transluminal coronary angioplasty could function as an individualized non-invasive template or "fingerprint," useful in evaluating transient ischemic episodes after the patient leaves the cardiac catheterization laboratory. Occasionally, an acute myocardial infarction develops spontaneously in the hours after elective percutaneous transluminal coronary angioplasty. The use of continuous standard 12-lead electrocardiograms would facilitate comparisons between the dynamic changes of the "controlled" ischemic period during the percutaneous transluminal coronary angioplasty procedure (as baseline value) and the ischemic period during the evolving MI (rather than observing changes in numbers of millimeters). Such information may provide a more complete understanding of the evolution of the acute ischemic process, which may be critical for therapeutic considerations.

Standard 12-lead electrocardiograms by WEMS, a wireless electrocardiographic monitoring system, would also expand the field of diagnosis and therapy of symptomatic or silent coronary ischemia in the ambulatory setting. By providing an accurate and complete ambulatory method of detecting symptomatic or silent ischemia, it could direct to early and accurate therapy (medication, invasive intervention and/or surgery), thereby increasing significantly the efficacy of therapy and potentially reducing morbidity and mortality rates associated with heart disease, the "number-one killer disease" in our society.

The WEMS' standard 12-lead wireless electrocardiographic monitoring system would also be a comprehensive and reliable ambulatory tool, by standard means and method, for providing accurate detection, 24 hours a day, automatically or upon patient's demand and in real time occurrence, of coronary ischemia or myocardial infarction in high risk cardiac patients who must transmit electrocardiograms transtelephonically. As such, the standard twelve-lead electrocardiograms, detected by the 12-lead wireless electrocardiographic monitoring system of this invention, would be recorded and microprocessed within a portable board housed in about a beeper-size (H5 cm×W3 cm×D2 cm) twelve-lead electrocardiogram recorder and transmitter having a resident logic memory-loop to detect also pre-event ECG recording, that will be carried by the patient and be transmitted by the patient through any telephone line (wired or cellular) to a cardiac monitoring center manned with experts in cardiology. This system would expand the quality of heart disease control and detection capabilities and, in addition, would direct to better accuracy of treatment, whether it be medication management, invasive intervention or urgent surgery. Furthermore, this transtelephonic method (cellular or wired) would significantly extend control modalities and improve the follow-up, at the same time, of a significant number of patients affected by heart disease, with both enhanced efficacy (quality) and efficiency (reduced cost) of treatment. Therefore, a standard twelve-lead electrocardiogram detection and diagnosis in high risk patients, 24 hours a day and upon patient's demand or upon automated threshold sound or visual alert triggering, has the potential of significantly decreasing the morbidity and mortality rates associated with heart disease. Transtelephonic 12-lead ECG would expand ambulatory and remote 12-lead ECG; high risk cardiac patients could be monitored in "real-time," practically from anywhere, via conventional or cellular communication—at home, while travelling, on vacation, during flights, in hotels, in restaurants or resorts, while driving a car, during rehabilitation or sport, etc. Clinically, it would enable optimal ECG monitoring capabilities of a very large group (practically unlimited) of patients, simultaneously; economically, it would save time for patients that need only routine 12-lead ECG check-up or real-time 12-lead ECG evaluation, and reduce the overall associated costs of ECG testing and monitoring.

The WEMS' wireless electrocardiographic monitoring system would provide continuous standard 12-lead electrocardiogram monitoring in coronary intensive care mobile units and emergency rooms for early and accurate detection and diagnosis of myocardial ischemia and myocardial infarction, thus, would improve therapeutic management and would enable the administration of thrombolytic or anticoagulative drugs in the very early stages of a coronary ischemic event. In addition, the WEMS could direct to more accurate therapy (e.g., percutaneous transluminal coronary angioplasty or coronary artery bypass graft surgery), if necessary, during hospitalization.

In patients with acute myocardial infarction who undergo thrombolytic reperfusion therapy, monitoring of ST-segment deviation could provide an early non-invasive indicator of coronary artery reocclusion not available from current coronary care electrocardiographic monitoring aimed at the detection of cardiac arrhythmias. A twelve-lead electrocardiogram can, therefore, identify patients who may require further pharmacological treatment to prevent reocclusion of the coronary artery, or who may require subsequent invasive investigation before coronary angioplasty or bypass surgery for residual coronary arterial stenosis.

Twelve-lead electrocardiograms would diagnose accurately more intraoperative and postoperative myocardial ischemia than any other monitoring modality. It is non-invasive, and would allow preoperative, intraoperative and postoperative electrocardiographic monitoring to proceed without interruption with optimal ECG evaluation capabilities.

In view of the foregoing, the WEMS' continuous wireless 12-lead electrocardiographic monitoring system of the present invention overcomes significant and practical difficulties of existing electrocardiographic monitoring systems. It accomplishes this by, for example:

1. Reducing significantly the number of electrodes required to obtain a complete standard 12-lead electrocardiogram;

2. Eliminating the time spent connecting predetermined multiple wires to predetermined multiple electrodes;

3. Eliminating wire connection errors;

4. Eliminating the time spent untangling wires;

5. Simplifying the method of operation when used by a coronary intensive care mobile unit where speed of operation is critical;

6. Reducing or eliminating wire defects that are often difficult to detect;

7. Reducing or eliminating problems relating to the wire connections at electrodes;

8. Reducing or eliminating problems relating to wire disconnections occurring beneath the sterile field during operating room surgical procedures;

9. Reducing cardiac monitoring interruptions by ambulating patients in the intermediate coronary unit;

10. Improving clinical care management as complete standard 12-lead electrocardiograms would be available for detection of myocardial ischemia and myocardial infarction during and following; percutaneous transluminal coronary angioplasty (by balloon or atherectomy means), diagnostic heart catheterization, percutaneous laser coronary angioplasty, percutaneous coronary retroperfusion, coronary artery bypass graft surgery, and thrombolytic therapy (currently, only single-lead or three-lead arrhythmia-limited monitoring is performed with these procedures.);

11. Making possible portable wireless transtelephonic standard 12-lead electrocardiographic monitoring;

12. Eliminating proximity limitations between the patient and currently operated hardware of electrocardiographs or monitors; and 13. Increasing patient compliance (comfort level) when standard 12-lead electrocardiographic testing is required (i.e., when the patient sleeps or already connected to other instrumentation or tubing, as in a coronary intensive care unit).

Figure 29:
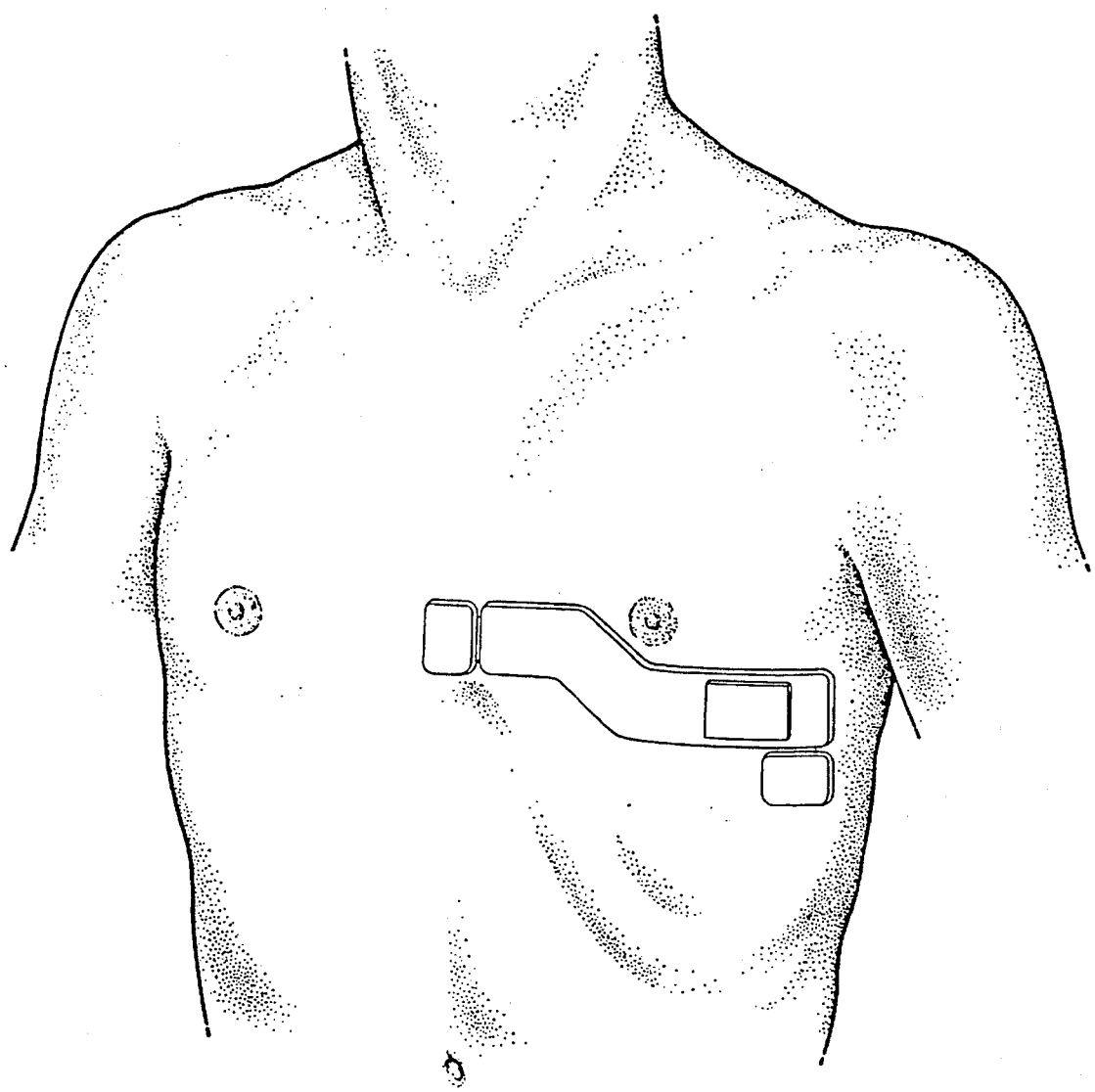
FIG. 29 is a front view of the wireless device-system for monitoring multiple physiological parameters, positioned on a chest area of a patient.

FIG. 29 is a front view of the wireless device-system for monitoring multiple physiological parameters, continuously and simultaneously, while positioned on the chest area of a patient. The electronic components are integrated within the underlying and inside structure of said compact device-system.

Figure 30:
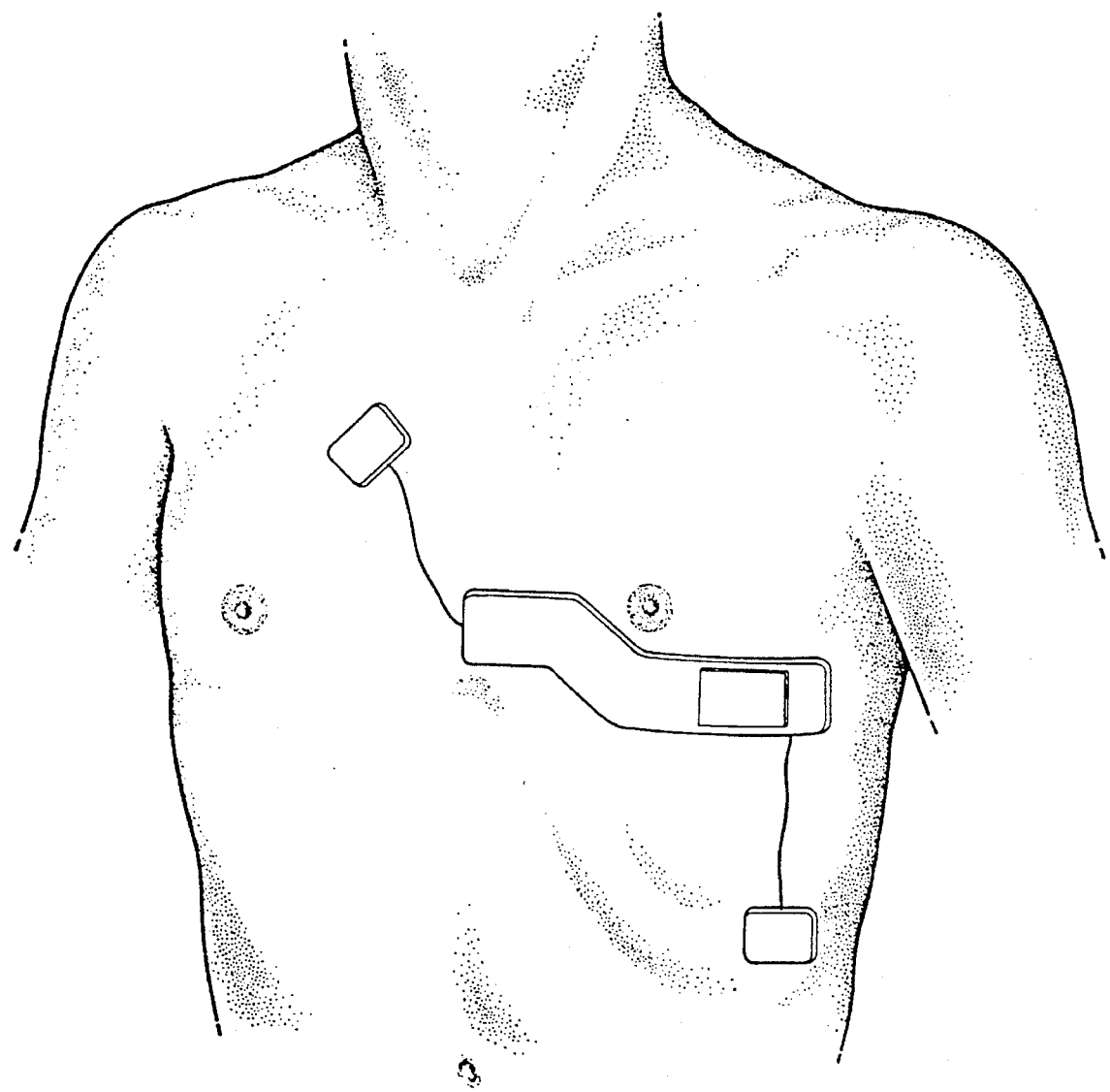
FIG. 30 is a front view of the wireless strip-patch with configuration of which two extendable conductive contact elements a positioned remotely from the elongated portion of said strip-patch, positioned at the precordial area of a human chest.

FIG. 30 is a front view of the wireless strip-patch device-system with configuration at which two extendable-stretchable CCEs are positioned remotely from the elongated strip-patch portion positioned on the precordial area of a human male chest.

Figure 31:
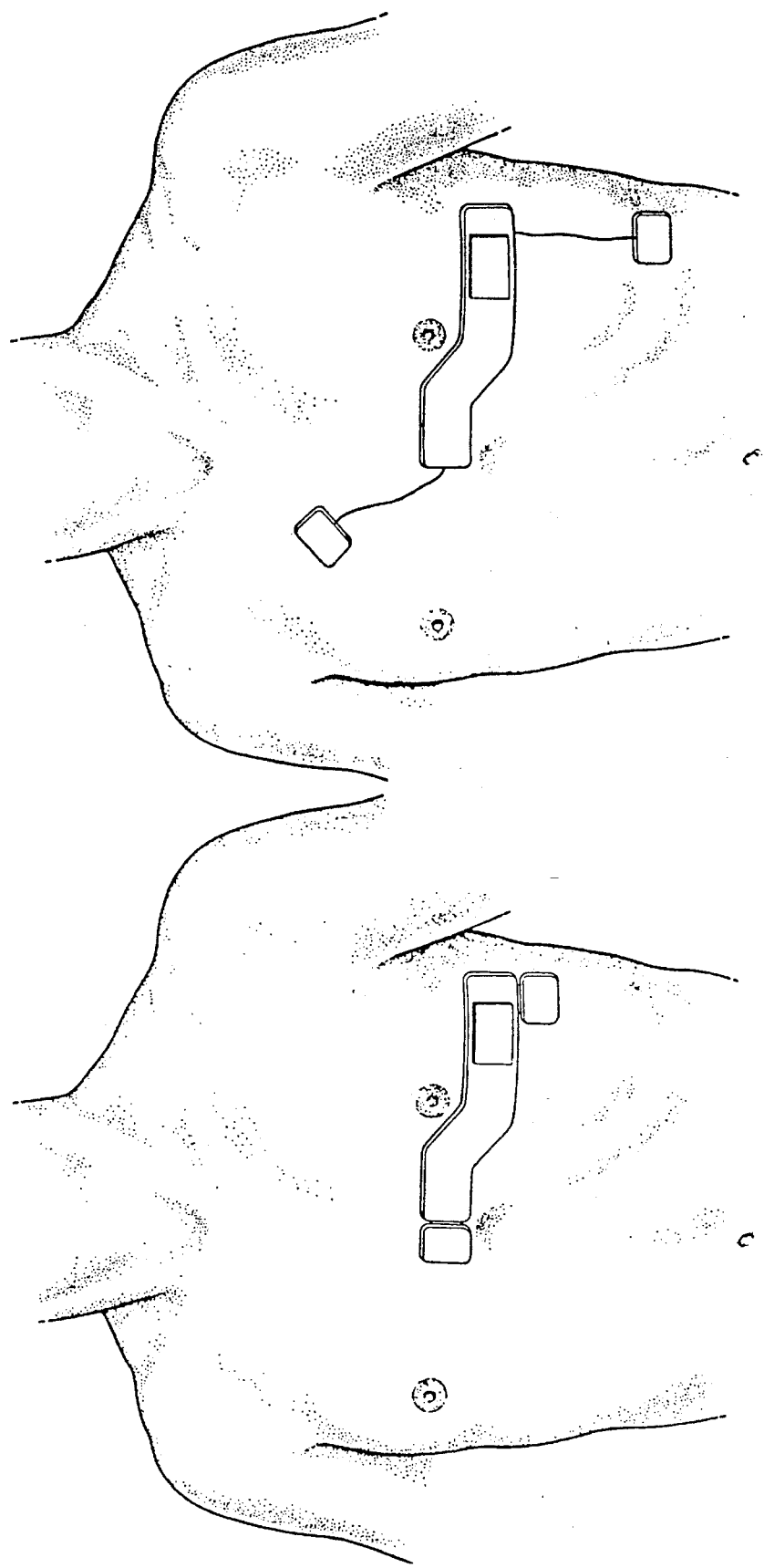
FIG. 31 is a front view of side-by-side before (left) and after (right) configuration of the wireless strip-patch device-system for monitoring multiple physiological parameters, placed on the precordial area of a human chest.

FIG. 31 demonstrate a side-by-side view before (right) and after (left) configuration of the wireless strip-patch device-system for monitoring multiple physiological parameters, placed on the precordial area of a human male chest.

Figure 32:
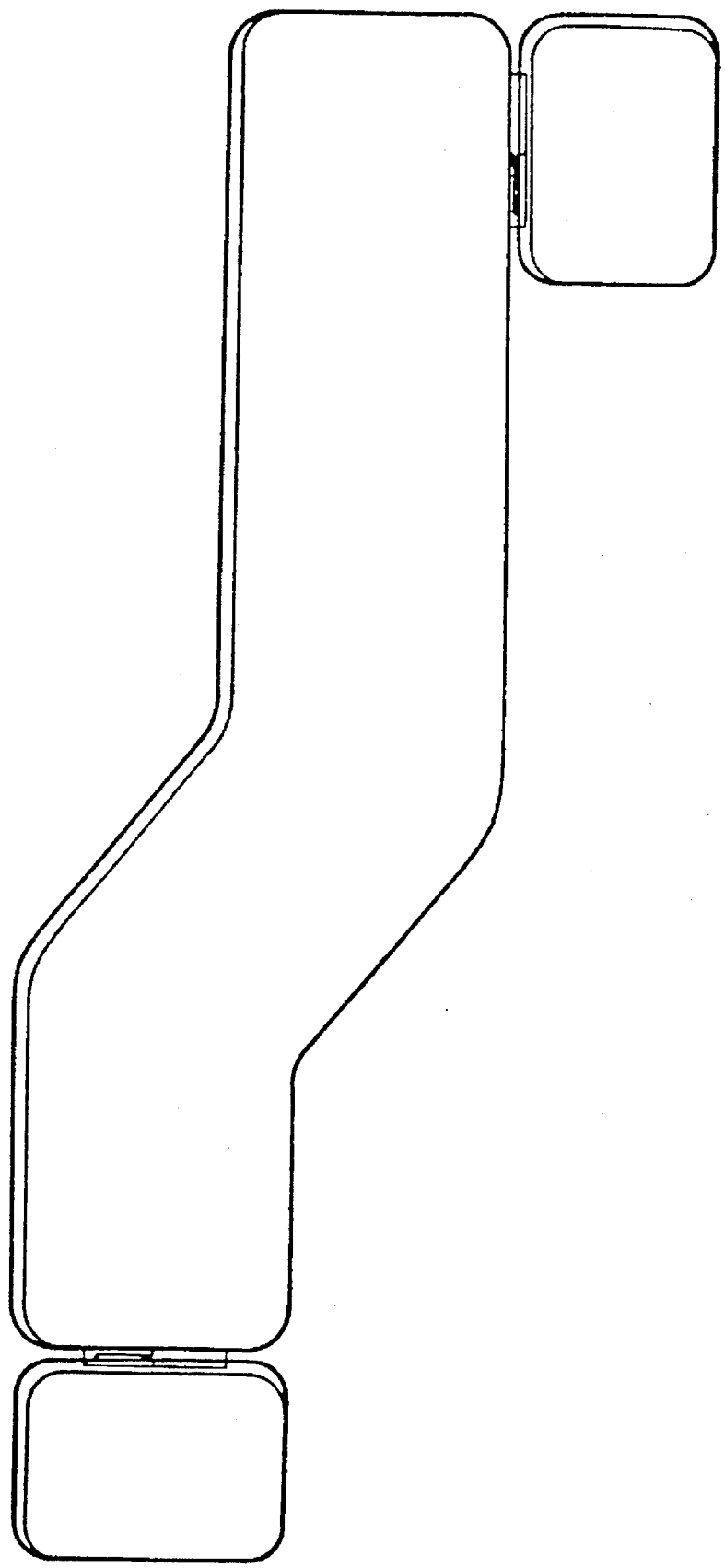
FIG. 32 is a top plane view of the wireless electrophysiological monitoring system (WEMS) as a compact wireless device-system, containing within its internal structure all the electronic components.

FIG. 32 shows a top plane view of the wireless electrophysiological monitoring system (WEMS) device as a compact self contained within all the electronic and sensing components.

Figure 33:
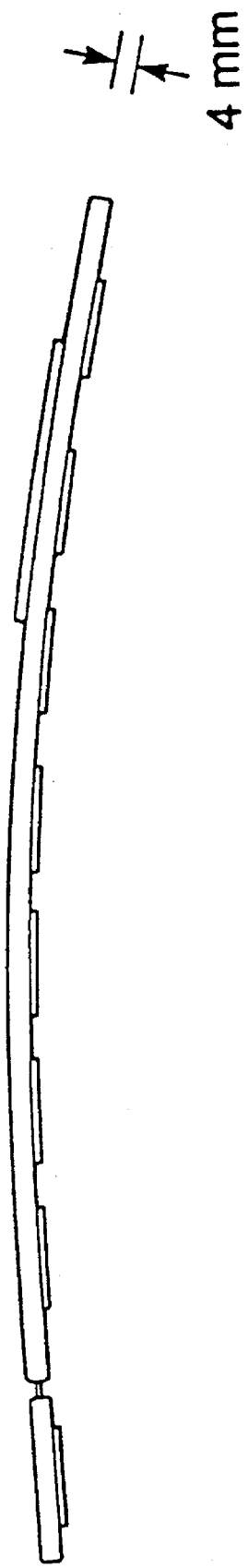
FIG. 33 is a lateral view of the wireless strip-patch having the chip mounted on the top plane within the structure of said strip-patch and having spaced apart conductive contact elements mounted on contact-to-patient plane (lower portion).

FIG. 33 is a lateral view of the wireless strip-patch device-system having the chip mounted on the top plane within the structure of said strip-patch and having spaced apart CCEs mounted on the contact-to-patient plane (lower plane). The thickness of the strip-patch is minimal to merely accommodate the dimensions of the semiconductors and other electronic components. Said thickness can range from several millimeters to about 20 millimeters, without significantly reducing the flexibility properties of said strip-patch.

Figure 34:
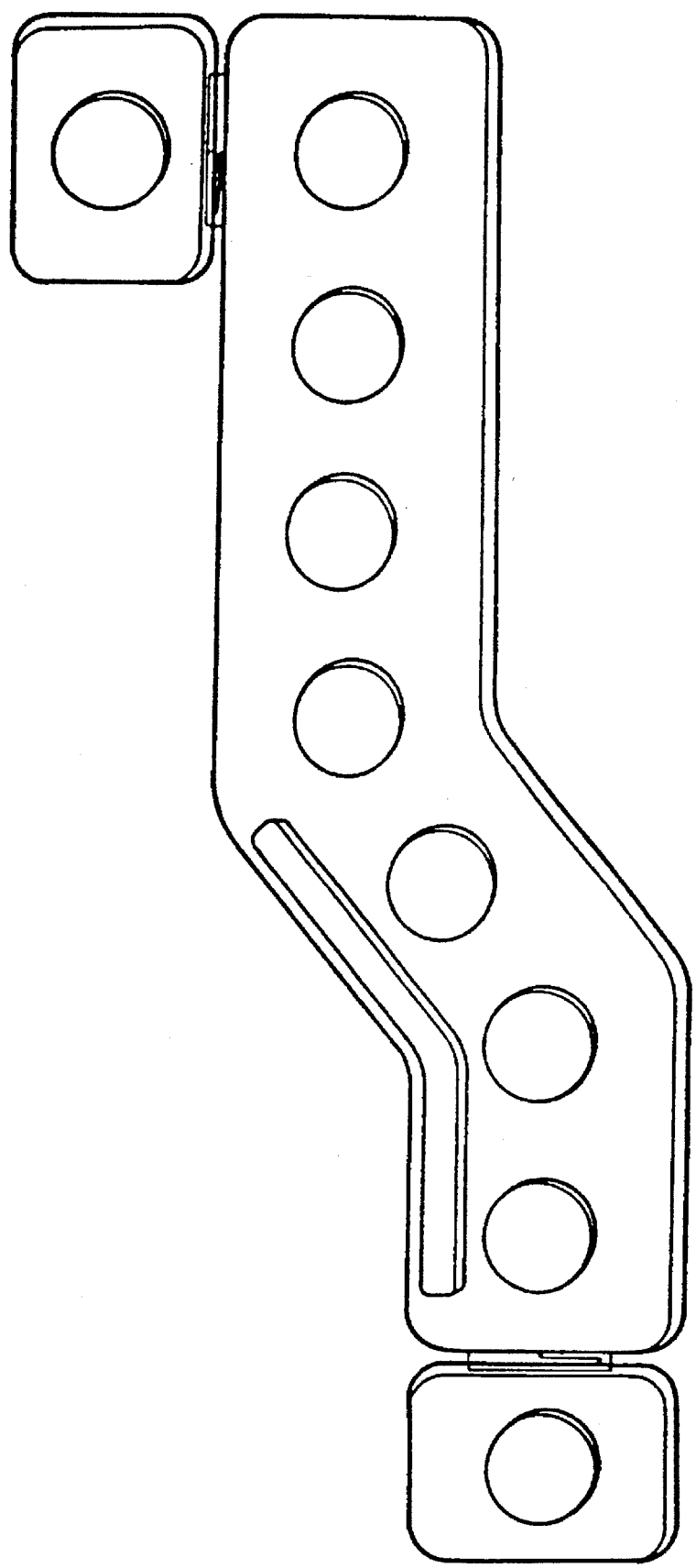
FIG. 34 is a view from the patient's skin contact with the conductive contact elements of a wireless strip-patch configured to enable standard 12-lead ECG detection.

FIG. 34 is a view from the patient's skin contact with the CCEs of a wireless strip-patch configured to enable standard 12-lead ECG detection and diagnosis.

Figure 35:
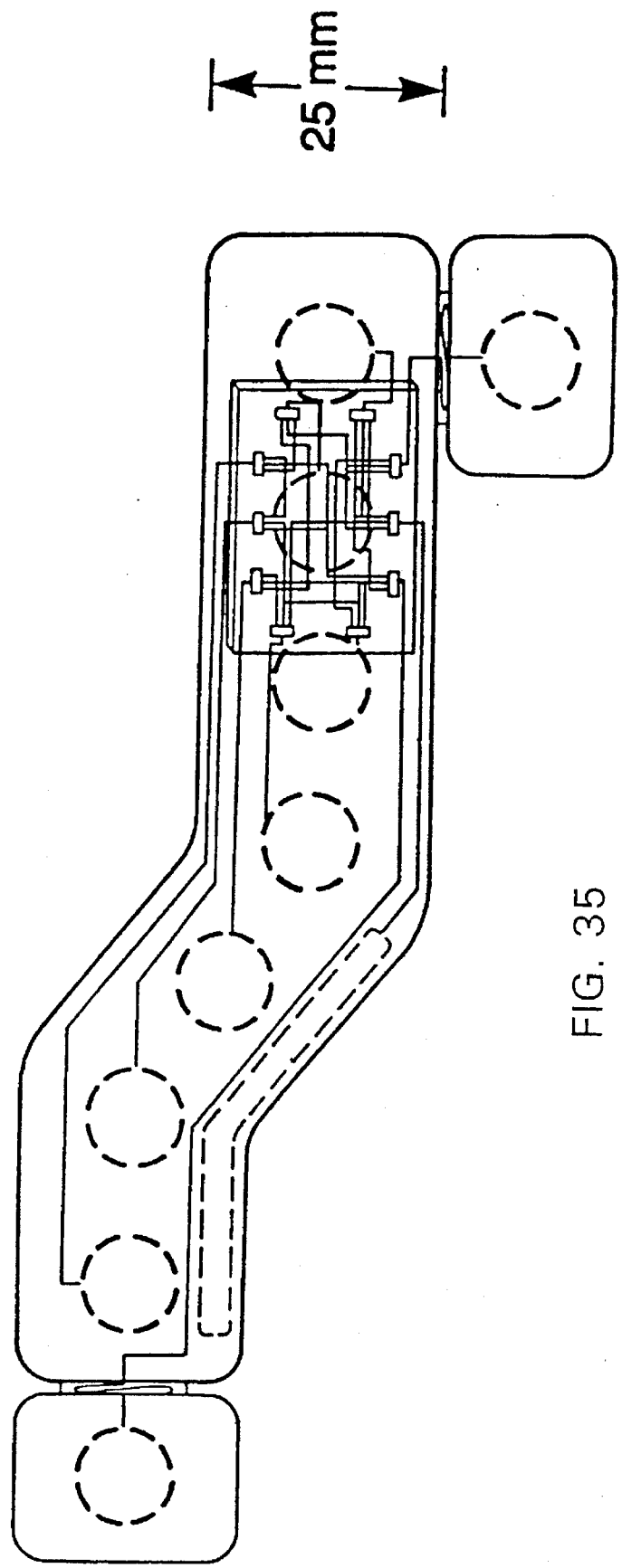
FIG. 35 is an embodiment of the wireless precordial strip-patch assembly showing the schematic structure in top plane view, configured to enable detection and diagnosis of 12-lead ECG, having ten CCEs inter-connecting to chip assembly.

FIG. 35 is a top plan view of the schematic structure of the strip-patch device-system assembly, configured to enable detection and diagnosis of 12-lead ECG, having ten CCEs interconnecting to chip assembly that allows multiplexing, encoding, microprocessing, transmission, and elaboration of data processed with link to logic and memory resident software and preset alarm triggering capabilities. The width of the strip-patch device-system is merely to accommodate the electronic components integrated within, and can range from about ten to twenty-five millimeters to about sixty millimeters.

Figure 38:
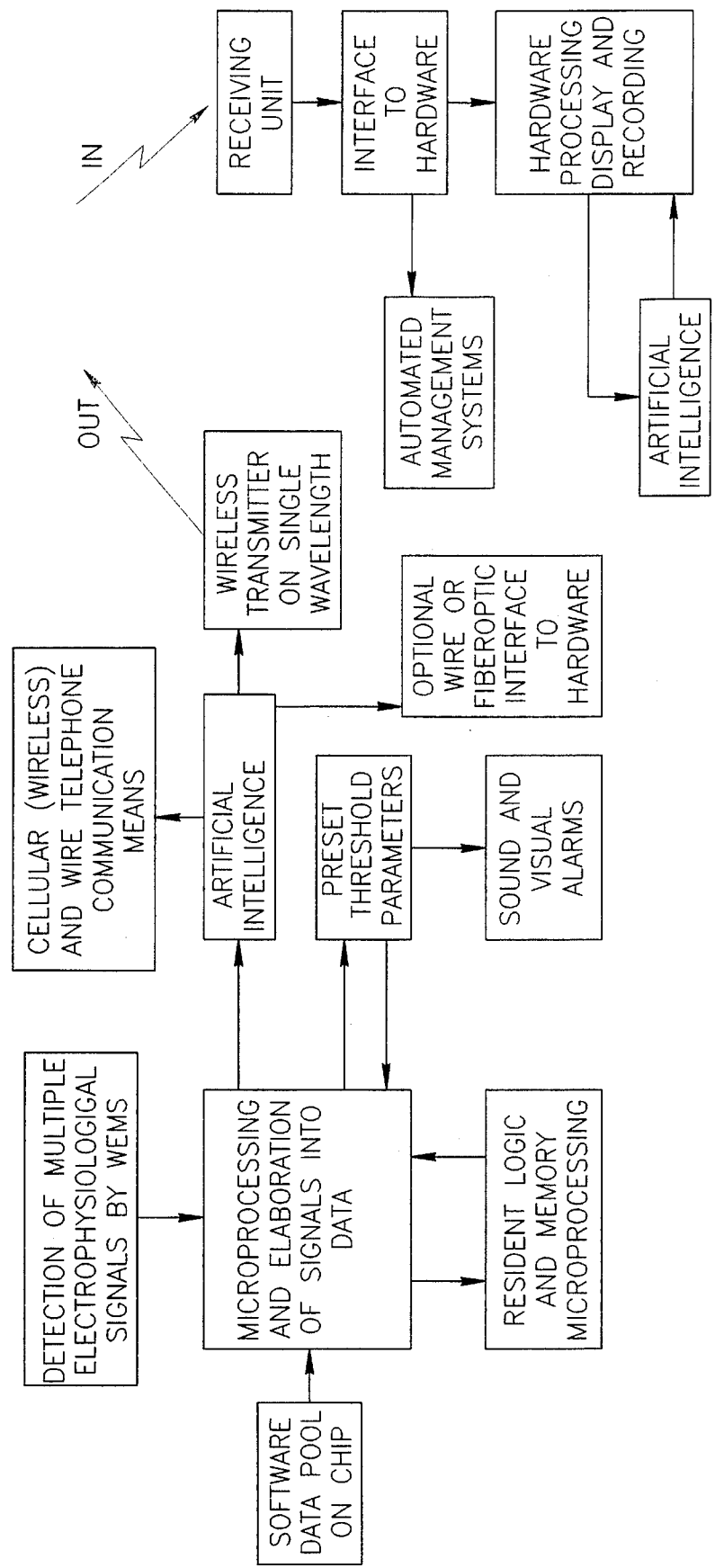
FIG. 38 is a schematic block diagram of said device-system for processing, elaboration and telemetering of data, having links to; logic-memory; data-pool; threshold parameters; sound and visual alarms triggering; and integrating telephone communication means, transmission means, and interface to recording, display, memory and management systems.
Figure 39:
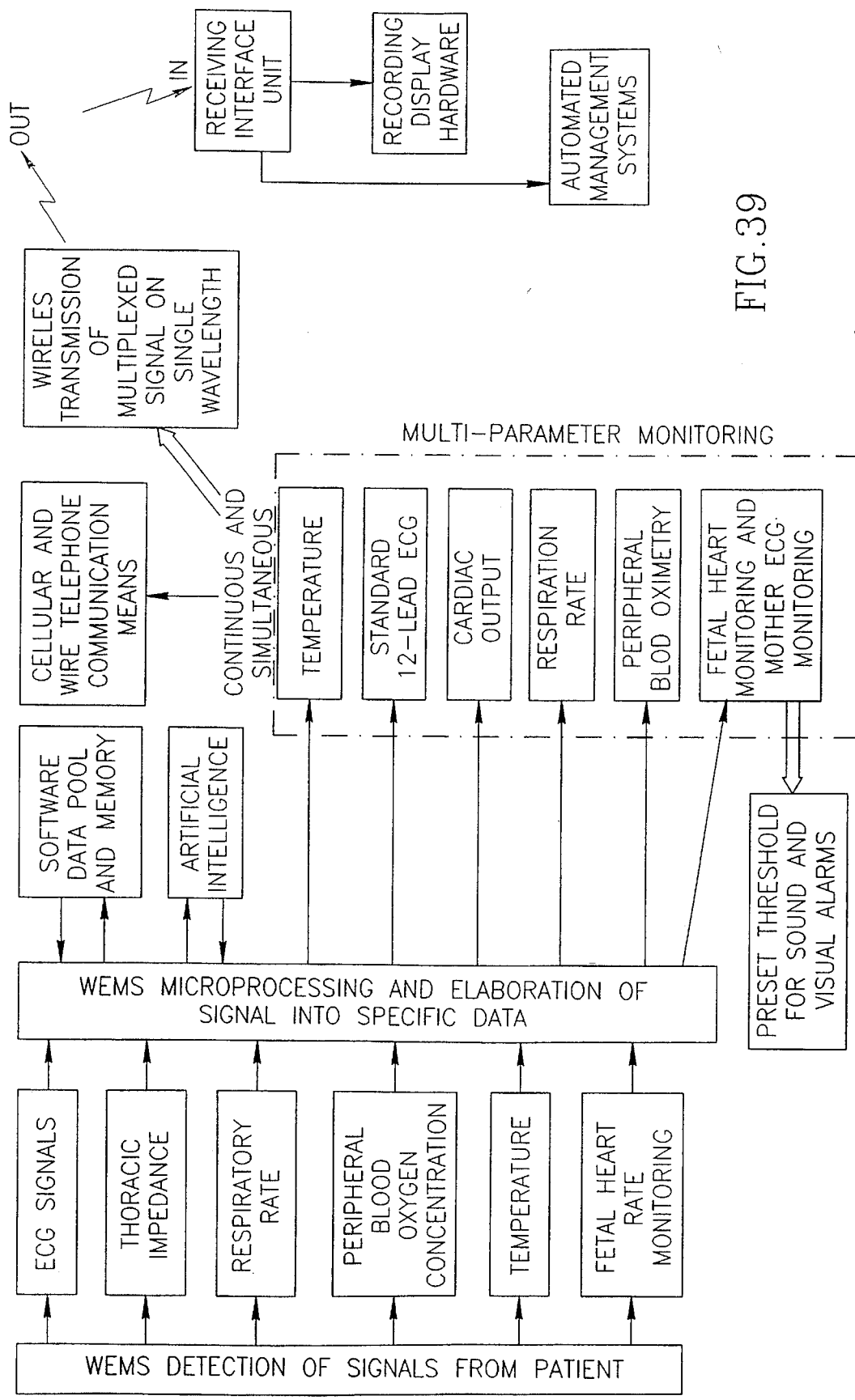
FIG. 39 is a schematic block diagram of said device-system for monitoring multiple physiological parameters, simultaneously and continuously.

Additional approaches and configurations of the wireless electrophysiological device-system having a strip-patch with multiple conductive contact elements, microsensors, microprocessing, data processing control, logic and memory resident elaboration, encoding and transmission, are incorporated within the said strip-patch and connect to all the CCEs or microsensors, which enable, in addition to 12-lead ECG, also continuous and simultaneous monitoring and measurements of cardiac output, respiration rate, peripheral blood oximetry, temperature, and fetal heart ECG monitoring. Such configurations enable the WEMS to incorporate also the capabilities of Monitoring Multiple Physiological Parameters (MMPP), continuously and simultaneously. FIG. 38 discloses a schematic block diagram of the operation principals and layout of said device-system for monitoring multiple physiological parameters, simultaneously and continuously. FIG. 39 further discloses a schematic block diagram of said device-system for processing and elaboration of data from multi-signal detections, having; logic-memory link; data pool link; preset threshold parameters; sound and visual alarms triggered by task-oriented preset threshold parameters; telephone communication means; transmission means; and, interface-link to recording, display, memory and management systems.

Figure 36:
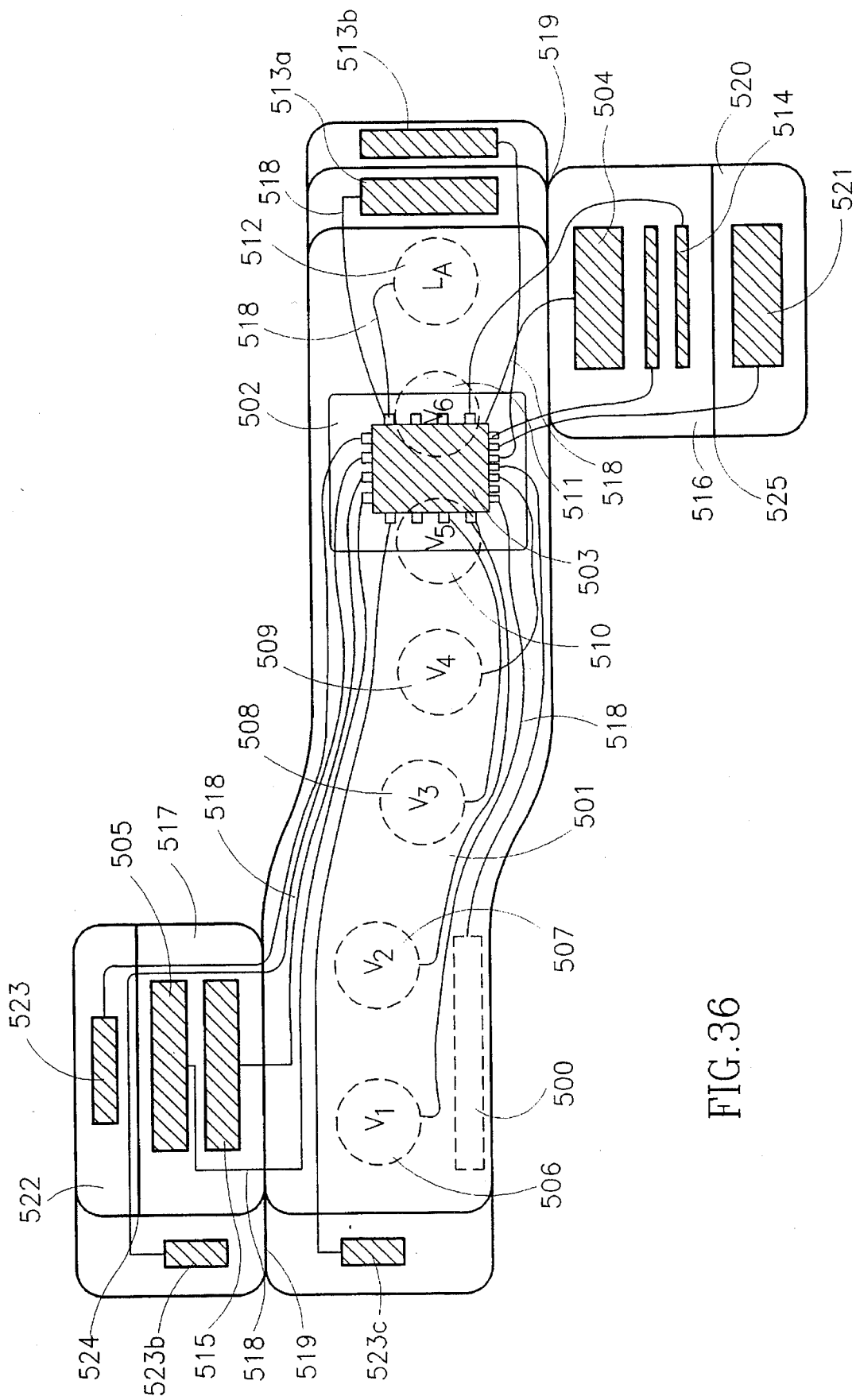
FIG. 36 is a top plane view of the wireless strip-patch single device-system configured to enable, simultaneously and continuously, the detection and monitoring of 12-lead ECG and measurement of cardiac output by means of additionally incorporating four pairs of CCEs within said strip-patch device-system assembly, in addition to the CCEs required for standard 12-lead ECG monitoring.

In another embodiment, FIG. 36, precordial strip-patch device-system assembly 501 includes an elongated strip-patch having CCEs 504–512 for 12-lead ECG and chip receptacle 502 and microchip 503 with similar electronics to that mentioned herein 381, 382, 383, 386, 368, 361, 366 and associated electronic components. CCEs 505 and 504 are for RA and LL, respectively, and CCEs 506, 507, 508, 509, 510, 511, 512 are for $V_1$–$V_6$ and LA, respectively, and 500 as common reference CCE for standard 12-lead ECG monitoring. All elements are electrically connected to microchip 503 via flexible printed circuits paths of elements 518 and alike, which are incorporated within the thickness of said assembly element 501.

Junction means 519 permit extension of elements 517 and 516 remotely from strip-patch 501, to be placed more in distance of about ten to twenty centimeters. Elements 504, 505 and 513 serve as conductive contact elements for detection, calculation and monitoring of thoracic impedance which would enable calculations and obtaining cardiac output values. The cardiac output calculation uses the detection of variations in thoracic impedance, which means the resistance of the thorax to alternate current. It is possible to inject high frequency (i.e., 70 kHz and 3 mA) of alternate electrical current to the thorax, through conductive contact elements applied and placed on its skin surface, and measure the variation of its active resistance; when the thorax contains more water ($H_2O$) it is a better conductor for alternate current. There are two aspects relating between the impedance and human physiology: (1) during inspiration the relative concentration of water in the thorax decreases and, therefore, impedance decreases, and (2) with expiration, as the relative concentration of water in the thorax is increased, thus, the impedance increases.

After obtaining the impedance measurements and filtering out its lowest frequencies, and also after first derivative calculations applied upon, the thorax impedance measurement results in a wave form which assumes an aspect similar to that of an ECG tracing wave. The related physiological events to said occurrence regard the fact that when the heart contracts and ejects blood to the large vessels which originate from it (i.e. Aorta, etc.), there is a momentary transient change in the impedance, i.e., a measurable change in every systolic ejection of blood from the heart. From said above mentioned wave of thoracic impedance, measurable in microampers, it is feasible to calculate the cardiac output, as mentioned herein. Along with the combination of ECG detection (obtainable by the strip-patch device-system of the present invention), both ventricular pre-ejection period (PEP) and ventricular ejection time (VET) can be calculated. These calculated values would allow prediction of ventricular function, by the variations of the ratio of PEP to VET, as it increases with reduced ventricular function. The knowledge of cardiac output of a patient would, therefore, enable comprehensive hemodynamic profiling, which would direct to optimization of preload, afterload and contractility of the heart. Therefore, clinically, such continuous measurements of increased or decreased impedance of the thorax can be an indicator, for example, of variations in cardiac output, pulmonary congestion, reduced ventricular function, and more.

The measurement of the thoracic impedance can be achieved with the placement of four pairs of CCEs (total of 8 CCEs) specifically positioned and placed on the skin of the patient's body; as such, two of the four pairs are considered inner CCEs and the other two CCEs pairs are considered outer CCEs. One of the inner CCEs pairs is placed at the left and right sides on the skin at the base of the neck of the patient. The second inner CCEs pair is placed at the left and right sides on the skin at the midaxillary line of the xyphoid level of the patient. One outer CCEs pair is placed about 5 cm. above the inner CCEs pair placed at right and left sides of the base of the neck. The second outer CCEs pair is placed about 5 cm. below the inner CCEs pair placed at the right and left sides at the midaxillary line of the xyphoid level of the patient. The inner CCEs pair sense current and function as sensing receptors, and are connecting to the impedance control which consists of pacing module, cardiac output monitor and computer. The two outer CCEs transmit current to the impedance control system. The impedance control system can be either external or integrated within the WEMS' strip-patch according to the present invention. The measurement of the patient's thorax impedance by the said four pairs of CCEs enables the constructing of a mean impedance wave-form calculated into its first derivative, which results into obtaining the stroke volume (blood volume ejected from the left ventricle during one systole). In the disclosed embodiment, three CCEs four pairs of CCEs, namely 521 and 514, 513a and 513b, 505 and 523, 523b and 523c (in the configuration of which strip 501 is not wireless but instead is single wired/fiberoptic connected to a monitor/hardware recorder) are shown; at one side there is power supply for the device-system (originating from the monitor hardware) and on the other side exists the single wire connection between the hardware monitor and strip 501 into which enters the injectable alternate current (i.e. 70 kHz and 3 mA) of high frequency. The wire from strip-patch 501 connects to a computer (i.e. PC) containing preset filtering software and sampling capabilities by the software of about 300 to 400 per-second, thus, at the interface unit of the strip-patch device system 501 which connects to monitor and computer, stroke volume (SV) results from calculation as herein explained, and heart rate (HR) is obtainable through the ECG detection by the strip-patch itself, thus, cardiac output is obtainable as the resulting product of SV×HR.

Further, since systemic blood pressure value is available by the monitor hardware, and cardiac output is obtainable through thoracic impedance calculations from the WEMS strip-patch device-system, as mentioned herein, thus, it is possible to calculate and simultaneously obtain by the strip-patch device-system of the present invention also values of systemic vascular resistance (SVR). The SVR is the resistance between the systemic arteries and the capillary bed. Since the capillary bed is assumed to have no blood pressure, SVR can be calculated as the resulting product of the ratio between mean systolic pressure (MSP) to cardiac output (CO), as MSP/CO. The knowledge of SVR is important in clinical conditions, for example, in shock, during epidural anesthesia, in sepsis, and more.

Therefore, the strip-patch device-system of the present invention becomes a "smart", simultaneous, comprehensive and continuous multi-parameter physiological monitor, rather than merely a single or isolated physiological parameter monitoring device.

In other configuration to enable thoracic impedance measurements, CCEs 521 and 523 serve with elements 522 and 520, respectively, and connect by flexible, extendable and stretchable junction means 519 among elements 525a and 525b, and elements 516 and 516a, respectively, and permit elements 529a and 529b to be placed remotely in distance as needed and explained herein in regards to placement of four pars of CCEs to enable measurements of thoracic impedance. Such remote positioning of CCEs for thoracic impedance measurements (1) having eight the number of CCEs employed for measurement of thoracic impedance; and (2) allowing coverage of a largest area of the thorax anatomy (eventually volume) of to be measured from and by of the eight CCEs.

Variable configurations of said strip-patch device system for simultaneous and continuous measurements, detection and monitoring of multiple physiological parameters, are possible. It should be understood that the strip-patch device-system of the present invention can contain one of each of the herein mentioned monitoring capabilities, can contain all of such monitoring capabilities at the same time, or can contain any combination thereof. Further, it should be understood that the number of CCEs shown herein is for the purpose to demonstrate per task the existence of the appropriate CCEs required. However, with reduced or increased number of CCEs than shown, or any combination thereof, yet the strip-patch device-system performing the complete range of monitoring and measurements or processing, is feasible, as some CCEs can serve be utilized for more then one type of detection purposes. Therefore, the number of the overall CCEs required in the strip-patch device-system may be decreased, increased or changed accordingly; for example, CCEs for thoracic impedance may also serve for monitoring respiration rate, and CCEs used for standard 12-lead ECG may also operate alternately for thoracic impedance calculations, fetal heart monitoring, etc.

Figure 37:
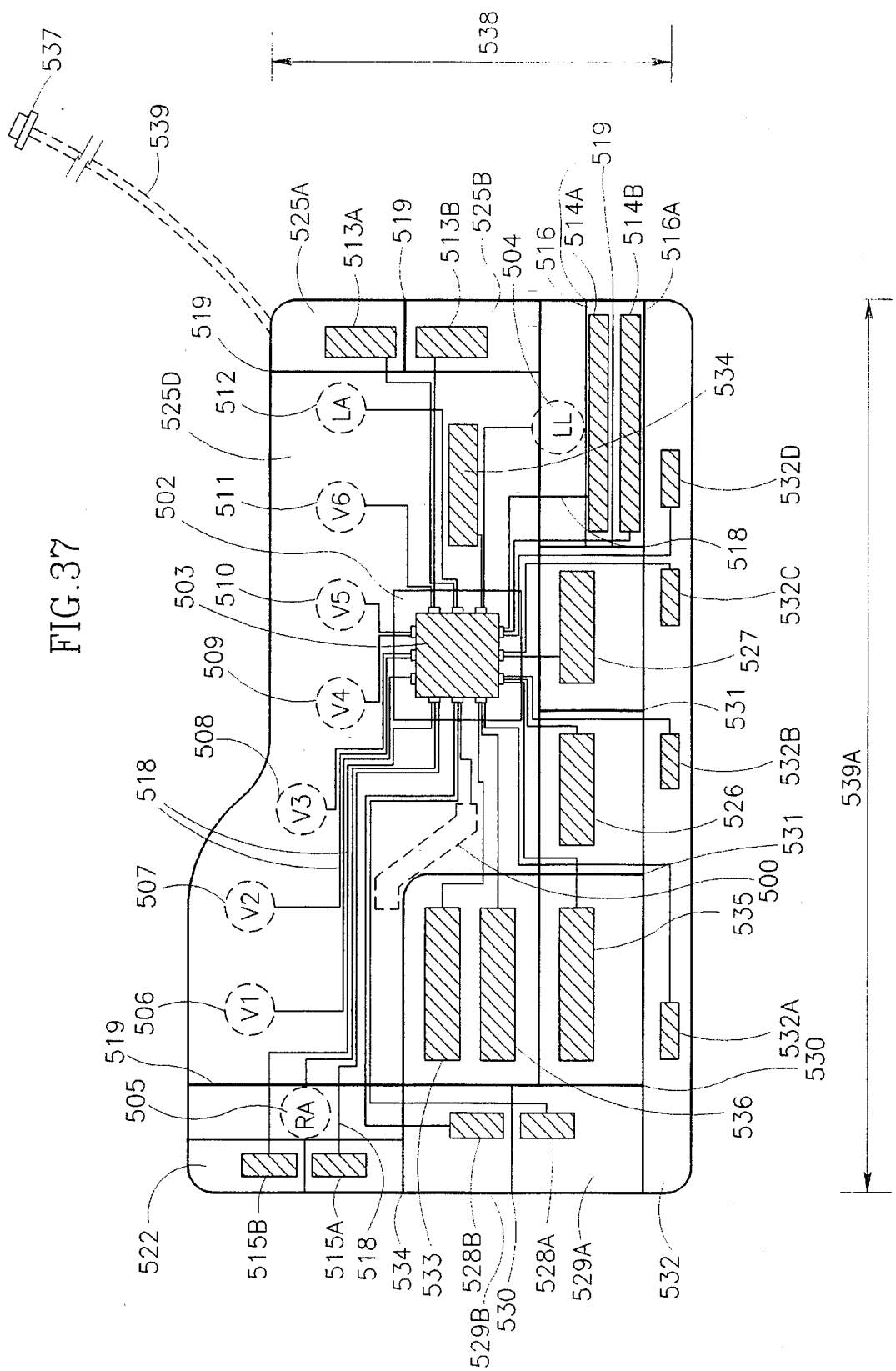
FIG. 37 is a top plane view of the wireless strip-patch single device-system configured to enable detection, measurements and monitoring, simultaneously and continuously, of multi-physiological parameters including 12-lead ECG, cardiac output, respiration rate, peripheral blood oximetry and temperature, of a patient. Said configuration is shown both for wireless operation (the transmitter is incorporated within the chip set) and with optional (presented by broken-line) single fiberoptic or single-wire connection by an interface connector to a monitor display or recording hardware.

Strip-patch 525d, see FIG. 37, contains CCEs 513a, 513b, 514a, 514b, 515a, 515b, 528a, 528b, electrically connected in four pairs, for detection and calculation of thoracic impedance, as explained herein. Said strip-patch device-system further contains CCEs 500, 506, 507, 508, 509, 510, 511, 512, 505 for detection of standard 12-lead ECG. Said strip-patch furthermore contains CCEs 534 and 536 for respiration rate monitoring. It also contains microsensor and module 527 for measurement of peripheral blood oximetry. Microchip 503 is placed in receptacle 502 and is electrically connected among and to all the CCEs by elements alike 518 of printed circuit wires incorporated within the structure of the herein mentioned strip-patch device-system. Element 535 represent and serves for temperature sensing and by means of connecting to the microchip can be triggered as programmed to operate on preset time intervals. Element 527, represent and functions as a microsensor module mounted on the strip-patch device-system, to enable the measurement of peripheral blood oximetry, as explained herein. Its function can be based on spectrophotometry analysis of reduced hemoglobin contained in red blood cells in peripheral blood versus oxygenated hemoglobin, by means of light wavelength (i.e. red) that penetrates the capillary bed under the skin's surface. The shift resulting from this analysis enables mathematical calculation by incorporated microprocessor of oxyhemoglobin saturation values versus reduced hemoglobin. Junction means 519, 530, 531, 534 permit extension of elements 522, 516, 529, 536 to be remotely positioned from element 525d, if desired. This serves for more accurate positioning of CCEs, if needed, to improve measurements' accuracy. Element 533 serves for additional reference CCE, if needed, to enhance either of the monitoring functions. Element 532 serves for fetal heart monitoring, shown herein with four (can be more) detection CCEs 532a, 532b, 532c, and 532d, for independent fetal heart rate monitoring. Said fetal heart rate monitoring elements are electrically connected to main microchip 503, for all herein mention purposes of data elaboration, microprocessing, linking to logic, memory and data pool parameters, and "on-line" interfacing to sound and visual alarms which trigger its operation by preset threshold parameters. Microchip 503 is shown, containing similar electronic components as described in FIG. 15A herein, and is compatible to connect to Section B as described in FIG. 16A herein. If wireless operation of monitoring is performed, said chip assembly contains also a transmitter, as described herein previously in FIG. 15A. Although FIGS. 15A and 16A are adapted for monitoring only 12-lead ECG, it should be understood that said chip configuration with appropriate semiconductors components can be easily adapted to perform the additional-to-ECG data processing, based on the same or adjunctive analog or digital capabilities, microprocessing and alike semiconductors operations. Element 539a is about 15 to 20 centimeters long, when all extendable elements are condensed close to 525d. Such dimensions may vary, in order to better fit female, male and pediatric chest and body sizes. Each herein mentioned extendable element can be positioned about twenty centimeters (or more) remotely from element 525d. In the configuration of which wireless mean are not used (and therefore there would be no need for a transmitter in the chip or for a power source in the strip-patch) element 539 is a single wire/cable or single fiberoptic connection mean from said strip-patch to the recording or display hardware. Element 537 is an interface module that can be multi-pin structured to adapt for computer interface, automated data management systems or link and connect with artificial intelligence capabilities and systems, if they are optionally elected to be external to said strip-patch device-system.

The non-invasive continuous recording of peripheral blood oximetry by the strip-patch of the present invention, of patients under intensive care and for ventilation-dependent neonates in intensive care, is of significant clinical importance. Patients with acute respiratory failure experience sudden changes in their cardiopulmonary status that may not be detected by other intermittent monitoring. The continuous non-invasive peripheral blood oximetry of the present invention, will be helpful in differentiating pulmonary from cardiac problem, and will avoid the need of frequent arterial blood gas analysis, which is time consuming, results delayed, and expensive. The continuous and simultaneous monitoring of peripheral blood oximetry by the strip-patch device-system of the present invention can be an alternative for; patients with contraindications for pulmonary artery catheter or for patients who their clinical status does not warrant its use; during trauma resuscitation as an indicator of inadequate oxygenation or underperfusion; and, for ventilation-dependent patients, including neonates in intensive care.

Such non-invasive and continuous monitoring of peripheral blood oximetry as offered by the strip-patch device-system can be integrated into the WEMS strip-patch monitoring capabilities by either of the following two techniques: (1) transcutaneous $O_2$ monitoring; and, (2) mixed venous oximetry. In transcutaneous $O_2$ monitoring, a polarographic sensor can be used. It can be placed on the skin at a central position of the patients body, and the elongated position of the WEMS' strip-patch is adequate. This sensor-contact element heats the stratum corneum layer of the underlying skin to about ac, which increases dermal blood flow, arterialize arterial blood flow, and increases gas ($O_2$) diffusion. This sensor-contact element consists of heating coils, temperature sensor, anode, cathode, membrane and electrolyte layer, and connections thereof. In mixed venous oximetry, reflective spectrophotometry can be used. Such technique results from the variability in light absorption characteristics of various hemoglobin molecules in the blood induced by three specific wavelengths of light that differentiate oxyhemoglobin from reduced hemoglobin. The light is transmitted from the light source via transmitting optic fibers to the skin tissue, and return via adjacent incorporated optic fibers to a photodetector cell, which measures the relative wavelength intensities. A microprocessor is connected to the light source and the photodetector cell, and calculates the oxyhemoglobin saturation.

The strip-patch device-system of the present invention that enables monitoring of multi-physiological parameters is innovative in its concept, operation, device structure and source for extensive clinical information in real time, continuously and simultaneously. Data detection and processing is completed "on the patient" at the patient's end, thus, can simplify existing hardware size, reducing it cost, facilitate significantly its operation and eliminate the need for use of diversified and multiple monitoring equipment. The microchip elaboration of data by the strip-patch single device-system, is safe, effective, fast, reliable, continuous and simultaneous, simple, economical, and provides multiple-parameter monitoring that is critical for clinical evaluation.

The structure of such element as 525a, 525b, and similar alike functionable elements, and its adjacent extendable portions, are made from flexible plastic derived materials having variable flexibility properties based on material characteristics, thickness, polymeric or plastic derived nature of the material, variability in number or order of layers of the material, and alike. Appropriate conductive polymeric material with conductive film properties can be integrated to further control specification characteristics. The strip-patch device-system can be for single use or reusable, and is compatible to operate with existing equipment for recording, display or data elaboration purposes.

The strip-patch device-system of the present invention will permit the assessment of hemodynamics with bedside measurements of cardiac function to become a standard in the critically ill patients. In hearts with reduced ventricular function, the strip-patch device-system of the present invention can offer a combination of ECG and thoracic impedance tracing to enable the prediction of the heart's ventricular function, which would enable comprehensive and critical hemodynamic profiling during intensive care of patients. The measurements and calculation of and from impedance cardiography, as mentioned herein, can provide valid estimation of stroke volume (SV) (blood volume ejected by the left ventricle of the heart during one systole) and ejection fraction (EF) (systolic volume/end-diastolic volume); therefore, end-diastolic volume (EDV) can be calculated from EDV=(SV/EF)–SV. Such strip-patch device-system of the present invention could replace other expensive, complex or invasive methods for measuring cardiac output. Thereby, cardiac output monitoring would become relatively inexpensive, always available logistically, time saving, non-risky and non-hazardously approach that will provide continuous clinical data, will be justified to be used in a large number patients, and will enhance preventive treatment to potential clinical complications. As such, the strip-patch device-system of the present invention will offer an effective, safe, practical, easy and economical method to assess continuously the adequacy of cardiac output and, ultimately, peripheral oxygen perfusion adequacy.

Further, the strip-patch device-system of the present invention will offer hemodynamics assessment of pacemaker patients for gauging responses of pacemakers to changes in programming of pacemakers or conditions affecting circulation. As such, the use by the strip-patch device-system of the present invention of impedance cardiography, as mentioned herein, can serve for non-invasive determination of cardiac output at short intervals, and will effectively address small variations in atrioventricular timing that may result in altered hemodynamics of a patient. As such, the strip-patch device-system of the present invention will provide a simple, non-invasive method, capable to monitor cardiac output, that would aid in programming patients with pacemakers for optimal hemodynamic benefit. The use of impedance cardiography by the said strip-patch device-system offers a non-invasive method of cardiac output determination that would allow repetitive measurements at short intervals with low variability, that can be directly and continuously linked or interfaced to or trigger the operation of pacemakers.

Further, the continuous and simultaneous monitoring and availability of standard 12-lead ECG and cardiac output and respiration rate and peripheral blood oximetry and temperature of a patient, by such strip-patch single device-system, operable by wireless or with only a single wire or fiberoptic connection to monitoring or recording hardware, will significantly expand and facilitate the use of multi-parameter monitoring, permit continuous monitoring, optimize patients' comfort and compliance, overcome distance limitation of monitoring, facilitate use of equipment by medical personnel, reduce the learning-curve associated with operation of equipment, avoid false-negative or false-positive of testing, expand the use and make available more clinical information by a more complete but simple and economical monitoring system, avoid the need to rely on multiple manufacturers and vendors, avoid repetitive testing, speed testing in critical circumstances, save precious time clinically, facilitate sharing of test results among medical experts, save cost of personnel time, and potentially reduce the overall costs of patient care. Furthermore, the simultaneous and continuous monitoring of multiple physiological parameters by a single device-system that will be compatible to operate with already existing recording or display hardware equipment, will allow either immediate or gradual and economical upgrade of equipment into such herein disclosed "next generation" of comprehensive patient monitoring.

The strip-patch device-system of the present invention will also integrate within and also enable continuous electrocardiographic monitoring of a fetus heart and his mother heart during the period of pregnancy, by a simple, portable, economical and easy-to-use push-button oriented having wireless communication, that would enable continuous invaluable fetal heart monitoring during high-risk pregnancies, which account to be about 25% of all pregnancies worldwide. Such mother-fetus monitoring (MOFET Monitoring) by the WEMS strip-patch system-device, will detect, simultaneously, but separately the fetus heart and the mother heart, both the maternal and fetal electrocardiographic heart monitoring, wirelessly and continuously, and transmit or link or interface it to a potable beeper-size device that may contain; microprocessor for real-time rapid elaboration of the detected heart signals; integrated software within the microprocessor calibrated to evaluate a preset threshold level capable to trigger a sound and visible alarm to alert the mother about the need to seek medical help; cellular telephone incorporating preprogrammed one or two telephone numbers for automatic or by-demand communication capabilities to medical emergency services or to a doctor's office; and, digital microprocessing to analog sound telemetering means to allow the use of conventional wired telephone communication.

In addition, the WEMS' multi-parameter monitoring capabilities of the strip-patch device-system of the present invention, would enable ambulatory or hospital-based patients to connect and interface by wireless means or by single-wire or by single fiberoptic link, or by per-visit or daily-link during hospitalization by "electronic stamp interface", to automated medical management systems. Such practical error-free link among patients and a large medical institution or doctor's office, would allow management automation of clinical data in real time, trace patients' always current records upon demand, avoid repetitive testing of patients, facilitate and accelerate comparative clinical evaluation of patient's testing (which could be automated by software), facilitate sharing of clinical information among medical professionals, avoid errors that are often associated with log of clinical data by manual cumbersome methods, and significantly reduce the overall cost of patient's care.

Furthermore, the WEMS' strip-patch device-system integrates within and self-contains also artificial intelligence in its incorporated set of chips. Such artificial intelligent programming of microchips within said strip-patch device-system enables safe, effective, rapid and economical method for optimal "on-site" ("on-patient") portable clinical judgement assessment of the patient, in real time. Such logic and memory resident capabilities by semiconductors, enables; "on-patient" portable and real-time continuous medical assessment and evaluation capabilities of variable multi-parameter clinical conditions; simultaneous testing and multi-parameter profiling; continuous control and evaluation of drug management; and, alert the patient, by self-contained and incorporated sound and visual means, of immediate need or delayed option to seek medical help, if necessary.

In view of the foregoing, it can be seen that the disclosed novel strip-patch device-system assembly of the present invention is a significant improvement over the prior art. The strip-patch device-system assembly contains a plurality of conductive contact elements, microsensors, semiconductors, microprocessors, transmitter and cellular communication means to connect to recording or monitoring hardware, continuously and simultaneously, of multi-parameter physiological data, or optionally, independent or sequential testing and telemetering of data. Multiple contact elements and microsensors are placed on a patient, including reference conductive elements that permit elimination of the standard wired right leg reference electrode, in the case of 12-lead ECG, or other reference wires for other testing. The strip-patch assembly operates as an independent "active" and "smart" detecting-sensing-processing-elaborating-encoding logic device, having optional triggering and communication capabilities thereof, as opposed to "passive" multiple electrodes currently used for electrocardiographic or other testing that have to be individually connected by multiple wires to multiple different hardware units. The strip-patch assembly includes RA and LL conductive elements positionable on the patient in a position remote from the $V_1$ through $V_6$ and LA conductive elements mounted sequentially on the elongated strip-patch. As such, the strip-patch device-system of the present invention provides a self contained strip-patch assembly-system for detecting and transmitting standard 12-lead electrocardiogram heart signals, cardiac output, respiration rate, peripheral blood oximetry, temperature, and fetal heart monitoring, each of which can be optionally detected separately or simultaneously, and continuously, processed and transmitted to a recording or display monitoring hardware.

While particular embodiments have been shown and described herein, it will be apparent to those skilled in the art that variations and modifications may be made in these embodiments without departing from the spirit and scope of this invention. It is the purpose of the appended claims to cover any and all such variations and modifications.

What is claimed is:

1. An electrode structure for use in a wireless patient monitoring system, including:

a) non-conductive strip means of selected length and width for supporting a signal transmitter on one side thereof and a plurality of conductive element pairs on the other side thereof, each of said conductive element pairs being in spaced relationship to each other and exposed on said other side of said strip means;

b) battery means having at least one voltage terminal and a ground terminal carried on said strip means;

c) microchip amplifier means carried on said strip means for amplifying signals and having signal input terminal means coupled to a first conductive element of each pair of conductive elements for receiving physiological signals therefrom and having output terminal means, d) microchip multiplexer means carried on said strip means having input terminal means coupled to the output terminal means of the amplifier means for receiving the physiological signals therefrom and multiplexing same and having output terminal means, e) a microchip encoder-modulator carried on said strip means for encoding and modulating multiplexed signals and having input terminal means coupled to said output terminal means of said multiplexer means and having output terminal means;

f) microchip transmitter carried by said strip means for transmitting coded-modulated signals and having input terminal means and output terminal means, said input terminal means of said transmitter being coupled to said output terminal means of said encoder-modulator means;

g) a wireless-signal radiator having input terminal means coupled to said output terminal means of said microchip transmitter means for radiating the coded-modulated signals;

h) means for applying operating potentials from said battery to said microchip amplifier means, encoder-modulator and transmitter means; and i) means for coupling said ground terminal of said battery to said second conductive element of each pair of conductive elements.

2. An electrode structure according to claim 1 wherein said amplifier means includes noise coil means coupled to the second conductive element of the corresponding pair of conductive elements for detecting background noise, differential input amplifier means having a non-inverting input terminal coupled to said first conductive element of the corresponding pair of conductive elements and an inverting terminal coupled to said noise coil means for subtracting the background noise signal from the signal present on said first conductive element of the corresponding pair of conductive elements.

3. An electrode structure for use in a wireless patient monitoring system, including:

a) non-conductive strip means of selected length and width for supporting a signal transmitter on one side thereof and a plurality of conductive element pairs on the other side thereof, each of said conductive element pairs being in spaced relationship to each other and exposed on said other side of said strip means;

b) battery means having at least one voltage terminal and a ground terminal carried on said strip means;

c) a microchip amplifier carried on said strip means and having a signal input terminal coupled to a first conductive element of a corresponding pair of conductive elements for receiving heart signals therefrom and having an output terminal, d) a microchip multiplexer carried on said strip means and having an input terminal coupled to the output terminal of said amplifier and having an output terminal, e) a microchip encoder-modulator carried on said strip means and having an input terminal coupled to said output terminal of said amplifier and having an output terminal;

f) a microchip transmitter carried by said strip means and having an input terminal coupled to said output terminal of said encoder-modulator and an output terminal;

g) a wireless-signal radiator having an input terminal coupled to said output terminal of said microchip transmitter;

h) means for applying operating potentials from said battery to said microchip amplifier, encoder-modulator and transmitter; and i) means for coupling said ground terminal of said battery to said second conductive element of each pair of conductive elements.

4. A strip assembly for placement on a patient having a heart with a precordium lying thereover, skin and right and left arms and legs comprising an elongate strip having first and second surfaces, a plurality of conductive contact elements being mounted in spaced apart position along the length of said strip, and being exposed on the first surface of said strip and being adapted to contact said patient's skin, a reference contact element mounted on said strip and serving as a common reference for each of said plurality of conductive contact elements, said reference contact element being exposed on the first surface of said strip and being adapted to contact said patient's skin, said contact elements capable of detecting psychological signals from said patient to produce a plurality of such physiological signals correlated with multiple physiological parameters of the patient; conductor means connected to said plurality conductive contact elements and said reference contact element to permit electrical transmission of said detected signals, and microchip means carried by said strip coupled to said conductor means for amplifying multiplexing and transmitting the detected signals.

5. A strip assembly according to claim 4 wherein said strip is substantially continuous between said plurality of conductive elements.

6. A strip assembly according to claim 4 wherein the microchip means encodes and modulates the multiplexed detected signals.

7. A strip assembly according to claim 6 wherein the encoding and modulating is effected by pulse code modulation.

8. A strip assembly for placement on the chest of a patient having a heart with a precordium lying thereover, skin and right and left arms and legs comprising an elongate strip having first and second surfaces, six conductive contact elements identified as $V_1$ through $V_6$ being mounted in spaced apart position along the length of said strip, said $V_1$ through $V_6$ conductive contact elements being exposed on the first surface of said strip and being adapted to contact said patient's precordium, additional conductive contact elements identified respectively as LA and LL mounted on said strip near said $V_6$ conductive contact element, said LA and LL conductive contact elements being exposed on the first surface of said strip and being adapted to contact said patient's skin near said left arm and left leg respectively, an additional conductive contact element identified as RA mounted on said strip near said $V_1$ conductive contact element, said RA conductive contact element being exposed on the first surface of said strip and being adapted to contact said patient's skin near said right arm, said strip being substantially continuous between said conductive contact elements, a reference contact element mounted on said strip and serving as a common reference for each of said $V_1$ through $V_6$, LA, LL and RA conductive contact elements, said reference contact element being exposed on the first surface of said strip and being adapted to contact said patient's skin, said contact elements capable of detecting heart signals from said patient to produce a twelve-lead electrocardiogram, conductor means connected to said conductive contact elements and said reference contact element to permit electrical transmission of said detected heart signals, and microchip means carried on said strip including amplifier means coupled to said conductor means for amplifying detected heart signals, multiplexer means for multiplexing amplified detected heart signals, encoder-modulating means for encoding and modulating the multiplexed signals and transmitter means for transmitting the encoded and modulated multiplexed signals.

9. A strip assembly for use on a patient having a heart with a precordium lying thereover, skin and right and left arms and legs comprising an elongate strip having first and second surfaces, a plurality of conductive contact elements mounted in spaced apart positions along the length of said strip, said conductive contact elements being exposed on the first surface of said strip and being adapted to contact said patient's skin for detecting physiological signals from said patient indicative of multiple physiological parameters when said strip assembly is placed on the skin of the patient, a microchip mounted on said strip and conductor means electrically connecting said contact elements to said microchip, said microchip including means for transmitting a radio frequency signal which carries a multiplex of the signals detected by said contact elements.

10. A strip assembly according to claim 9 wherein the physiological parameters include at least one of cardiac function, respiration rate, peripheral blood oximetry, temperature, fetal heart function and thoracic impedance.

11. A strip assembly according to claim 10 wherein the physiological parameters include at least two of the listed parameters.

12. A strip assembly according to claim 11 wherein the physiological parameters include cardiac function and one other listed parameter.

13. A precordial strip assembly for use on a patient having a heart with a precordium lying thereover, skin and right and left arms and legs comprising an elongate strip having first and second surfaces, six conductive contact elements identified as $V_1$ through $V_6$ mounted in spaced apart positions along the length of said strip, said conductive contact elements being exposed on the first surface of said strip and being adapted to contact said patient's skin for detecting heart signals from said patient when said precordial strip assembly is placed on the precordium of the patient, a microchip mounted on said strip and conductor means electrically connecting said contact elements to said microchip, said microchip including means for transmitting a radio frequency signal which carries a multiplex of the heart signals detected by said contact elements.

14. A strip assembly for use on a patient having a heart with precordium lying thereover, skin and right and left arms and legs comprising an elongate strip having first and second surfaces, a plurality of conductive contact elements mounted in spaced apart positions along the length of said strip, said conductive contact elements being exposed on the first surface of said strip and being adapted to contact said patient's skin for detecting physiological signals from said patient indicative of multiple physiological parameters when said strip assembly is placed on the skin of the patient, junction means carried in a single region by said strip and electrically connected to said conductive contact elements and a microchip mounted on said strip in contact with said junction means, said microchip including means for transmitting a radio frequency signal which carries a multiplex of the signals detected by said contact elements.

15. A strip assembly for use on a patient having a heart with a precordium lying thereover, skin and right and left arms and legs comprising an elongate strip having first and second surfaces, six conductive contact elements identified as $V_1$ through $V_6$ mounted in spaced apart positions along the length of said strip, said conductive contact elements being exposed on the first surface of said strip and being adapted to contact said patient's skin for detecting heart signals from said patient when said precordial strip assembly is placed on the precordium of the patient, junction means carried in a single region by said strip and electrically connected to said conductive contact elements and a microchip mounted on said junction means, said microchip including means for transmitting a radio frequency signal which carries a multiplex of the heart signals detected by said contact element.

16. An electrode assembly for use on a patient having a heart in a body comprising a layer of insulating material having first and second surfaces, a sufficient number of conductive contact elements for obtaining signals indicative of multiple physiological parameters mounted in spaced apart positions on said layer of insulating material, said contact elements being exposed on the first surface of said layer of insulating material and being adapted to contact said patient's body for detecting physiological signals therefrom, a microchip mounted on said layer of insulating material and conductor means electrically connecting said contact elements to said microchip, said microchip including means for transmitting a radio frequency signal which carries a multiplex of the signals detected by said contact elements.

17. An electrode assembly for use on a patient having a heart in a body comprising a layer of insulating material having first and second surfaces, a sufficient number of conductive contact elements for obtaining a twelve-lead electrocardiogram mounted in spaced apart positions on said layer of insulating material, said contact elements being exposed on the first surface of said layer of insulating material and being adapted to contact said patient's body for detecting heart signals therefrom, a microchip mounted on said layer of insulating material and conductor means electrically connecting said contact elements to said microchip, said microchip including means for transmitting a radio frequency signal which carries a multiplex of the heart signals detected by said contact elements.

18. A self-contained electrode structure for use in a wireless patient monitoring system for receiving physiological signals from the body of a patient comprising a layer of insulating material having first and second sides, a plurality of conductive elements carried by said layer of insulating material and disposed on said first side of said layer of insulating material, a battery carried on said second side of said layer of insulating material, microchip amplifier, multiplexing and transmitter means carried on said second side of said layer of insulating material and being coupled to said battery and to said conductive elements for receiving physiological signals from the body of the patient, and for amplifying same, multiplexing the amplified signals and transmitting multiplexed wireless signals in accordance with signals received.

19. A self contained electrode structure according to claim 18 wherein the plurality of conductive elements monitor simultaneously multiple at least two different physiological parameters.

20. A self-contained electrode structure for use in a wireless patient monitoring system for receiving signals from the heart in a body of a patient comprising a layer of insulating material having first and second sides, a plurality of conductive elements carried by said layer of insulating material and disposed on said first side of said layer of insulating material, a battery carried on said second side of said layer of insulating material, microchip amplifier, multiplexing and transmitter means carried on said second side of said layer of insulating material and being coupled to said battery and to said conductive elements for receiving heart signals from the heart of the patient and for transmitting amplified multiplexed wireless signals in accordance with heart signals received.

21. A self-contained electrode structure wherein a part of said conductive elements receive signals from the body of the patient correlated to a different physiological parameter.

22. A method of electrocardiographic monitoring on a patient having a body with a heart therein and a precordium lying over the heart comprising the steps of placing an electrode assembly on the precordium of said patient, said electrode assembly having an elongate strip with first and second surfaces and six conductive contact elements identified as $V_1$ through $V_6$ mounted in spaced apart positions along the length of said strip and a microchip mounted on said strip in electrical contact with said $V_1$ through $V_6$ conductive contact elements, placing conductive contact elements identified as LA, LL, and RA and a reference contact element on the body of said patient in electrical contact with said microchip, detecting heart signals from said patient through said contact elements, processing the heart signals in said microchip to produce a multiplex of twelve-lead electrocardiogram signals and transmitting a radio frequency signal which carries said multiplex of twelve-lead electrocardiogram signals.

23. A method of physiological monitoring a patient having a body with a heart therein and a precordium lying over the heart comprising the steps of placing an electrode assembly on the body of said patient, said electrode assembly having an elongate strip with first and second surfaces and a plurality of conductive contact elements mounted in spaced apart positions along the length of said strip and a microchip mounted on said strip in electrical contact with said conductive contact elements, placing a reference contact element on the body of said patient in electrical contact with said microchip, detecting multiple physiological signals from said patient through said contact elements, processing the detected signals in said microchip to produce a multiplex of the multiple physiological signals and transmitting said multiplexed signals.

24. The method of claim 23 wherein the step of transmitting uses a radio frequency signal.

25. The method of claim 23 wherein the step of transmitting uses an optic fiber.

26. An electrode assembly for use on a patient having a body comprising a plurality of layers of insulating material having first and second surfaces, a sufficient number of conductive contact elements for obtaining a twelve-lead electrocardiogram mounted on said layers of insulating material, at least one conductive contact element being mounted on each said layer of insulating material, said contact elements being exposed on the first surface of said layers of insulating material and being adapted to contact said patient's body for detecting heart signals therefrom, a microchip mounted on one of said layers of insulating material and conductor means electrically connecting said contact elements to said microchip, said microchip including means for transmitting a radio frequency signal which carries a multiplex of the heart signals detected by said contact elements.

27. An electrode assembly for use on a patient having a body comprising a plurality of layers of insulating material having first and second surfaces, a sufficient number of conductive contact elements for obtaining signals indicative of multiple physiological parameters mounted on said layers of insulating material, at least one conductive contact element being mounted on each said layer of insulating material, said contact elements being exposed on the first surface of said layers of insulating material and being adapted to contact said patient's body for detecting signals therefrom, indicative of multiple physiological parameters, a microchip mounted on one of said layers of insulating material and conductor means electrically connecting said contact elements to said microchip, said microchip including means for transmitting a signal which carries a multiplex of the multiple physiological parameter signals detected by said contact elements.

28. An electrode assembly according to claim 27 wherein the physiological parameters include at least one, correlated with cardiac function, respiration rate, peripheral blood oximetry, temperature, fetal heart function and thoracic impedance.

29. A method of electrocardiographic monitoring on a patient having a body with a heart therein comprising the steps of selecting an electrode assembly having a sufficient number of conductive contact elements for producing a twelve-lead electrocardiogram and a microchip electrically connected to said contact elements, placing said electrode assembly on the body of said patient, detecting heart signals from said patient through said contact elements and transmitting from said microchip a signal which carries a multiplex of the heart signals detected by said contact elements.

30. The method of claim 29 wherein the step of transmitting uses a radio frequency signal.

31. The method of claim 29 wherein the step of transmitting uses an optic fiber.

32. The method of claim 29 wherein the steps of transmitting is carried out telephonically.

33. A method of physiologically monitoring a patient having a body with a heart therein comprising the steps of selecting an electrode assembly having a sufficient number of conductive contact elements for producing signals indicative of at least two physiological parameters and a microchip electrically connected to said contact elements, placing said electrode assembly on the body of said patient, detecting signals from said patient through said contact elements and transmitting from said microchip a signal which carries a multiplex of the at least two physiological parameters detected by said contact elements.

34. The method of claim 33 wherein at least one of the physiological parameters is correlated with one of cardiac function, respiration rate, peripheral blood oximetry, temperature, fetal heart function and thoracic impedance.

35. The method of claim 33 including the further step of encoding and modulating the multiplex prior to transmitting.

36. The method of claim 35 wherein pulse code modulation is used for the step of encoding and modulating.

37. The method of claim 33 wherein the step of transmitting uses a radio frequency.

38. The method of claim 33 wherein the step of transmitting uses an optical fiber.

39. The method of claim 33 wherein the step of transmitting is effected telephonically.

* * * * *